(12) United States Patent
Lin et al.

(10) Patent No.: US 12,692,302 B2
(45) **Date of Patent: \*Jul. 28, 2026**

(54) USES OF IL-13 ANTAGONISTS FOR TREATING ATOPIC DERMATITIS

(71) Applicant: Genentech, Inc., South San Francisco, CA (US)

(72) Inventors: ChinYu Lin, South San Francisco, CA (US); Theodore A. Omachi, South San Francisco, CA (US); Ryan P. Owen, South San Francisco, CA (US); Karl Yen, South San Francisco, CA (US); Yanan Zheng, Cupertino, CA (US); Kendra Debusk, New Hope, PA (US)

(73) Assignee: Genentech, Inc., South San Francisco, CA (US)

( \* ) Notice: Subject to any disclaimer, the term of this patent is extended or adjusted under 35 U.S.C. 154(b) by 896 days.

This patent is subject to a terminal disclaimer.

(21) Appl. No.: 17/882,932

(22) Filed: Aug. 8, 2022

(65) Prior Publication Data

US 2022/0372131 A1 Nov. 24, 2022

Related U.S. Application Data

(63) Continuation of application No. 16/356,309, filed on Mar. 18, 2019, now Pat. No. 11,434,286, which is a continuation of application No. PCT/US2017/052891, filed on Sep. 22, 2017.

(60) Provisional application No. 62/539,037, filed on Jul. 31, 2017, provisional application No. 62/530,683, filed on Jul. 10, 2017, provisional application No. 62/527,204, filed on Jun. 30, 2017, provisional application No. 62/398,713, filed on Sep. 23, 2016.

(51) Int. Cl.

| | |
|---|---|
| *C07K 16/24* | (2006.01) |
| *A61K 9/00* | (2006.01) |
| *A61K 9/19* | (2006.01) |
| *A61K 31/573* | (2006.01) |
| *A61K 39/395* | (2006.01) |
| *A61P 17/00* | (2006.01) |
| *A61K 39/00* | (2006.01) |

(52) U.S. Cl.
CPC .......... *C07K 16/244* (2013.01); *A61K 9/0014* (2013.01); *A61K 9/0024* (2013.01); *A61K 9/19* (2013.01); *A61K 31/573* (2013.01); *A61K 39/3955* (2013.01); *A61P 17/00* (2018.01); *A61K 2039/505* (2013.01); *A61K 2039/545* (2013.01); *C07K 2317/24* (2013.01); *C07K 2317/56* (2013.01); *C07K 2317/76* (2013.01)

(58) Field of Classification Search
CPC .......... A61K 39/3955; A61K 2039/505; A61K 39/395; A61P 17/00; C07K 2317/56
See application file for complete search history.

(56) References Cited

U.S. PATENT DOCUMENTS

| | | |
|---|---|---|
| 2012/0156194 A1 | 6/2012 | Arron |
| 2014/0072583 A1 | 3/2014 | Ardeleanu et al. |
| 2016/0036359 A1 | 2/2016 | Streicher |

FOREIGN PATENT DOCUMENTS

| | | |
|---|---|---|
| WO | 2005/062967 A2 | 7/2005 |
| WO | 2007/045477 A2 | 4/2007 |
| WO | 2013066866 A1 | 5/2013 |

OTHER PUBLICATIONS

Simpson et al., Efficacy and Safety of Lebrikizumab in Patients with Atopic Dermatitis: a Phase II Randomized, Controlled Trial (TREBLE), Department of Dermatology, School of Medicine, Oregon Health & Sciences University, Portland, OR, Oct. 1, 2016 (14 pages).
Eichenfield et al., "Lebrikizumab Improves Patient-Reported Outcomes (PROs) in a Phase 2 Study in Patients with Atopic Dermatitis", Annual Meeting of the American Academy of Dermatology, Orlando, Florida, USA, Mar. 3-7, 2017 (1 page).
Beck et al., "Dupilumab Treatment in Adults with Moderate-to-Severe Atopic Dermatitis", The New England Journal of Medicine, vol. 371, No. 2, Jul. 10, 2014, pp. 130-139.
Corren et al., "Lebrikizumab Treatment in Adults with Asthma", The New England Journal of Medicine, vol. 365, No. 12, Sep. 22, 2011, pp. 1088-1098.
Noonan et al., "Dose-Ranging Study of Lebrikizumab in Asthmatic Patients Not Receiving Inhaled Steroids", J. Allergy Clin. Immunol., vol. 132, No. 3, Sep. 2013, pp. 567-574.e12 (20 pages).
Boruvka et al., "Psychometric Validation of the Atopic Dermatitis Impact Questionnaire (ADIQ)", ISPOR 22nd Annual International Meeting, Boston, MA, USA, May 20-24, 2017 (1 page).
Hanania et al., "Lebrikizumab in Moderate-to-Severe Asthma: Pooled Data from Two Randomised Placebo-Controlled Studies", Thorax, vol. 70, May 22, 2015, pp. 748-756.
Hanania et al., "Efficacy and Safety of Lebrikizumab in Patients with Uncontrolled Asthma (Lavolta I and Lavolta II): Replicate, Phase 3, Randomised, Double-Blind, Placebo-Controlled Trials", Lancet Respir. Med., vol. 4, Oct. 2016, pp. 781-796.
Simpson et al., "Efficacy and Safety of Lebrikizumab (An Anti-IL-13 Monoclonal Antibody) in Adults with Moderate-to-Severe Atopic Dermatitis Inadequately Controlled by Topical Corticosteroids: A Randomized, Placebo-Controlled Phase II Trial (Treble)", J. Am. Acad. Dermatol., vol. 78, No. 5, May 2018, pp. 864-871.e11 (20 pages).

(Continued)

*Primary Examiner* — Dong Jiang

(74) *Attorney, Agent, or Firm* — Robert Johnson

(57) ABSTRACT

Uses of IL-13 antagonists for treating atopic dermatitis are provided. Also provided are methods of treating atopic dermatitis and methods of reducing the severity of atopic dermatitis by administering IL-13 antagonists.

17 Claims, 17 Drawing Sheets

Specification includes a Sequence Listing.

(56) References Cited

OTHER PUBLICATIONS

Anonymous, "A Study of Lebrikizumab in Participants With Persistent Moderate to Severe Atopic Dermatitis," ClinacalTrials.gov Identifier: NCT02340234, Sponsor: Hoffmann-La Roche, URL: https://clinicaltrials.gov/ct2/show/study/NCT02340234, First Posted: Jan. 16, 2015, Last Update Posted: Oct. 2, 2017 (9 pages).

Anonymous, "A Study to Evaluate the Safety of Lebrikizumab Compared to Topical Corticosteroids in Adult Patients With Atopic Dermatitis," ClinicalTrials.gov Identifier: NCT02465606, Sponsor: Hoffmann-La Roche, URL: https://clinicaltrials.gov/ct2/show/NCT02465606?term=Lebrikizumab&cond=atopic+dermatitis&rank=1, First Posted: Jun. 8, 2015, Last Update Posted: Nov. 2, 2016 (6 pages).

Anonymous, "Phase 2 Study to Evaluate the Efficacy and Safety of Tralokinumab in Adults With Atopic Dermatitis (D2213C00001)," ClinicalTrials.gov Identifier: NCT02347176, Sponsor: Medimmune LLC, URL: https://clinicaltrials.gov/ct2/show/NCT02347176?term=tralokinumab&cond=Atopic+Dermatitis&rank=4, First Posted: Jan. 27, 2015; Results First Posted: Jun. 7, 2017, Last Update Posted: Jun. 7, 2017 (7 pages).

Hamilton et al., "Drug evaluation review: dupilumab in atopic dermatitis," Immunotherapy, 7(10): 1043-1058 (2015).

Heratizadeh et al., "Anti-inflammatory therapies in atopic dermatitis," Allergy, 71(12): 1666-1675 (Dec. 2016).

Howell et al., "Past, present, and future for biologic intervention in atopic dermatitis," Allergy, 70(8): 887-896 (Aug. 2015).

Oshima et al., "Characterization of a powerful high affinity antagonist that inhibits biological activities of human interleukin-13", J. Biol. Chem., 276(18): 15185-15191 (May 2001).

Renert-Yuval et al., "Systemic therapies in atopic dermatitis: The pipeline," Clinics in Dermatology, 35(4): 387-397 (Epub Mar. 2017).

International Search Report for International Application No. PCT/US2017/052891, mailed Jan. 9, 2018 (22 pages).

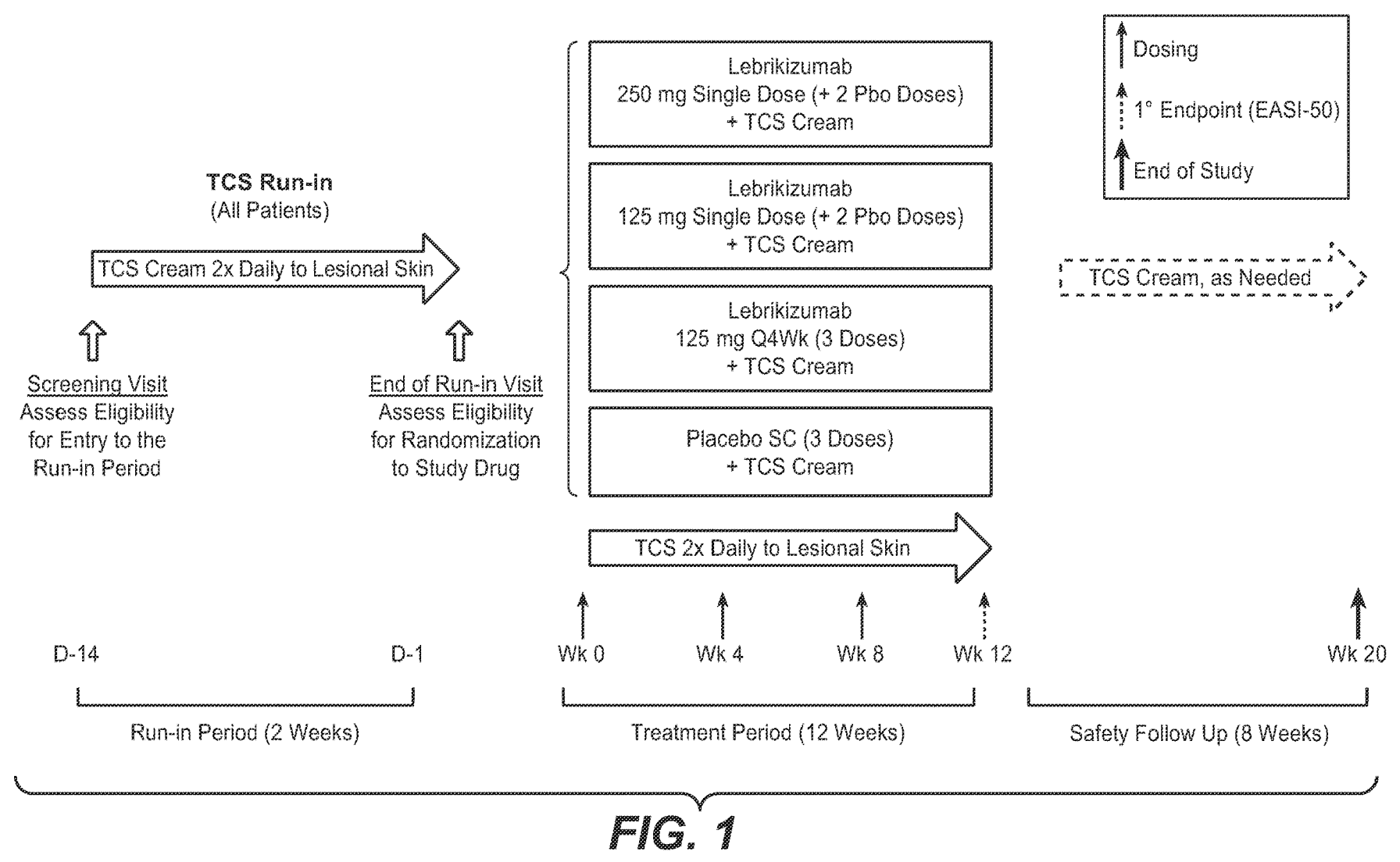

Dosing

1° Endpoint (EASI-50)

End of Study

TCS Cream, as Needed

Lebrikizumab
250 mg Single Dose (+ 2 Pbo Doses)
+ TCS Cream

Lebrikizumab
125 mg Single Dose (+ 2 Pbo Doses)
+ TCS Cream

Lebrikizumab
125 mg Q4Wk (3 Doses)
+ TCS Cream

Placebo SC (3 Doses)
+ TCS Cream

TCS 2x Daily to Lesional Skin

TCS Run-in
(All Patients)

TCS Cream 2x Daily to Lesional Skin

End of Run-in Visit
Assess Eligibility
for Randomization
to Study Drug

Screening Visit
Assess Eligibility
for Entry to the
Run-in Period

Wk 0     Wk 4     Wk 8     Wk 12     Wk 20

D-1

D-14

Run-in Period (2 Weeks)

Treatment Period (12 Weeks)

Safety Follow Up (8 Weeks)

*FIG. 1*

USES OF IL-13 ANTAGONISTS FOR TREATING ATOPIC DERMATITIS

CROSS REFERENCE TO RELATED APPLICATIONS

This application is a continuation of U.S. patent application Ser. No. 16/356,309, filed Mar. 18, 2019, now U.S. Pat. No. 11,434,286 granted Sep. 6, 2022, which is a continuation of International Application No. PCT/US2017/052891 having an International Filing Date of Sep. 22, 2017, which claims the benefit of provisional U.S. Application No. 62/539,037, filed Jul. 31, 2017, provisional U.S. Application No. 62/530,683, filed Jul. 10, 2017, provisional U.S. Application No. 62/527,204, filed Jun. 30, 2017, and provisional U.S. Application No. 62/398,713, filed Sep. 23, 2016 all of which are hereby incorporated by reference in their entirety.

SEQUENCE LISTING

The instant application contains a Sequence Listing which is in ST.26 XML format and is hereby incorporated by reference in its entirety. Said Sequence Listing, created on Aug. 8, 2022, is named "X22689A_SequenceListing" and is 17,647 bytes in size.

FIELD

Uses of IL-13 antagonists for treating atopic dermatitis are provided. Also provided are methods of treating atopic dermatitis and methods of reducing the severity of atopic dermatitis by administering IL-13 antagonists.

BACKGROUND

Atopic dermatitis (AD) is a chronic relapsing and remitting inflammatory skin disorder affecting all age groups. Clinically, AD is characterized by xerosis, erythematous crusting rash, lichenification, an impaired skin barrier, and intense pruritus (Bieber T., N Engl J Med 2008; 358:1483-94).

Patients with AD have a high disease burden, and their quality of life (QoL) is significantly impacted. In one study, AD was shown to have a greater negative effect on patient mental health than diabetes and hypertension (Zuberbier T, et al., J Allergy Clin Immunol 2006; 118:226-32). Patients with moderate to severe AD have a higher prevalence of social dysfunction and sleep impairment, which is directly related to severity of disease (Williams H, et al., J Allergy Clin Immunol 2008; 121:947-54. e15). Depression, anxiety, and social dysfunction not only affect patients with AD but also their caregivers (Zuberbier T, et al., J Allergy Clin Immunol 2006; 118:226-32). Compared with psoriasis, another common and debilitating skin disease, AD patients have lower role-physical, vitality, social functioning, role-emotional, and mental health subscale scores (Kiebert G, et al., Int J Dermatol 2002; 41:151-8).

Interleukin (IL)-13 is considered a key mediator of T-helper type 2 (Th2) inflammation and elevated levels of IL-13 have been associated not only with atopic dermatitis but with numerous other diseases including, but not limited to, asthma, inflammatory bowel disease, idiopathic pulmonary fibrosis (IPF), and chronic obstructive pulmonary disease (COPD) (Oh C K, et al., Eur Respir Rev 19:46-54 (2010); Fahy J V, et al., Nat Rev Immunol 15:57-65 [2015]). IL-13 is produced by many cell types, including Th2 cells, basophils, eosinophils, and mast cells, as well as airway epithelial cells and Type 2 innate lymphoid cells. IL-13 binds to a heterodimeric receptor, IL-4Rα/IL-13Rα1 that is shared with IL-4 and activates the STAT-6 signaling pathway (Hershey G K, J Allergy Clin Immunol 111(4):677-90 [2003]). Because Th2 inflammation involves the activity of several cell types in addition to Th2 cells, including Type 2 innate lymphoid cells (ILC2s), "Th2 inflammation" has more recently been referred to in the scientific literature as "Type 2 inflammation." In addition to Th2 cells, ILC2s have been identified as important sources of cytokines such as IL-5 and IL-13. Accordingly, cytokines such as IL-13 and IL-5 that have been previously identified as Th2 cytokines are now also referred to as Type 2 cytokines in the scientific literature. Likewise, the disease states associated with such cytokines, including atopic dermatitis, are now also referred to as Type 2-driven diseases or Type 2-associated diseases. See, e.g., Noonan et al., J. Allergy Clin Immunol., 132(3): 567-574 (2013); Hanania et al., Thorax 70(8): 748-56 (2015); and Cai et al., Bioanalysis 8(4): 323-332 (2016).

Eosinophilic inflammation is associated with a variety of illnesses, both allergic and non-allergic (Gonlugur (2006) Immunol. Invest. 35(1):29-45). Inflammation is a restorative response of living tissues to injury. A characteristic of inflammatory reactions is the accumulation of leukocytes in injured tissue due to certain chemicals produced in the tissue itself. Eosinophil leukocytes accumulate in a wide variety of conditions such as allergic disorders, helminthic infections, and neoplastic diseases (Kudlacz et al., (2002) Inflammation 26: 111-119). Eosinophil leukocytes, a component of the immune system, are defensive elements of mucosal surfaces. They respond not only to antigens but to parasites, chemicals, and trauma.

Tissue eosinophilia occurs in skin diseases such as eczema, pemphigus, acute urticaria, and toxic epidermal necrolysis as well as in atopic dermatitis (Rzany et al., Br. J. Dermatol. 135: 6-11 (1996)). Eosinophils accumulate in the tissue and empty granule proteins in IgE-mediated allergic skin reactions (Nielsen et al., Ann. Allergy Asthma Immunol., 85: 489-494 (2001)). Eosinophils combined with mast cells are likely to cause joint inflammation (Miossec, J. Clin. Rheumatol. 3: 81-83 (1997)). Eosinophilic inflammation sometimes accompanies joint trauma. Synovial fluid eosinophilia can be associated with diseases such as rheumatoid arthritis, parasitic disease, hypereosinophilic syndrome, Lyme disease, and allergic processes, as well as hemarthrosis and arthrography (Atanes et al., Scand. J. Rheumatol., 25: 183-185 (1996)). Eosinophilic inflammation can affect bones as well (Yetiser et al., Int. J. Pediatr. Otorhinolaryngol., 62: 169-173 (2002)). Examples of eosinophilic muscle disease include eosinophilic perimyositis, eosinophilic polymyositis, and focal eosinophilic myositis (Lakhanpal et al., Semin. Arthritis Rheum., 17: 331-231 (1988)). Eosinophilic inflammations affecting skeletal muscles may be associated with parasite infections or drugs or features of some systemic disorders of hypereosinophilia (e.g., idiopathic hypereosinophilic syndrome and eosinophilia-myalgia syndrome. Eosinophils participate in the inflammatory response to epitopes recognized by autoimmune antibodies (Engineer et al., Cytokine, 13: 32-38 (2001)). Connective tissue diseases may lead to neutrophilic, eosinophilic, or lymphocytic vascular inflammations (Chen et al., J. Am. Acad. Dermatol., 35: 173-182 (1996)). Tissue and peripheral blood eosinophilia can occur in active rheumatismal diseases. Elevation of serum ECP levels in ankylosing spondylitis, a kind of connective tissue disease, suggests that eosinophils are also involved in the underlying process (Feltelius et al., Ann. Rheum. Dis., 46: 403-407

(1987)). Wegener's granulomatosis can rarely present with pulmonary nodules, pleural effusion, and peripheral blood eosinophilia (Krupsky et al., Chest, 104: 1290-1292 (1993)).

Peripheral blood eosinophilia of at least 400/mm3 can occur in 7% of cases of systemic sclerosis, 31% of cases of localized scleroderma, and 61% of cases of eosinophilic fasciitis (Falanga, et al., J. Am. Acad. Dermatol., 17: 648-656 (1987)). Scleroderma yields an inflammatory process closely resembling Meissner's and Auerbach's plexuses and consists of mast cells and eosinophil leukocytes in the gastrointestinal system. Eosinophil-derived neurotoxins can contribute to gastrointestinal motor dysfunction, as occurs in scleroderma (DeSchryver-Kecskemeti, et al. Arch. Pathol. Lab Med., 113: 394-398 (1989)).

Eosinophils can accompany localized (Varga, et al., Curr. Opin. Rheumatol., 9: 562-570 (1997)) or systemic (Bouros et al., Am. J. Respir. Crit. Care Med., 165: 1581-1586 (2002)) connective tissue proliferation. They can incite fibrosis by inhibiting proteoglycan degradation in fibroblasts (Hernnas et al., Eur. J. Cell Biol., 59: 352-363 (1992)), and fibroblasts mediate eosinophil survival by secreting GM-CSF (Vancheri et al., Am. J. Respir. Cell Mol. Biol., 1: 289-214 (1989)). Eosinophils can be found in nasal (Bacherct et al., J. allergy Clin. Immunol., 107: 607-614 (2001)), bronchial (Arguelles, et al., Arch. Intern. Med., 143: 570-571 (1983)), and gastrointestinal polyp tissues (Assarian, et al., Hum. Pathol., 16: 311-312 (1985)). Likewise, eosinophils can be localized in inflammatory pseudotumors (myofibroblastic tumor). Eosinophils often accompany inflammatory pseudotumors in the orbital region, in which case the condition can mimic angioedema or allergic rhino-conjunctivitis (Li et al., Ann. Allergy, 69: 101-105 (1992)).

Eosinophilic inflammation can be found in tissue trauma (e.g., as a result of surgery or injury). Eosinophilic inflammation can also be associated with cardiovascular illnesses (e.g., eosinophilic myocarditis, eosinophilic coronary arteritis, ischemic heart disease, acute myocardial infarction, cardiac rupture). Necrotic inflammatory processes can also involve eosinophilic inflammation (polymyositis, coronary artery dissection, necrotizing lesions of neuro-Behcet's disease, dementia, cerebral infarction).

Several lines of evidence suggest that IL-13 is a key pathogenetic component in atopic dermatitis (AD). Increased expression of IL-13 has consistently been reported in AD skin (Hamid Q, et al., J Allergy Clin Immunol 98:225-31 [1996]; Jeong C W, et al., Clin Exp Allergy 33:1717-24 [2003]; Tazawa T, et al., Arch Dermatol Res 295:459-64 [2004]; Neis M M, et al., J Allergy Clin Immunol 118:930-7 [2006]; Suárez-Fariñas M, et al., J Allergy Clin Immunol 132:361-70 [2013]; Choy D F, et al., J Allergy Clin Immunol 130:1335-43 [2012]) and some reports suggest a relationship between IL-13 expression and the severity of disease (La Grutta S, et al., Allergy 60:391-5 [2005]). Increased IL-13 has also been reported in the serum of AD patients (Novak N, et al., J Invest Dermatol 2002; 119:870-5; International Patent Application No. PCT/US2016/022481 [publication no. WO2016149276]), and several studies have reported an increase in IL-13-expressing T cells in the blood of AD patients (Akdis M, et al., J Immunol 1997; 159:4611-9; Aleksza M, et al., Br J Dermatol 2002; 147:1135-41; La Grutta S, et al., Allergy 2005; 60:391-5). IL-13 and its receptors have therefore become therapeutic targets for the treatment of various Type 2 inflammation-associated diseases including asthma, IPF and AD (Corren J, et al., N Eng J Med 365:1088-98 [2011]; Scheerens H, et al., Clin Exp Allergy 44:38-46 [2014]; Beck L A, et al., N Eng J Med 371:130-9 [2014]; Thaci D, et al., Lancet 2016;

387:40-52). Additional publications that discuss IL-13 in atopic dermatitis or lebrikizumab include He J Q, et al., Genes Immun 2003; 4:385-89; Kim B E, et al. Clin Immunology 2008; 126, 332-7; Bhogal R K & Bona C A Int Rev Immunol 2008; 27:472-96; Kim S T, et al. J Gene Med 2009; 11:26-37; Bieber T, et al. J Allergy Clin Immunol 2014; 133: AB404; Thaci D, et al. J Allergy Clin Immunol 2014; 133: AB192; 2. Ultsch M, et al. J Mol Biol 2013; 425:1330-1339.

In addition, several clinical studies investigating agents with broadly acting anti-inflammatory activity have demonstrated a reduction in IL-13 expression that was associated with improved clinical disease. For example, nineteen adult patients with moderate to severe AD treated for 12 weeks with cyclosporin A showed a reduction in skin expression of IL-13 (Khattri S, et al., J Allergy Clin Immunol 2014; 133(6):1626-34), ten pediatric patients treated with cyclosporin A micro-emulsion showed a reduction in blood IL-13 expressing CD3$^+$ T cells (Bunikowski R, et al., Pediatr Allergy Immunol 2001; 12:216-23), and twelve adults with moderate to severe AD treated with narrow-band ultraviolet B showed a significant decrease in IL-13 skin expression (Tintle S, et al., J Allergy Clin Immunol 2011; 128:583-93. e1-4).

A number of IL-13 antagonists have been described and clinically tested in various Type 2 inflammation-associated diseases including asthma, COPD, and IPF. These include IMA-026, IMA-638 (also referred to as, anrukinzumab, INN No. 910649-32-0; QAX-576); tralokinumab (also referred to as CAT-354, CAS No. 1044515-88-9); and AER-001, ABT-308 (also referred to as humanized 13C5.5 antibody). In addition, certain IL-4receptor alpha antagonists have been developed and these are antagonists of both IL-13 and IL-4. Examples of IL-4receptor alpha antagonists include AMG-317, AIR-645, dupilumab, which has been tested clinically in atopic dermatitis as well as asthma (see, e.g., Beck L A, et al., N Eng J Med 371:130-9 [2014]) and AER-001, IL4/IL-13 trap. Another IL-13 antagonist is lebrikizumab. Lebrikizumab is a humanized monoclonal immunoglobulin (Ig) G4 antibody (huIgG4) with a mutation in the hinge region for increased stability. Lebrikizumab binds specifically to soluble human IL-13 with high affinity and neutralizes its functional activities with high potency. Lebrikizumab inhibits IL-13 signaling through the IL-4Ralpha/IL-13Ralpha1 receptor. It blocks the binding of IL-13 to IL-4Ralpha, but does not block the binding of IL-13 to IL-13Ralpha1 or IL-13Ralpha2. Lebrikizumab has been described in various publications and tested in several asthma studies (see, e.g., Corren et al. (2011) N Engl J Med 365: 1088-98; Scheerens et al. (2012) Am J Respir Crit Care Med 185: A3960; Jia et al. (2012) J Allergy Clin Immunol 130: 647-654 e10; Hanania et al., Thorax 2015; 70:748-756; Hanania et al., Lancet Respir Med 2016, available at dx(dot)doi(dot)org(slash)S2213-2600(16)30265-X, published online Sep. 5, 2016; WO 2012/083132).

The therapeutic approach to AD primarily consists of trigger avoidance, skin hydration with bathing and use of emollients and anti-inflammatory therapies consisting predominantly of topical corticosteroids (TCS). In many patients, treatment with TCS provides some measure of symptomatic relief but does not adequately control their disease. In addition, TCS use is associated with many comorbidities and limitations including high patient burden. Review of literature (including PubMed, the Nankervis systematic review, the Global Resource for Eczema Trials [GREAT] database) of randomized, controlled, blinded clinical trials of systemic immunosuppressant treatments and oral glucocorticoids for treatment of moderate-to-severe AD highlights that the use of conventional systemic immunosuppressant treatments is often limited by significant side effects; additionally, their use is mainly off-label. These findings indicate a substantial unmet need and the importance of developing drugs targeting the underlying AD specific pathways, such as the recently approved anti-IL-4Rα antibody dupilumab. The promise for biological therapy in refractory AD is to provide more effective therapy that reduces the need for systemic immunosuppressive therapy and ultimately reduces the need for intensive TCS therapy. While dupilumab is the first and only biologic approved for the treatment of adults with moderate-to-severe AD, it is administered as an initial dose of 600 mg (two 300 mg subcutaneous injections), followed by 300 mg every other week (Simpson et al., N Engl J Med. 2016; 375(24): 2335-2348).

In those patients who have persistent moderate-to-severe disease not responding adequately to TCS, recent guidelines outline a number of step-up therapeutic options (Ring J, et al., J Eur Acad Dermatol Venereol 2012; 26:1176-93; Schneider L, et. al., J Allergy Clin Immunol 2013; 131:295-9. e1-27). The step-up options include topical calcineurin inhibitors (TCIs), phototherapy, and immunosuppressive agents such as oral corticosteroids, cyclosporine, azathioprine, methotrexate, and mycophenolate. Amongst these, only cyclosporine is approved for treatment of moderate to severe AD (nationally licensed in many European countries, but not in the U.S.), and its use is limited to patients aged 16 years and over (for a maximum of 8 weeks [NEORAL®]). Though cyclosporine is the most extensively studied systemic agent, interpretation of the trial results and applicability to clinical practice is limited by the trial designs (Schmitt J, et al., J Eur Acad Dermatol Venereol 2007; 21:606-619). Studies of other immunosuppressant agents such azathioprine and methotrexate consist mostly of case reports, with few reported randomized controlled trials (Haeck I M, et al., J Am Acad Dermatol 2011; 64:1074-84; Schram M E, et al., J Allergy Clin Immunol 2011; 128:353-9). Prescribing practice demonstrates significant country-specific variation, highlighted by a recent survey of European dermatologists' which reported no clearly favored agent: 43% used cyclosporine, 31% oral corticosteroids, and 22% azathioprine (Proudfoot L E, et al., Br J Dermatol 2013; 169:901-9).

Although the step-up therapies, including systemic immunosuppressants, used to treat patients with moderate to severe AD show evidence of modest to good efficacy, poor tolerability due to side effects limit their prolonged use. Even in cases where cyclosporine has demonstrated substantial efficacy, approximately 50% of patients relapse within 2 weeks, and 80% relapse within 6 weeks after cessation of therapy (Amor K T, et al., J Am Acad Dermatol 2010; 63:925-46). The continued use of these agents despite harmful side effects and limitations indicates a high unmet medical need for safer and more effective therapies.

In attempts to find novel therapies for moderate to severe AD with an acceptable benefit-risk profile, a number of biologic agents that specifically target inflammatory cells and mediators have been tested (Taïeb A, et al., J Dtsch Dermatol Ges 2012; 10:174-8; Guttman-Yassky E, et al., Expert Opin Biol Ther 2013; 13:549-61). However, several of these studies and case reports were performed in only a small number of patients (as few as one or two) and have shown inconsistent efficacy and/or safety signals.

Accordingly, there is a need for new therapeutic treatments and treatment regimens that will reduce the severity of atopic dermatitis disease symptoms and maximize efficacy. In addition, there is a need for new therapeutic treatments and treatment regimens that provide an improved safety profile with limited toxicity compared to existing treatments or provide more tolerability or convenience for patients thereby improving patient compliance with usage of therapeutic agents and adherence to treatment regimens.

The invention described herein meets certain of the above-described needs and provides other benefits.

All references cited herein, including patent applications and publications, are incorporated by reference in their entirety for any purpose.

SUMMARY

The invention is based, at least in part, on the surprising and unexpected discovery that an anti-IL-13 antagonist monoclonal antibody, lebrikizumab, provides therapeutic benefit when administered to atopic dermatitis patients using the dosing regimens provided herein, including patients using topical corticosteroids concomitantly, as assessed by several efficacy outcome measures. Accordingly, provided herein are uses of IL-13 antagonists, including anti-IL-13 antibodies such as lebrikizumab, in treating atopic dermatitis and methods of treating atopic dermatitis with IL-13 antagonists, including anti-IL-13 antibodies such as lebrikizumab.

Accordingly, in one aspect, methods of treating atopic dermatitis in a patient comprising administering to the patient a pharmaceutical composition comprising a therapeutically effective amount of an IL-13 antagonist, wherein the pharmaceutical composition reduces disease severity in the patient and wherein disease severity is assessed by an Atopic Dermatitis Disease Severity Outcome Measure (ADDSOM) are provided. In some embodiments, the atopic dermatitis is moderate to severe as determined by Rajka/Langeland criteria score and wherein the Rajka/Langeland criteria score is determined to be between 4.5 and 9. In some embodiments, the method further comprises administration of one or more topical corticosteroids. In some embodiments, the one or more topical corticosteroids is administered before administration of the IL-13 antagonist, at the same time as administration of the IL-13 antagonist, or after administration of the IL-13 antagonist. In some embodiments, the one or more topical corticosteroids is selected from triamcinolone acetonide, hydrocortisone, and a combination of triamcinolone acetonide and hydrocortisone. In some embodiments, the patient is aged 12 years and over. In some embodiments, the patient is inadequately controlled on topical corticosteroids. In some embodiments, the IL-13 antagonist is a monoclonal anti-IL-13 antibody. In some embodiments, the anti-IL-13 antibody is an antibody comprising a VH comprising HVR-H1, HVR-H2, and HVR-H3, wherein the respective VH HVRs have the amino acid sequence of SEQ ID NO: 5, SEQ ID NO: 6, and SEQ ID NO: 7, and comprising a VL comprising HVR-L1, HVR-L2, and HVR-L3, wherein the respective VL HVRs have the amino acid sequence of SEQ ID NO: 8, SEQ ID NO: 9, and SEQ ID NO: 10. In certain embodiments, the anti-IL-13 antibody is an IgG1, IgG2, IgG3, or IgG4. In certain embodiments, the anti-IL-13 antibody is a human, humanized, or chimeric antibody. In some embodiments, the anti-IL-13 antibody is an antibody comprising a VH comprising a sequence selected from SEQ ID NO: 1 and SEQ ID NO: 3, and comprising a VL comprising a sequence selected from SEQ ID NO: 2 and SEQ ID NO: 4. In certain embodiments, the anti-IL-13 antibody is a full-length antibody or a fragment thereof that binds human IL-13. In some embodiments, the anti-IL-13 antibody is IgG4. In one embodiment, the anti-IL-13 antibody is lebrikizumab. In one embodiment, the anti-IL-13 antibody comprises a heavy chain having the amino acid sequence of SEQ ID NO: 11 and a light chain having the amino acid sequence of SEQ ID NO: 12. In some embodiments, the IL-13 antagonist is administered to the patient using a subcutaneous administration device. In certain such embodiments, the subcutaneous administration device is selected from a prefilled syringe, disposable pen injection device, microneedle device, microinfuser device, needle-free injection device, and autoinjector device. In one embodiment, the IL-13 antagonist is lebrikizumab and lebrikizumab is administered to the patient using a prefilled syringe. In one embodiment, the IL-13 antagonist is lebrikizumab and lebrikizumab is administered to the patient using an autoinjector device.

In another aspect, the pharmaceutical composition for use in treating atopic dermatitis comprises 125 mg or 250 mg or 500 mg or about 125 mg or about 250 mg or about 500 mg of an anti-IL-13 antibody. In some embodiments, the pharmaceutical composition comprises between 110 mg and 140 mg of an anti-IL-13 antibody or between 120 mg and 130 mg of an anti-IL-13 antibody. In some embodiments, the pharmaceutical composition comprises between 225 mg and 275 mg of an anti-IL-13 antibody or between 240 mg and 260 mg of an anti-IL-13 antibody. In some embodiments, the pharmaceutical composition comprises between 450 mg and 550 mg of an anti-IL-13 antibody or between 475 mg and 525 mg of an anti-IL-13 antibody or between 490 mg and 510 mg of an anti-IL-13 antibody. In some embodiments, the pharmaceutical composition comprises 125 mg, or about 125 mg, or between 110 mg and 140 mg, or between 120 mg and 130 mg, of the anti-IL-13 antibody and the composition is administered subcutaneously once every four weeks. In some embodiments, the pharmaceutical composition is administered for a period of 12 weeks or a period of 20 weeks or a period of 24 weeks. In some embodiments, the pharmaceutical composition comprises 250 mg, or about 250 mg, or between 225 mg and 275 mg, or between 240 mg and 260 mg of the anti-IL-13 antibody and the composition is administered subcutaneously once every four weeks or once every eight weeks. In some embodiments, the pharmaceutical composition is administered for a period of 24 weeks or more or for 24 weeks. In some embodiments, the atopic dermatitis is moderate to severe as determined by Rajka/Langeland criteria score and wherein the Rajka/Langeland criteria score is determined to be between 4.5 and 9. In some embodiments, the IL-13 antagonist is a monoclonal anti-IL-13 antibody. In some embodiments, the anti-IL-13 antibody is an antibody comprising a VH comprising HVR-H1, HVR-H2, and HVR-H3, wherein the respective VH HVRs have the amino acid sequence of SEQ ID NO: 5, SEQ ID NO: 6, and SEQ ID NO: 7, and comprising a VL comprising HVR-L1, HVR-L2, and HVR-L3, wherein the respective VL HVRs have the amino acid sequence of SEQ ID NO: 8, SEQ ID NO: 9, and SEQ ID NO: 10. In certain embodiments, the anti-IL-13 antibody is an IgG1, IgG2, IgG3, or IgG4. In certain embodiments, the anti-IL-13 antibody is a human, humanized, or chimeric antibody. In some embodiments, the anti-IL-13 antibody is an antibody comprising a VH comprising a sequence selected from SEQ ID NO: 1 and SEQ ID NO: 3, and comprising a VL comprising a sequence selected from SEQ ID NO: 2 and SEQ ID NO: 4. In certain embodiments, the anti-IL-13 antibody is a full-length antibody or a fragment thereof that binds human IL-13. In some embodiments, the anti-IL-13 antibody is IgG4. In one embodiment, the anti-IL-13 antibody is lebrikizumab. In one embodiment, the anti-IL-13 antibody comprises a heavy chain having the amino acid sequence of SEQ ID NO: 11 and a light chain having the amino acid sequence of SEQ ID NO: 12. In some embodiments, the IL-13 antagonist is administered to the patient using a subcutaneous administration device. In certain such embodiments, the subcutaneous administration device is selected from a prefilled syringe, disposable pen injection device, microneedle device, microinfuser device, needle-free injection device, and autoinjector device. In one embodiment, the IL-13 antagonist is lebrikizumab and lebrikizumab is administered to the patient using a prefilled syringe. In one embodiment, the IL-13 antagonist is lebrikizumab and lebrikizumab is administered to the patient using an autoinjector device. In some embodiments, the method further comprises administration of one or more topical corticosteroids. In some embodiments, the one or more topical corticosteroids is administered before administration of the IL-13 antagonist, at the same time as administration of the IL-13 antagonist, or after administration of the IL-13 antagonist. In some embodiments, the one or more topical corticosteroids is selected from triamcinolone acetonide, hydrocortisone, and a combination of triamcinolone acetonide and hydrocortisone. In some embodiments, the patient is aged 12 years and over. In some embodiments, the patient is inadequately controlled on topical corticosteroids.

In yet another aspect, methods of treating atopic dermatitis in a patient comprising administering to the patient a pharmaceutical composition comprising a therapeutically effective amount of an IL-13 antagonist, wherein the pharmaceutical composition reduces disease severity in the patient and wherein disease severity is assessed by an Atopic Dermatitis Disease Severity Outcome Measure (ADDSOM) are provided, and wherein the Atopic Dermatitis Disease Severity Outcome Measure is Eczema Area and Severity Index (EASI), or Severity Scoring of Atopic Dermatitis (SCORAD), or Investigator Global Assessment (IGA), or a Patient Reported Outcome (PRO). In some embodiments, the atopic dermatitis is moderate to severe as determined by Rajka/Langeland criteria score and wherein the Rajka/Langeland criteria score is determined to be between 4.5 and 9. In some embodiments, the method further comprises administration of one or more topical corticosteroids. In some embodiments, the one or more topical corticosteroids is administered before administration of the IL-13 antagonist, at the same time as administration of the IL-13 antagonist, or after administration of the IL-13 antagonist. In some embodiments, the one or more topical corticosteroids is selected from triamcinolone acetonide, hydrocortisone, and a combination of triamcinolone acetonide and hydrocortisone. In some embodiments, the patient is aged 12 years and over. In some embodiments, the patient is inadequately controlled on topical corticosteroids. In some embodiments, the ADDSOM is EASI and the pharmaceutical composition reduces the EASI by 50% or 75% or 90% compared to the EASI determined prior to administration of a first dose of the pharmaceutical composition. In some embodiments, the EASI is determined 12 weeks after administration of the first dose or 20 weeks after administration of the first dose or 24 weeks after administration of the first dose. In some embodiments, the ADDSOM is SCORAD and the pharmaceutical composition reduces the SCORAD by 50% compared to the SCORAD determined prior to administration of a first dose of the pharmaceutical composition. In some embodiments, the ADDSOM is SCORAD and the pharmaceutical composition reduces the SCORAD by 75% compared to the SCORAD determined prior to administration of a first dose of the pharmaceutical composition. In some embodiments, the SCORAD is determined 12 weeks after administration of the first dose. In some embodiments, the ADDSOM is IGA and the pharmaceutical composition reduces the IGA to zero or one. In some embodiments, the IGA is determined 12 weeks after administration of a first dose of the pharmaceutical composition. In some embodiments, the ADDSOM is PRO and the PRO is pruritus visual analogue scale (VAS), sleep loss VAS, or Atopic Dermatitis Impact Questionnaire (ADIQ) score. In some embodiments, the PRO is determined 12 weeks after administration of a first dose of the pharmaceutical composition. In some embodiments, the PRO is pruritus VAS and the pharmaceutical composition reduces the pruritus VAS by 40% to 55%. In some embodiments, the PRO is sleep loss VAS and the pharmaceutical composition reduces the sleep loss VAS by 53% to 61%. In some embodiments, the PRO is ADIQ and the pharmaceutical composition reduces the ADIQ score by 54% to 65%. In some embodiments, the IL-13 antagonist is a monoclonal anti-IL-13 antibody. In some embodiments, the anti-IL-13 antibody is an antibody comprising a VH comprising HVR-H1, HVR-H2, and HVR-H3, wherein the respective VH HVRs have the amino acid sequence of SEQ ID NO: 5, SEQ ID NO: 6, and SEQ ID NO: 7, and comprising a VL comprising HVR-L1, HVR-L2, and HVR-L3, wherein the respective VL HVRs have the amino acid sequence of SEQ ID NO: 8, SEQ ID NO: 9, and SEQ ID NO: 10. In certain embodiments, the anti-IL-13 antibody is an IgG1, IgG2, IgG3, or IgG4. In certain embodiments, the anti-IL-13 antibody is a human, humanized, or chimeric antibody. In some embodiments, the anti-IL-13 antibody is an antibody comprising a VH comprising a sequence selected from SEQ ID NO: 1 and SEQ ID NO: 3, and comprising a VL comprising a sequence selected from SEQ ID NO: 2 and SEQ ID NO: 4. In certain embodiments, the anti-IL-13 antibody is a full-length antibody or a fragment thereof that binds human IL-13. In some embodiments, the anti-IL-13 antibody is IgG4. In one embodiment, the anti-IL-13 antibody is lebrikizumab. In one embodiment, the anti-IL-13 antibody comprises a heavy chain having the amino acid sequence of SEQ ID NO: 11 and a light chain having the amino acid sequence of SEQ ID NO: 12. In some embodiments, the IL-13 antagonist is administered to the patient using a subcutaneous administration device. In certain such embodiments, the subcutaneous administration device is selected from a prefilled syringe, disposable pen injection device, microneedle device, microinfuser device, needle-free injection device, and autoinjector device. In one embodiment, the IL-13 antagonist is lebrikizumab and lebrikizumab is administered to the patient using a prefilled syringe. In one embodiment, the IL-13 antagonist is lebrikizumab and lebrikizumab is administered to the patient using an autoinjector device.

In still yet another aspect, methods comprising administering to a patient a therapeutically effective amount of an IL-13 antagonist, wherein the therapeutically effective amount is selected from 125 mg and 250 mg and wherein the IL-13 antagonist is administered subcutaneously once every four weeks are provided. In some embodiments, the therapeutically effective amount is about 125 mg or between 110 mg and 140 mg of an anti-IL-13 antibody or between 120 mg and 130 mg of an anti-IL-13 antibody. In some embodiments, the therapeutically effective amount is about 250 mg or between 225 mg and 275 mg of an anti-IL-13 antibody or between 240 mg and 260 mg of an anti-IL-13 antibody. In some embodiments, the IL-13 antagonist is a monoclonal anti-IL-13 antibody. In some embodiments, the anti-IL-13 antibody is an antibody comprising a VH comprising HVR- H1, HVR-H2, and HVR-H3, wherein the respective VH HVRs have the amino acid sequence of SEQ ID NO: 5, SEQ ID NO: 6, and SEQ ID NO: 7, and comprising a VL comprising HVR-L1, HVR-L2, and HVR-L3, wherein the respective VL HVRs have the amino acid sequence of SEQ ID NO: 8, SEQ ID NO: 9, and SEQ ID NO: 10. In certain embodiments, the anti-IL-13 antibody is an IgG1, IgG2, IgG3, or IgG4. In certain embodiments, the anti-IL-13 antibody is a human, humanized, or chimeric antibody. In some embodiments, the anti-IL-13 antibody is an antibody comprising a VH comprising a sequence selected from SEQ ID NO: 1 and SEQ ID NO: 3, and comprising a VL comprising a sequence selected from SEQ ID NO: 2 and SEQ ID NO: 4. In certain embodiments, the anti-IL-13 antibody is a full-length antibody or a fragment thereof that binds human IL-13. In some embodiments, the anti-IL-13 antibody is IgG4. In one embodiment, the anti-IL-13 antibody is lebrikizumab. In one embodiment, the anti-IL-13 antibody comprises a heavy chain having the amino acid sequence of SEQ ID NO: 11 and a light chain having the amino acid sequence of SEQ ID NO: 12. In some embodiments, the IL-13 antagonist is administered to the patient using a subcutaneous administration device. In certain such embodiments, the subcutaneous administration device is selected from a prefilled syringe, disposable pen injection device, microneedle device, microinfuser device, needle-free injection device, and autoinjector device. In one embodiment, the IL-13 antagonist is lebrikizumab and lebrikizumab is administered to the patient using a prefilled syringe. In one embodiment, the IL-13 antagonist is lebrikizumab and lebrikizumab is administered to the patient using an autoinjector device. In some embodiments, the atopic dermatitis is moderate to severe as determined by Rajka/Langeland criteria score and wherein the Rajka/Langeland criteria score is determined to be between 4.5 and 9. In some embodiments, the method further comprises administration of one or more topical corticosteroids. In some embodiments, the one or more topical corticosteroids is administered before administration of the IL-13 antagonist, at the same time as administration of the IL-13 antagonist, or after administration of the IL-13 antagonist. In some embodiments, the one or more topical corticosteroids is selected from triamcinolone acetonide, hydrocortisone, and a combination of triamcinolone acetonide and hydrocortisone. In some embodiments, the patient is aged 12 years and over. In some embodiments, the patient is inadequately controlled on topical corticosteroids. In some embodiments, the therapeutically effective amount reduces disease severity in the patient and disease severity is assessed by an Atopic Dermatitis Disease Severity Outcome Measure (ADDSOM). In some embodiments, the ADDSOM is Eczema Area and Severity Index (EASI), or Severity Scoring of Atopic Dermatitis (SCORAD), or Investigator Global Assessment (IGA), or a Patient Reported Outcome (PRO). In some embodiments, the ADDSOM is EASI and the therapeutically effective amount reduces the EASI by 50% or 75% or 90% compared to the EASI determined prior to administration of a first dose of the IL-13 antagonist. In some embodiments, the EASI is determined 12 weeks after administration of the first dose or 20 weeks after administration of the first dose or 24 weeks after administration of the first dose. In some embodiments, the ADDSOM is SCORAD and the therapeutically effective amount reduces the SCORAD by 50% compared to the SCORAD determined prior to administration of a first dose of the IL-13 antagonist. In some embodiments, the ADDSOM is SCORAD and the therapeutically effective amount reduces the SCORAD by 75% compared to the SCORAD determined prior to administration of a first dose of the IL-13 antagonist. In some embodiments, the SCORAD is determined 12 weeks after administration of the first dose. In some embodiments, the ADDSOM is IGA and the therapeutically effective amount reduces the IGA to zero or one. In some embodiments, the IGA is determined 12 weeks after administration of a first dose of the IL-13 antagonist. In some embodiments, the ADDSOM is PRO and the PRO is pruritus visual analogue scale (VAS), sleep loss VAS, or Atopic Dermatitis Impact Questionnaire (ADIQ) score. In some embodiments, the PRO is determined 12 weeks after administration of a first dose of the IL-13 antagonist. In some embodiments, the PRO is pruritus VAS and the therapeutically effective amount reduces the pruritus VAS by 40% to 55%. In some embodiments, the PRO is sleep loss VAS and the therapeutically effective amount reduces the sleep loss VAS by 53% to 61%. In some embodiments, the PRO is ADIQ and the therapeutically effective amount reduces the ADIQ score by 54% to 65%.

In another aspect, methods of treating atopic dermatitis in a patient by administering to the patient a therapeutically effective amount of an IL-13 antagonist, where the administration comprises administration of at least one loading dose and administration of at least one subsequent maintenance dose, and where each of the at least one loading dose and each of the at least one maintenance dose is administered subcutaneously at a flat dose are provided. In some embodiments, the atopic dermatitis is moderate to severe as determined by Rajka/Langeland criteria score and wherein the Rajka/Langeland criteria score is determined to be between 4.5 and 9. In some embodiments, the method further comprises administration of one or more topical corticosteroids. In some embodiments, the one or more topical corticosteroids is administered before administration of the IL-13 antagonist, at the same time as administration of the IL-13 antagonist, or after administration of the IL-13 antagonist. In some embodiments, the one or more topical corticosteroids is selected from triamcinolone acetonide, hydrocortisone, and a combination of triamcinolone acetonide and hydrocortisone. In some embodiments, the patient is aged 12 years and over. In some embodiments, the patient is inadequately controlled on topical corticosteroids. In some embodiments, the IL-13 antagonist is a monoclonal anti-IL-13 antibody. In some embodiments, the anti-IL-13 antibody is an antibody comprising a VH comprising HVR-H1, HVR-H2, and HVR-H3, wherein the respective VH HVRs have the amino acid sequence of SEQ ID NO: 5, SEQ ID NO: 6, and SEQ ID NO: 7, and comprising a VL comprising HVR-L1, HVR-L2, and HVR-L3, wherein the respective VL HVRs have the amino acid sequence of SEQ ID NO: 8, SEQ ID NO: 9, and SEQ ID NO: 10. In certain embodiments, the anti-IL-13 antibody is an IgG1, IgG2, IgG3, or IgG4. In certain embodiments, the anti-IL-13 antibody is a human, humanized, or chimeric antibody. In some embodiments, the anti-IL-13 antibody is an antibody comprising a VH comprising a sequence selected from SEQ ID NO: 1 and SEQ ID NO: 3, and comprising a VL comprising a sequence selected from SEQ ID NO: 2 and SEQ ID NO: 4. In certain embodiments, the anti-IL-13 antibody is a full-length antibody or a fragment thereof that binds human IL-13. In some embodiments, the anti-IL-13 antibody is IgG4. In one embodiment, the anti-IL-13 antibody is lebrikizumab. In one embodiment, the anti-IL-13 antibody comprises a heavy chain having the amino acid sequence of SEQ ID NO: 11 and a light chain having the amino acid sequence of SEQ ID NO: 12. In some embodiments, the loading dose is 250 mg or 500 mg and the maintenance dose is 125 mg. In some embodiments, the loading dose is 250 mg and the maintenance dose is 125 mg. In some embodiments, the loading dose is 500 mg and the maintenance dose is 125 mg. In some embodiments, the maintenance dose is administered four weeks after administration of the loading dose and the maintenance dose is administered and once every four weeks thereafter for the duration of treatment. In some embodiments, the loading dose is 250 mg and the maintenance dose is 125 mg, where the maintenance dose is administered four weeks after the loading dose and once every four weeks thereafter for the duration of treatment. In some embodiments, the loading dose is 250 mg and the loading dose is administered followed by a second loading dose administration 15 days later and the maintenance dose is 125 mg. In some embodiments, the maintenance dose is administered two weeks after administration of the second loading dose and the maintenance dose is administered once every four weeks thereafter for the duration of treatment. In some embodiments, the loading dose is 250 mg and the loading dose is administered followed by a second loading dose administration 29 days later and the maintenance dose is 125 mg. In some embodiments, the maintenance dose is administered four weeks after administration of the second loading dose and the maintenance dose is administered once every four weeks thereafter for the duration of treatment. In some embodiments, the loading dose is 500 mg and the maintenance dose is 250 mg. In some embodiments, the maintenance dose is administered four weeks after administration of the loading dose and the maintenance dose is administered once every four weeks thereafter for the duration of treatment. In some embodiments, the maintenance dose is administered four weeks after administration of the loading dose and the maintenance dose is administered once every eight weeks thereafter for the duration of treatment. In some embodiments, the loading dose is 500 mg and the maintenance dose is 250 mg, where the maintenance dose is administered four weeks after the loading dose and once every four weeks thereafter for the duration of treatment. In some embodiments, the duration of treatment is 24 weeks or more. In some embodiments, the duration of treatment is 24 weeks. In some embodiments, the therapeutically effective amount reduces disease severity in the patient and disease severity is assessed by an Atopic Dermatitis Disease Severity Outcome Measure (ADDSOM). In some embodiments, the ADDSOM is Eczema Area and Severity Index (EASI), or Severity Scoring of Atopic Dermatitis (SCORAD), or Investigator Global Assessment (IGA), or a Patient Reported Outcome (PRO). In some embodiments, the ADDSOM is EASI and the therapeutically effective amount reduces the EASI by 50% or 75% or 90% compared to the EASI determined prior to administration of a first dose of the IL-13 antagonist. In some embodiments, the EASI is determined 12 weeks after administration of the first dose or 20 weeks after administration of the first dose or 24 weeks after administration of the first dose. In some embodiments, the ADDSOM is SCORAD and the therapeutically effective amount reduces the SCORAD by 50% compared to the SCORAD determined prior to administration of a first dose of the IL-13 antagonist. In some embodiments, the ADDSOM is SCORAD and the therapeutically effective amount reduces the SCORAD by 75% compared to the SCORAD determined prior to administration of a first dose of the IL-13 antagonist. In some embodiments, the SCORAD is determined 12 weeks after administration of the first dose. In some embodiments, the ADDSOM is IGA and the therapeutically effective amount reduces the IGA to zero or one. In some embodiments, the IGA is determined 12 weeks after administration of a first dose of the IL-13 antagonist. In some embodiments, the ADDSOM is PRO and the PRO is pruritus visual analogue scale (VAS), sleep loss VAS, or Atopic Dermatitis Impact Questionnaire (ADIQ) score. In some embodiments, the PRO is determined 12 weeks after administration of a first dose of the IL-13 antagonist. In some embodiments, the PRO is pruritus VAS and the therapeutically effective amount reduces the pruritus VAS by 40% to 55%. In some embodiments, the PRO is sleep loss VAS and the therapeutically effective amount reduces the sleep loss VAS by 53% to 61%. In some embodiments, the PRO is ADIQ and the therapeutically effective amount reduces the ADIQ score by 54% to 65%. In some embodiments, the IL-13 antagonist is administered to the patient using a subcutaneous administration device. In certain such embodiments, the subcutaneous administration device is selected from a prefilled syringe, disposable pen injection device, microneedle device, microinfuser device, needle-free injection device, and autoinjector device. In one embodiment, the IL-13 antagonist is lebrikizumab and lebrikizumab is administered to the patient using a prefilled syringe. In one embodiment, the IL-13 antagonist is lebrikizumab and lebrikizumab is administered to the patient using an autoinjector device.

BRIEF DESCRIPTION OF THE DRAWINGS

FIG. 1 shows the Study I Schema as described in Example 2. Abbreviations are as follows: D=day; Pbo=placebo; SC=subcutaneous; TCS=topical corticosteroid; Wk=week.

In FIG. 5, R(t) is the EASI score; $K_{in0}$ is the baseline disease progression rate constant; $k_{in}$ is the disease progression rate constant with lebrikizumab and including the placebo/TCS effect; $E_{drug}$ is the lebrikizumab drug effect on disease progression inhibition; $E_{con}$ is the placebo/TCS effect (constant overtime); $E_{max}$ is the maximum lebrikizumab drug effect on disease progression inhibition; $EC_{50}$ is the lebrikizumab concentration that leads to 50% of $E_{max}$; $k_{out}$ is the tissue repair rate constant; R(t=0) is the baseline EASI score; IIV is the inter-individual variability; $\omega_{kout}$ is the inter-individual variability for $k_{out}$; $\omega_{Econ}$ is the inter-individual variability for $E_{con}$; $\rho_{KoutXEcon}$ is the correlation between $k_{out}$ and $E_{con}$; and $\sigma$ is the residual error.

DETAILED DESCRIPTION

Figure 2A:
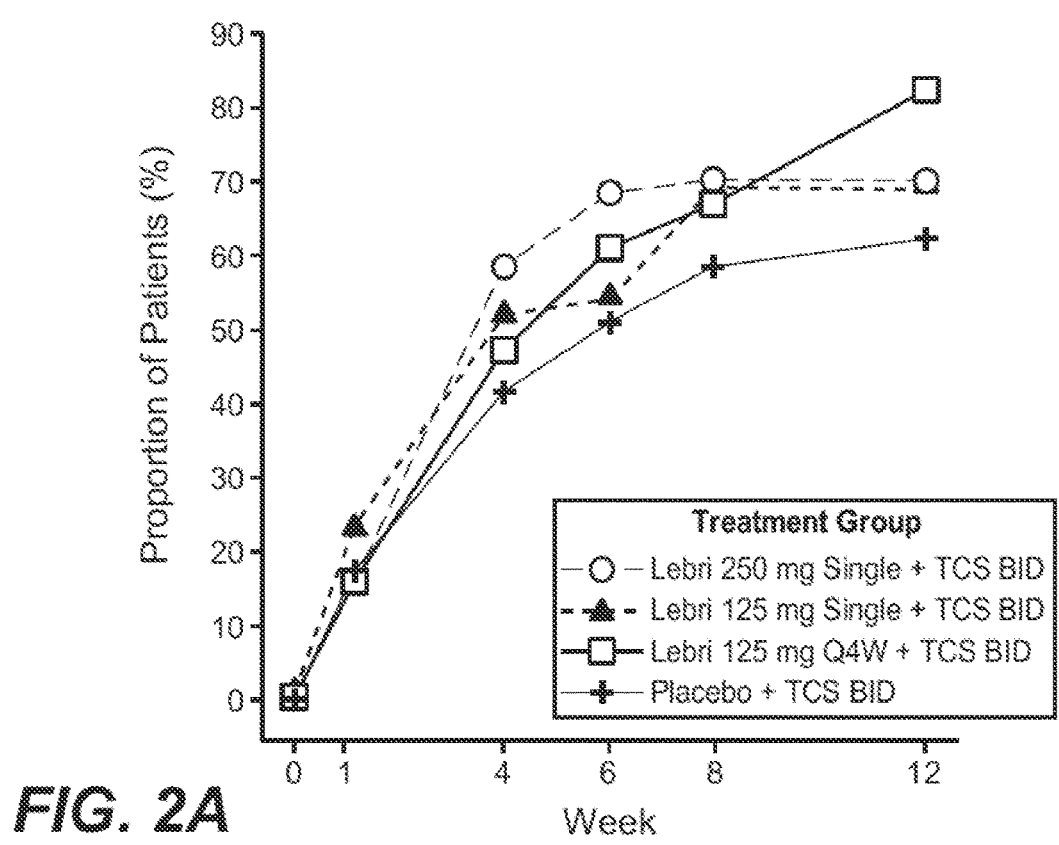
FIG. 2A shows the proportion of patients achieving EASI-50 over 12 weeks as described in Example 2. Dashed line with open circles, lebrikizumab 250 mg single dose plus topical corticosteroids (TCS) twice per day (BID); dotted line with closed triangles, lebrikizumab 125 mg single dose plus TCS twice per day; solid line with open squares, lebrikizumab 125 mg once every 4 weeks (Q4W) plus TCS twice per day; solid line with plus signs, placebo plus TCS twice per day.

All references cited herein, including patent applications and publications, are incorporated by reference in their entirety for any purpose.

Unless defined otherwise, technical and scientific terms used herein have the same meaning as commonly understood by one of ordinary skill in the art to which this invention belongs. Singleton et al., Dictionary of Microbiology and Molecular Biology 2nd ed., J. Wiley & Sons (New York, N.Y. 1994), and March, Advanced Organic Chemistry Reactions, Mechanisms and Structure 4th ed., John Wiley & Sons (New York, N.Y. 1992), provide one skilled in the art with a general guide to many of the terms used in the present application.

Certain Definitions

For purposes of interpreting this specification, the following definitions will apply and whenever appropriate, terms used in the singular will also include the plural and vice versa. In the event that any definition set forth below conflicts with any document incorporated herein by reference, the definition set forth below shall control.

As used in this specification and the appended claims, the singular forms "a," "an" and "the" include plural referents unless the context clearly dictates otherwise. Thus, for example, reference to "a protein" or an "antibody" includes a plurality of proteins or antibodies, respectively; reference to "a cell" includes mixtures of cells, and the like.

Ranges provided in the specification and appended claims include both end points and all points between the end points. Thus, for example, a range of 2.0 to 3.0 includes 2.0, 3.0, and all points between 2.0 and 3.0.

The terms "marker" and "biomarker" are used interchangeably to refer to a molecule, including a gene, protein, carbohydrate structure, or glycolipid, metabolite, mRNA, miRNA, protein, DNA (cDNA or genomic DNA), DNA copy number, or an epigenetic change, e.g., increased, decreased, or altered DNA methylation (e.g., cytosine methylation, or CpG methylation, non-CpG methylations); histone modification (e.g., (de)acetylation, (de) methylation, (de) phosphorylation, ubiquitination, SUMOylation, ADP-ribosylation); altered nucleosome positioning, the expression or presence of which in or on a mammalian tissue or cell can be detected by standard methods (or methods disclosed herein) and which may be predictive, diagnostic and/or prognostic for a mammalian cell's or tissue's sensitivity to treatment regimes based on Type-2 inflammation pathway inhibition using, for example, a Type-2 inflammation pathway inhibitor such as an anti-IL-13 antibody as described herein. A biomarker may also be a biological or clinical attribute that can be measured in a biological sample obtained from a subject, such as for example but not limited to, blood cell count.

The term "biological sample" includes, but is not limited to, blood, serum, plasma, peripheral blood mononuclear cells (PBMCs), sputum, tissue biopsies (e.g., lung samples), and nasal samples including nasal swabs or nasal polyps. The sample may be taken before treatment, during treatment or post-treatment.

The term "atopic dermatitis" or "AD" means a chronic relapsing and remitting inflammatory skin disorder characterized by intense pruritus (e.g., severe itch), xerosis (e.g., abnormally dry skin), erythematous crusting rash, lichenification, an impaired skin barrier and by scaly and dry eczematous lesions. The term "atopic dermatitis" includes, but is not limited to, AD caused by or associated with epidermal barrier dysfunction, allergy (e.g., allergy to certain foods, pollen, mold, dust mite, animals, etc.), radiation exposure, and/or asthma. In many cases, chronic AD lesions include thickened plaques of skin, lichenification and fibrous papules.

A therapeutic agent a provided herein includes an agent that can bind to the target cytokine, interleukin (IL)-13, such as a polypeptide(s) (e.g., an antibody, an immunoadhesin or a peptibody), an aptamer or a small molecule that can bind to a protein or a nucleic acid molecule that can bind to a nucleic acid molecule encoding a target identified herein (i.e., siRNA).

"Anti-IL-13 binding agent" refers to an agent that binds to human IL-13. Such binding agents can include a small molecule, aptamer or a polypeptide. Such polypeptide can include, but is not limited to, a polypeptide(s) selected from the group consisting of an immunoadhesin, an antibody, a peptibody and a peptide. According to one embodiment, the binding agent binds to a human IL-13 sequence with an affinity between 1 uM-1 pM. Specific examples of anti-IL-13 binding agents can include anti-IL-13 antibodies, soluble IL-13receptoralpha2 fused to a human Fc, soluble IL4receptoralpha fused to a human Fc, soluble IL-13 receptoralpha fused to a human Fc. Exemplary anti-IL-13 antibodies include, but are not limited to, IMA-026, IMA-638 (also referred to as, anrukinzumab, INN No. 910649-32-0; QAX-576), tralokinumab (also referred to as CAT-354, CAS No. 1044515-88-9); AER-001, ABT-308 (also referred to as humanized 13C5.5 antibody, and lebrikizumab. According to one embodiment, the anti-IL-13 antibody comprises a VH comprising a sequence selected from SEQ ID NOs: 1, 3, and 24, and a VL comprising a sequence selected from SEQ ID NO: 2, 4, and 25. In one embodiment, the anti-IL-13 antibody comprises HVRH1, HVRH2, HVRH3, HVRL1, HVRL2, and HVRL3, wherein the respective HVRs have the amino acid sequence of SEQ ID NO.: 5, SEQ ID NO.: 6, SEQ ID NO.: 7, SEQ ID NO.: 8, SEQ ID NO.: 9, and SEQ ID NO.: 10. In one embodiment, the anti-IL-13 antibody is lebrikizumab. According to one embodiment, the antibody is an IgG1 antibody. According to another embodiment, the antibody is an IgG4 antibody. According to one embodiment, the IgG4 antibody comprises a S228P mutation in its constant domain. In one embodiment, the anti-IL-13 antibody comprises a Q1E mutation in its variable heavy chain region. In one embodiment, the anti-IL-13 antibody comprises a M4L mutation in its variable light chain region.

The term "small molecule" refers to an organic molecule having a molecular weight between 50 Daltons to 2500 Daltons.

The term "antibody" is used in the broadest sense and specifically covers, for example, monoclonal antibodies, polyclonal antibodies, antibodies with polyepitopic specificity, single chain antibodies, multi-specific antibodies, including bispecific antibodies, and antibody fragments so long as they exhibit the desired antigen-binding activity. Such antibodies can be chimeric, humanized, human and synthetic.

The term "uncontrolled" or "uncontrollable" refers to the inadequacy of a treatment regimen to minimize a symptom of a disease. As used herein, the term "uncontrolled" and "inadequately controlled" can be used interchangeably and are meant to refer to the same state. The control status of a patient can be determined by the attending physician based on a number of factors including the patient's clinical history, responsiveness to treatment and level of current treatment prescribed.

The term "therapeutic agent" refers to any agent that is used to treat a disease.

The term "corticosteroid sparing" or "CS" means the decrease in frequency and/or amount, or the elimination of, corticosteroid used to treat a disease in a patient taking corticosteroids for the treatment of the disease due to the administration of another therapeutic agent. A "CS agent" refers to a therapeutic agent that can cause CS in a patient taking a corticosteroid.

The term "corticosteroid" includes, but is not limited to, topical corticosteroids. Exemplary topical corticosteroids include triamcinolone acetonide, typically formulated at a concentration of 0.1% in a cream, and hydrocortisone, typically formulated at a concentration of 1% or 2.5% in a cream. Certain topical corticosteroids are considered very high potency such as, for example, betamethasone dipropionate, clobetasol propionate, diflorasone diacetate, fluocinonide, and halobetasol propionate. Certain topical corticosteroids are considered high potency such as, for example, amcinonide, desoximetasone, halcinonide, and triamcinolone acetonide. Certain topical corticosteroids are considered medium potency, such as, for example, betamethasone valerate, clocortolone pivalate, fluocinolone acetonide, flurandrenolide, fluocinonide, fluticasone propionate, hydrocortisone butyrate, hydrocortisone valerate, mometasone furoate, and prednicarbate. Certain topical corticosteroids are considered low potency, such as, for example, alclometasone dipropionate, desonide, and hydrocortisone. "Inhalable corticosteroid" means a corticosteroid that is suitable for delivery by inhalation. Exemplary inhalable corticosteroids are fluticasone, beclomethasone dipropionate, budenoside, mometasone furoate, ciclesonide, flunisolide, triamcinolone acetonide and any other corticosteroid currently available or becoming available in the future. Examples of corticosteroids that can be inhaled and are combined with a long-acting beta2-agonist include, but are not limited to: budesonide/formoterol and fluticasone/salmeterol.

The term "loading dose" means a dose of a drug given at the beginning of a course of treatment that is higher than the dose given subsequently and each dose given for the remainder of the treatment, which is referred to as a "maintenance dose." Typically, a loading dose is administered once or twice. After administration of the loading dose or loading doses, a maintenance dose is administered and the maintenance dose is administered thereafter, typically at regular intervals, for the remainder of the course of treatment.

The term "flat dose" means that a single dose is used for all patients regardless of weight or any patient-specific factors related to weight or body mass. For example, administration of a flat dose of 100 mg of an antibody means that every patient, regardless of weight, will receive a dose of 100 mg. A flat dose is sometimes referred to as a fixed dose.

The term "weight-based dose" means a dose that is calculated based on the patient's weight. Thus, the dose administered depends on the patient's weight. For example, a dose of 1 mg/kg of an antibody means that a patient weighing 50 kg will receive a dose of 50 mg while a patient weighing 80 kg will receive a dose of 80 mg.

"Patient response" or "response" (and grammatical variations thereof) to a therapeutic agent can be assessed using any endpoint indicating a benefit to the patient, including, without limitation, (1) inhibition, to some extent, of disease progression, including slowing down and complete arrest; (2) reduction in the number of disease episodes and/or symptoms; (3) reduction in lesional size; (4) inhibition (i.e., reduction, slowing down or complete stopping) of immune or inflammatory cell infiltration into adjacent peripheral organs and/or tissues; (5) inhibition (i.e. reduction, slowing down or complete stopping) of disease spread; (6) decrease of auto-immune response, which may, but does not have to, result in the regression or ablation of the disease lesion; (7) relief, to some extent, of one or more symptoms associated with the disorder; and/or (8) increase in the length of disease-free presentation following treatment.

"A patient maintains responsiveness to a treatment" when the patient's responsiveness does not decrease with time during the course of a treatment. A patient is an "inadequate responder" when the patient's responsiveness decreases with time during the course of treatment. For example, an atopic dermatitis patient whose symptoms were controlled by topical corticosteroids (TCS) at the beginning of treatment but whose symptoms fail to be relieved by TCS administration at later times during the course of treatment is losing responsiveness to treatment and is considered an inadequate responder to TCS.

A "subcutaneous administration device" refers to a device which is adapted or designed to administer a drug, for example a therapeutic antibody, or pharmaceutical formulation by the subcutaneous route. Exemplary subcutaneous administration devices include, but are not limited to, a syringe, including a pre-filled syringe, an injection device, infusion pump, injector pen, needleless device, and patch delivery system. A subcutaneous administration device administers a certain volume of the pharmaceutical formulation, for example about 1.0 mL, about 1.25 mL, about 1.5 mL, about 1.75 mL, or about 2.0 mL.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen binding arm). The affinity of a molecule X for its partner Y can generally be represented by the dissociation constant (Kd). Affinity can be measured by common methods known in the art, including those described herein. Specific illustrative and exemplary embodiments for measuring binding affinity are described in the following.

An "affinity matured" antibody refers to an antibody with one or more alterations in one or more hypervariable regions (HVRs), compared to a parent antibody which does not possess such alterations, such alterations resulting in an improvement in the affinity of the antibody for antigen.

The terms "anti-target antibody" and "an antibody that binds to target" refer to an antibody that is capable of binding the target with sufficient affinity such that the antibody is useful as a diagnostic and/or therapeutic agent in targeting the target. In one embodiment, the extent of binding of an anti-target antibody to an unrelated, non-target protein is less than about 10% of the binding of the antibody to target as measured, e.g., by a radioimmunoassay (MA) or biacore assay. In certain embodiments, an antibody that binds to a target has a dissociation constant (Kd) of ≤1 M, ≤100 nM, ≤10 nM, ≤1 nM, ≤0.1 nM, ≤0.01 nM, or ≤0.001 nM (e.g. 10-8 M or less, e.g. from 10-8 M to 10-13 M, e.g., from 10-9 M to 10-13 M). In certain embodiments, an anti-target antibody binds to an epitope of a target that is conserved among different species.

An "antibody fragment" refers to a molecule other than an intact antibody that comprises a portion of an intact antibody that binds the antigen to which the intact antibody binds. Examples of antibody fragments include but are not limited to single chain Fv, Fab, Fab', Fab'-SH, F(ab')2; diabodies; linear antibodies; single-chain antibody molecules (e.g. scFv); and multispecific antibodies formed from antibody fragments.

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more. Various methods for carrying out competition assays are well-known in the art.

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

The term "chimeric" antibody refers to an antibody in which a portion of the heavy and/or light chain is derived from a particular source or species, while the remainder of the heavy and/or light chain is derived from a different source or species.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., IgG1, IgG2, IgG3, IgG4, IgA1, and IgA2. The heavy chain constant domains that correspond to the different classes of immunoglobulins are called α, δ, ε, γ, and μ, respectively.

"Effector functions" refer to those biological activities attributable to the Fc region of an antibody, which vary with the antibody isotype. Examples of antibody effector functions include: Clq binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

An "effective amount" of an agent, e.g., a pharmaceutical formulation, refers to an amount effective, at dosages and for periods of time necessary, to achieve the desired therapeutic or prophylactic result.

The term "Fc region" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., Sequences of Proteins of Immunological Interest, 5th Ed. Public Health Service, National Institutes of Health, Bethesda, MD, 1991.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

The terms "full length antibody," "intact antibody," and "whole antibody" are used herein interchangeably to refer to an antibody having a structure substantially similar to a native antibody structure or having heavy chains that contain an Fc region as defined herein.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., Sequences of Proteins of Immunological Interest, Fifth Edition, NIH Publication 91-3242, Bethesda MD (1991), vols. 1-3. In one embodiment, for the VL, the subgroup is subgroup kappa I as in Kabat et al., supra. In one embodiment, for the VH, the subgroup is subgroup III as in Kabat et al., supra.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "hypervariable region" or "HVR" refers to each of the regions of an antibody variable domain which are hypervariable in sequence and/or form structurally defined loops ("hypervariable loops"). Generally, native four-chain antibodies comprise six HVRs; three in the VH (H1, H2, H3), and three in the VL (L1, L2, L3). HVRs generally comprise amino acid residues from the hypervariable loops and/or from the "complementarity determining regions" (CDRs), the latter typically being of highest sequence variability and/or involved in antigen recognition. An HVR region as used herein comprise any number of residues located within positions 24-36 (for HVRL1), 46-56 (for HVRL2), 89-97 (for HVRL3), 26-35B (for HVRH1), 47-65 (for HVRH2), and 93-102 (for HVRH3).

An "individual" or "patient" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or patient or subject is a human. In some embodiments, an "individual" or "patient" or "subject" herein is any single human subject eligible for treatment who is experiencing or has experienced one or more signs, symptoms, or other indicators of asthma or a respiratory condition. Intended to be included as a subject are any subjects involved in clinical research trials not showing any clinical sign of disease, or subjects involved in epidemiological studies, or subjects once used as controls. The subject may have been previously treated with an IL-13 antagonist or another drug, or not so treated. The subject may be naïve to an IL-13 antagonist when the treatment herein is started, i.e., the subject may not have been previously treated with, for example, an IL-13 antagonist at "baseline" (i.e., at a set point in time before the administration of a first dose of an IL-13 antagonist in the treatment method herein, such as the day of screening the subject before treatment is commenced). Such "naïve" subjects are generally considered to be candidates for treatment with such drug(s).

A "pediatric" individual or patient or subject is a human from birth to 18 years old (or 0 to 18 years old). In some embodiments, a pediatric individual or patient or subject is from 2 to 6, 2 to 17, 6 to 11, 6 to 18, 6 to 17, 8 to 17, 12 to 17, or 12 to 18 years old.

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman et al., J. Chromatogr. B 848:79-87 (2007).

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Isolated nucleic acid encoding an anti-target antibody" refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

The term "monoclonal antibody" refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a mono-clonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homoge-neous population of antibodies, and is not to be construed as requiring production of the antibody by any particular method. For example, the monoclonal antibodies to be used according to the methods provided herein may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

A "naked antibody" refers to an antibody that is not conjugated to a heterologous moiety (e.g., a cytotoxic moi-ety) or radiolabel. The naked antibody may be present in a pharmaceutical formulation.

"Native antibodies" refer to naturally occurring immuno-globulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

The term "package insert" is used to refer to instructions customarily included in commercial packages of therapeutic products, that contain information about the indications, usage, dosage, administration, combination therapy, con-traindications and/or warnings concerning the use of such therapeutic products. The term "package insert" is also used to refer to instructions customarily included in commercial packages of diagnostic products that contain information about the intended use, test principle, preparation and han-dling of reagents, specimen collection and preparation, calibration of the assay and the assay procedure, perfor-mance and precision data such as sensitivity and specificity of the assay.

"Percent (%) amino acid sequence identity" with respect to a reference polypeptide sequence is defined as the per-centage of amino acid residues in a candidate sequence that are identical with the amino acid residues in the reference polypeptide sequence, after aligning the sequences and introducing gaps, if necessary, to achieve the maximum percent sequence identity, and not considering any conser-vative substitutions as part of the sequence identity. Align-ment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, California, or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding para-graph using the ALIGN-2 computer program.

The term "pharmaceutical formulation" or "pharmaceu-tical composition" refers to a preparation which is in such form as to permit the biological activity of an active ingre-dient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharma-ceutically acceptable carrier includes, but is not limited to, a buffer, excipient, stabilizer, or preservative.

The term "target" refers to any native molecule from any vertebrate source, including mammals such as primates (e.g. humans) and rodents (e.g., mice and rats), unless otherwise indicated. The term encompasses "full-length," unprocessed target as well as any form of target that results from processing in the cell. The term also encompasses naturally occurring variants of targets, e.g., splice variants or allelic variants.

The term "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occur-rence or recurrence of disease, alleviation of symptoms, diminishment of any direct or indirect pathological conse-quences of the disease, preventing metastasis, decreasing the rate of disease progression, amelioration or palliation of the disease state, and remission or improved prognosis. In some embodiments, antibodies are used to delay development of a disease or to slow the progression of a disease.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt et al. Kuby Immunology, 6th ed., W. H. Freeman and Co., page 91 (2007).) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., J. Immunol. 150:880-887 (1993); Clarkson et al., Nature 352:624-628 (1991).

The term "vector" refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

The term "flare" in a patient diagnosed with atopic dermatitis means a measurable increase in extent or severity of lesions over a period of at least 3 days, under continued treatment and corresponding with a clinically significant increase in disease severity (as assessed by the treating physician and/or by the patient) necessitating an escalation in therapy (see, e.g., Darsow et al., J Eur Acad Dermatol Venereol 2010; 24:317-28).

Atopic dermatitis can be diagnosed using "Hanifin/Rajka criteria." Hanifin/Rajka diagnostic criteria are described in Acta Derm Venereol (Stockh) 1980; Suppl 92:44-7. To establish a diagnosis of atopic dermatitis the patient requires the presence of at least 3 "basic features" and 3 or more minor features listed below. The basic features include pruritus, typical morphology and distribution such as flexural lichenification or linearity, chronic or chronically-relapsing dermatitis, and personal or family history of atopy, such as asthma, allergic rhinitis, atopic dermatitis. The minor features include xerosis, ichthyosis, palmar hyperlinearity, or keratosis pilaris, immediate (type 1) skin-test reactivity, elevated serum IgE, early age of onset, tendency toward cutaneous infections (especially *Staph. aureus* and *Herpes simplex*), impaired cell-mediated immunity, tendency toward non-specific hand or foot dermatitis, nipple eczema, cheilitis, recurrent conjunctivitis, Dennie-Morgan infraorbital fold, keratoconus, anterior subcapsular cataracts, orbital darkening, facial pallor/facial erythema, pityriasis alba, anterior neck folds, and itch when sweating. Additional minor criteria include intolerance to wool and lipid solvents, perifollicular accentuation, food intolerance, course influenced by environmental or emotional factors, and white dermographism/delayed blanch.

The severity of atopic dermatitis can be determined by "Rajka/Langeland criteria," as described in Rajka G and Langeland T, Acta Derm Venereol (Stockh) 1989; 144 (Suppl):13-4. Three disease severity assessment categories are scored 1 to 3: I) extent of the body area involved, II) course, e.g., more or less than 3 months during one year or continuous course, and III) intensity, ranging from mild itch to severe itch, usually disturbing night's sleep. Scores of 1.5 or 2.5 are allowed. Overall disease severity is determined by the sum of individual scores from the three disease assessment categories and the severity is determined by the sum of these scores with mild defined as a total score of 3-4, moderate as score of 4.5-7.5, and severe as a total score of 8-9.

The term "Atopic Dermatitis Disease Severity Outcome Measure" or "ADDSOM" means a determination of certain signs, symptoms, features or parameters that have been associated with atopic dermatitis and that can be quantitatively or qualitatively assessed. Exemplary ADDSOMs include, but are not limited to, "Eczema Area and Severity Index" (EAST), "Severity Scoring of Atopic Dermatitis" (SCORAD), "Investigator Global Assessment" (IGA), "Investigator Global Assessment of Signs" (IGSA), Rajka/Langeland Atopic Dermatitis Severity Score, and Patient-Reported Outcomes including, but not limited to, Pruritus Visual Analog Scale (an aspect of disease severity assessed as part of SCORAD), Sleep Loss Visual Analog Scale (an aspect of disease severity assessed as part of SCORAD), Atopic Dermatitis Symptom Diary (ADSD), Atopic Dermatitis Impact Questionnaire (ADIQ), Dermatology Life Quality Index (DLQI) (Finlay and Khan, Clin Exper Dermatol 1994; 19:210), and 5-D Itch Scale (Elman et al., Br J Dermatol 2010; 162(3):587-593).

The "Eczema Area and Severity Index" or "EAST" is a validated measure used in clinical settings to assess the severity and extent of AD, Hanifin et al., Exp Dermatol 2001; 10:11-18. Four individual body regions are assessed by a clinician or other medical professional: head and neck (H&N), upper limbs (UL; includes the external axillae and hands), trunk (includes the internal axillae and groin), and lower limbs (LL; includes the buttocks and feet). For each body region, the affected body surface area (BSA) is assessed and assigned a score of 0 to 6 (or optionally 0-7 where 0 equals no eruption) for the percentage of affected BSA (0%-100%); each region is individually rated for the average degree of severity (0-3: none, mild, moderate, severe), with half steps allowed, for each of four clinical signs: erythema, induration-papulation, excoriations, and lichenification. A summed score of 0 to 12 is assigned to each body region; a total body region score is assigned based on the sum of the individual clinical signs score (maximum=12)×affected area score (maximum=6)×the body-region index (H&N—0.1, UL—0.2, trunk—0.3, LL—0.4). A total score (0-72) is assigned based on the sum of total scores for each of the four body region scores.

The "Investigator Global Assessment" or "IGA" is an assessment measure used in clinical settings to determine the severity of AD and clinical response to treatment based on a five-point scale. A score of 0 (clear) means there are no inflammatory signs of atopic dermatitis and a score of 1 (almost clear) means there is just perceptible erythema and just perceptible papulation induration. Scores of 2, 3, or 4 (mild, moderate, severe) are based on the severity of erythema, papulation induration, oozing and crusting. The "Investigator Global Assessment of Signs" or "IGSA" uses a lesional assessment grade ranging from clear to severe based on an evaluation of erythema, edema, lichenified plaques or papules, and excoriations. In addition, the assessed lesional grade may be upgraded or downgraded based on the extent and location of the skin lesion.

The "Severity Scoring of Atopic Dermatitis" or "SCORAD" is a clinical assessment of the severity of AD developed by the European Task Force on Atopic Dermatitis (consensus report, Dermatology 1993; 186:23-31). Three aspects of disease severity are scored: (i) the extent of body area affected by inflammation with score assessed between 0-100, assigned as "A" in the overall total score, (ii) the intensity of six clinical signs, erythema, edema/population, oozing/crusting, excoriation, lichenification, and dryness, each assigned a score of 0-3 based on severity (absent, mild, moderate, severe) for a total score ranging from 0-18, assigned as "B" in the overall total score, and (iii) two subjective measures that use patient-reported outcomes, the pruritus visual analog score (ranging from 0 [no itch] to 10 [the worst imaginable itch]) and the sleep loss visual analog score (ranging from 0 [no sleep loss] to 10 [the worst imaginable sleep loss]), each the average of the last three days or nights, assigned as "C" in the overall total score. The overall total score (0-103) is determined according to the formula: A/5+(7B/2)+C.

The term "Patient-Reported Outcome" or "PRO" means a validated questionnaire or tool used in clinical practice or in clinical trials to assess quality of life from a patient's point of view regarding the patient's atopic dermatitis disease symptoms which may include emotional and functional impacts of the disease. A PRO is a report of the status of a patient's health condition that comes directly from the patient, without interpretation of the patient's response by a clinician or anyone else. The outcome can be measured in absolute terms (e.g., severity of a symptom, sign, or state of a disease) or as a change from a previous measure. In clinical trials, a PRO instrument can be used to measure the effect of a medical intervention on one or more concepts (i.e., the thing being measured, such as a symptom or group of symptoms, effects on a particular function or group of functions, or a group of symptoms or functions shown to measure the severity of a health condition). Exemplary PRO tools used to assess AD include, but are not limited to, Pruritus Visual Analog Scale (an aspect of disease severity assessed as part of SCORAD), Sleep Loss Visual Analog Scale (an aspect of disease severity assessed as part of SCORAD), Atopic Dermatitis Symptom Diary (ADSD), Atopic Dermatitis Impact Questionnaire (ADIQ), Dermatology Life Quality Index (DLQI) (Finlay and Khan, Clin Exper Dermatol 1994; 19:210), and 5-D Itch Scale (Elman et al., Br J Dermatol 2010; 162(3):587-593).

Compositions and Methods

The invention is based, at least in part, on the surprising and unexpected discovery that an anti-IL-13 antagonist monoclonal antibody, lebrikizumab, provides therapeutic benefit when administered to atopic dermatitis patients using the dosing regimens provided herein, including patients using topical corticosteroids concomitantly, as assessed by several efficacy outcome measures. Accordingly, provided herein are methods of treating atopic dermatitis with IL-13 antagonists, including anti-IL-13 antibodies such as lebrikizumab.

Lebrikizumab is a humanized, monoclonal, IgG4 antibody that binds IL-13 with high affinity and blocks signaling through the active IL-4Ralpha/IL-13Ralpha1 heterodimer. Lebrikizumab has been clinically tested in asthma at various doses and the results have been reported in the literature as summarized below.

In the MILLY study, adults with poorly controlled asthma despite inhaled corticosteroid treatment were administered 250 mg of lebrikizumab or placebo once every four weeks for a total of six months. Corren et al., N Engl J Med 2011; 365:1088-98. Lebrikizumab-treated patients, particularly those in the biomarker high (serum periostin-high) subgroup, exhibited greater improvements in lung function, as measured by $FEV_1$, than those in the placebo group. Corren et al., supra.

The MOLLY study was a dose-ranging study in which asthma patients not receiving inhaled corticosteroids received 125 mg of lebrikizumab or 250 mg lebrikizumab or 500 mg lebrikizumab or placebo once every four weeks for a total of 12 weeks. Noonan et al., J Allergy Clin Immunol 2013; 132:567-74. Although the mean relative change in $FEV_1$ was numerically higher in all lebrikizumab dose groups compared to the placebo group, these differences were neither statistically nor clinically significant. Noonan et al., supra. In addition, the MOLLY study did not meet the objectives for demonstrating a dose-response. Noonan et al., supra. One conclusion from the results is that blocking a single cytokine, IL-13, in that population of asthma patients in the MOLLY study, was insufficient to improve lung function as measured by $FEV_1$ compared with existing treatments. Noonan et al., supra.

In the LUTE and VERSE studies, three different doses of lebrikizumab, 37.5 mg, 125 mg and 250 mg, administered once every four weeks, were tested in moderate-to-severe asthmatic patients not controlled on inhaled corticosteroids. Hanania et al., Thorax 2015; 70:748-756. Treatment with lebrikizumab reduced the rate of asthma exacerbations, which was more pronounced in the biomarker-high (serum periostin-high) patients (all doses: 60% reduction) than in the biomarker-low (serum periostin-low) patients (all doses: 5% reduction); no clear dose—response was evident, however. Hanania et al., 2015, supra. Lung function also improved following lebrikizumab treatment, with greatest increase in $FEV_1$ in periostin-high patients compared with periostin-low patients. Hanania et al., 2015, supra.

As described herein, both AD and asthma patients have elevated levels of biomarkers associated with IL-13 biology and Th-2 mediated hypersensitivity. Accordingly, it was thought that the dose levels of lebrikizumab producing clinical benefit in asthma could also produce biological activity in AD patients. Thus, the initial doses proposed for testing in AD patients as set forth in Clinical Study I and Clinical Study II described in the Examples were based on the published clinical experience with asthma as described above.

After initiation of Clinical Study I and Clinical Study II described herein, the results of the phase 3 clinical studies of lebrikizumab in asthma (LAVOLTA I and LAVOLTA II) were analyzed and published online Sep. 5, 2016 in Hanania et al., Lancet Respir Med 2016, available at dx(dot)doi(dot) org(slash)52213-2600(16)30265-X. LAVOLTA I and II were replicate phase 3 studies to assess the efficacy and safety of lebrikizumab in patients with uncontrolled asthma despite inhaled corticosteroids and at least one second controller. These phase 3 studies were designed for the purpose of seeking marketing approval from health authorities world-wide provided there was a demonstration of statistically significant efficacy in both studies and an acceptable safety profile.

In LAVOLTA I and II, patients were treated with 37.5 mg lebrikizumab or 125 mg lebrikizumab or placebo, administered once every four weeks, over 52 weeks. The primary efficacy endpoint was a reduction in the rate of exacerbations. Patients were stratified according to biomarker-high (serum periostin-high or blood eosinophil count-high) or biomarker-low (serum periostin-low or blood eosinophil count-low). As reported in Hanania et al., 2016, supra, the efficacy results across both studies were inconsistent. Lebrikizumab significantly reduced the rate of exacerbations in biomarker-high patients in LAVOLTA I but not in LAVOLTA II. Hanania et al., 2016, supra. Both studies failed to show a clear dose-response although pharmacokinetic and pharmacodynamics results were consistent with those from the phase II studies described above, indicating that drug exposures were similar and that the IL-13 pathway was inhibited. Hanania et al., 2016, supra.

Accordingly, although the lebrikizumab dosing regimens tested in the atopic dermatitis Clinical Study I and Clinical Study II described herein were based on the clinical experience with asthma, it was uncertain whether lebrikizumab would provide clinically meaningful benefit to atopic dermatitis patients at the dosing regimens described for Clinical Study I and Clinical Study II. The inconsistent results of lebrikizumab in asthma patients and the lack of a clear dose-response across multiple studies as summarized above, including in view of the results reported for the phase 3 LAVOLTA I and II studies, contribute to such uncertainty with respect to therapeutic benefit of lebrikizumab in atopic dermatitis patients. Prior to the invention described herein, it would have been unpredictable whether lebrikizumab could provide clinically meaningful benefit to atopic dermatitis patients at the dosing regimens provided herein.

Exemplary Antibodies

Anti-IL-13 Antibodies

In one aspect, the invention provides isolated antibodies that bind to human IL-13.

Exemplary anti-IL-13 antibodies are known and include, for example, but not limited to, lebrikizumab, IMA-026, IMA-638 (also referred to as, anrukinzumab, INN No. 910649-32-0; QAX-576), tralokinumab (also referred to as CAT-354, CAS No. 1044515-88-9); AER-001, ABT-308 (also referred to as humanized 13C5.5 antibody. Examples of such anti-IL-13 antibodies and other inhibitors of IL-13 are disclosed, for example, in WO 2005/062967, WO2008/086395, WO2006/085938, U.S. Pat. Nos. 7,615,213, 7,501, 121, WO2007/036745, WO2010/073119, WO2007/045477, WO 2014/165771. In one embodiment, the anti-IL-13 antibody is a humanized IgG4 antibody. In one embodiment, the anti-IL-13 antibody is lebrikizumab. In one embodiment, the anti-IL-13 antibody comprises three heavy chain HVRs, HVR-H1 (SEQ ID NO.: 5), HVR-H2 (SEQ ID NO.: 6), and HVR-H3 (SEQ ID NO.: 7). In one embodiment, the anti-IL-13 antibody comprises three light chain HVRS, HVR-L1 (SEQ ID NO.: 8), HVR-L2 (SEQ ID NO.: 9), and HVR-L3 (SEQ ID NO.: 10). In one embodiment, the anti-IL-13 antibody comprises three heavy chain HVRs and three light chain HVRs, HVR-H1 (SEQ ID NO.: 5), HVR-H2 (SEQ ID NO.: 6), HVR-H3 (SEQ ID NO.: 7), HVR-L1 (SEQ ID NO.: 8), HVR-L2 (SEQ ID NO.: 9), and HVR-L3 (SEQ ID NO.: 10). In one embodiment, the anti-IL-13 antibody comprises a variable heavy chain region, VH, having an amino acid sequence selected from SEQ ID NOs. 1, 3, and 24. In one embodiment, the anti-IL-13 antibody comprises a variable light chain region, VL, having an amino acid sequence selected from SEQ ID NOs.: 2, 4, and 25. In one embodiment, the anti-IL-13 antibody comprises a variable heavy chain region, VH, having an amino acid sequence selected from SEQ ID NOs. 1, 3, and 24 and a variable light chain region, VL, having an amino acid sequence selected from SEQ ID NOs.: 2, 4, and 25.

In another embodiment, the antibody comprises the variable region sequences SEQ ID NO:1 and SEQ ID NO:2. In another embodiment, the antibody comprises the variable region sequences SEQ ID NO:1 and SEQ ID NO:4. In another embodiment, the antibody comprises the variable region sequences SEQ ID NO:1 and SEQ ID NO:25. In another embodiment, the antibody comprises the variable region sequences SEQ ID NO:3 and SEQ ID NO:2. In another embodiment, the antibody comprises the variable region sequences SEQ ID NO:3 and SEQ ID NO:4. In another embodiment, the antibody comprises the variable region sequences SEQ ID NO:3 and SEQ ID NO:25. In another embodiment, the antibody comprises the variable region sequences SEQ ID NO:24 and SEQ ID NO:2. In another embodiment, the antibody comprises the variable region sequences SEQ ID NO:24 and SEQ ID NO:4. In another embodiment, the antibody comprises the variable region sequences SEQ ID NO:24 and SEQ ID NO:25.

In any of the above embodiments, an anti-IL-13 antibody can be humanized. In one embodiment, an anti-IL-13 antibody comprises HVRs as in any of the above embodiments, and further comprises an acceptor human framework, e.g. a human immunoglobulin framework or a human consensus framework.

In another aspect, an anti-IL-13 antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO:1. In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-IL-13 antibody comprising that sequence retains the ability to bind to human IL-13. In certain embodiments, a total of 1 to 10 amino acids have been substituted, altered inserted and/or deleted in SEQ ID NO: 1. In certain embodiments, substitutions, insertions, or deletions occur in regions outside the HVRs (i.e., in the FRs). Optionally, the anti-IL-13 antibody comprises the VH sequence in SEQ ID NO: 1, including post-translational modifications of that sequence. Optionally, the anti-IL-13 antibody comprises the VH sequence in SEQ ID NO: 3, including post-translational modifications of that sequence. Optionally, the anti-IL-13 antibody comprises the VH sequence in SEQ ID NO: 24, including post-translational modifications of that sequence.

In another aspect, an anti-IL-13 antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO:2. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-IL-13 antibody comprising that sequence retains the ability to bind to IL-13. In certain embodiments, a total of 1 to 10 amino acids have been substituted, inserted and/or deleted in SEQ ID NO:2. In certain embodiments, the substitutions, insertions, or deletions occur in regions outside the HVRs (i.e., in the FRs). Optionally, the anti-IL-13 antibody comprises the VL sequence in SEQ ID NO:2, including post-translational modifications of that sequence. Optionally, the anti-IL-13 antibody comprises the VL sequence in SEQ ID NO: 4, including post-translational modifications of that sequence. Optionally, the anti-IL-13 antibody comprises the VL sequence in SEQ ID NO: 25, including post-translational modifications of that sequence.

In another aspect, an anti-IL-13 antibody is provided, wherein the antibody comprises a VH as in any of the embodiments provided above, and a VL as in any of the embodiments provided above.

In a further aspect, the invention provides an antibody that binds to the same epitope as an anti-IL-13 antibody provided herein. For example, in certain embodiments, an antibody is provided that binds to the same epitope as or can by competitively inhibited by an anti-IL-13 antibody comprising a VH sequence of SEQ ID NO:1 and a VL sequence of SEQ ID NO:2.

In a further aspect of the invention, an anti-IL-13 antibody according to any of the above embodiment can be a monoclonal antibody, including a chimeric, humanized or human antibody. In one embodiment, an anti-IL-13 antibody is an antibody fragment, e.g., a Fv, Fab, Fab', scFv, diabody, or F(ab')2 fragment. In another embodiment, the antibody is a full length antibody, e.g., an intact IgG1 or IgG4 antibody or other antibody class or isotype as defined herein. According to another embodiment, the antibody is a bispecific antibody. In one embodiment, the bispecific antibody comprises the HVRs or comprises the VH and VL regions described above.

In one embodiment, the anti-IL-13 antibody comprises three heavy chain HVRs, HVR-H1 (SEQ ID NO.: 13), HVR-H2 (SEQ ID NO.: 14), and HVR-H3 (SEQ ID NO.: 15). In one embodiment, the anti-IL-13 antibody comprises three light chain HVRS, HVR-L1 (SEQ ID NO.: 16), HVR-L2 (SEQ ID NO.: 17), and HVR-L3 (SEQ ID NO.: 18). In one embodiment, the anti-IL-13 antibody comprises three heavy chain HVRs and three light chain HVRs, HVR-H1 (SEQ ID NO.: 13), HVR-H2 (SEQ ID NO.: 14), HVR-H3 (SEQ ID NO.: 15), HVR-L1 (SEQ ID NO.: 16), HVR-L2 (SEQ ID NO.: 17), and HVR-L3 (SEQ ID NO.: 18). In one embodiment, the anti-IL-13 antibody comprises a variable heavy chain region, VH, having the amino acid sequence of SEQ ID NO: 12. In one embodiment, the anti-IL-13 antibody comprises a variable light chain region, VL, having the amino acid sequence of SEQ ID NO: 11. In one embodiment, the anti-IL-13 antibody comprises a variable heavy chain region, VH, having the amino acid sequence of SEQ ID NO: 12 and a variable light chain region, VL, having the amino acid sequence of SEQ ID NO: 11.

In any of the above embodiments, an anti-IL-13 antibody can be humanized. In one embodiment, an anti-IL-13 antibody comprises HVRs as in any of the above embodiments, and further comprises an acceptor human framework, e.g. a human immunoglobulin framework or a human consensus framework.

In another aspect, an anti-IL-13 antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO:12. In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-IL-13 antibody comprising that sequence retains the ability to bind to human IL-13. In certain embodiments, a total of 1 to 10 amino acids have been substituted, altered inserted and/or deleted in SEQ ID NO: 12. In certain embodiments, substitutions, insertions, or deletions occur in regions outside the HVRs (i.e., in the FRs). Optionally, the anti-IL-13 antibody comprises the VH sequence in SEQ ID NO: 12, including post-translational modifications of that sequence.

In another aspect, an anti-IL-13 antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO:11. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-IL-13 antibody comprising that sequence retains the ability to bind to IL-13. In certain embodiments, a total of 1 to 10 amino acids have been substituted, inserted and/or deleted in SEQ ID NO:11. In certain embodiments, the substitutions, insertions, or deletions occur in regions outside the HVRs (i.e., in the FRs). Optionally, the anti-IL-13 antibody comprises the VL sequence in SEQ ID NO:11, including post-translational modifications of that sequence.

In another aspect, an anti-IL-13 antibody is provided, wherein the antibody comprises a VH as in any of the embodiments provided above, and a VL as in any of the embodiments provided above.

In a further aspect, the invention provides an antibody that binds to the same epitope as an anti-IL-13 antibody provided herein. For example, in certain embodiments, an antibody is provided that binds to the same epitope as or can by competitively inhibited by an anti-IL-13 antibody comprising a VH sequence of SEQ ID NO:12 and a VL sequence of SEQ ID NO:11.

In a further aspect of the invention, an anti-IL-13 antibody according to any of the above embodiment can be a monoclonal antibody, including a chimeric, humanized or human antibody. In one embodiment, an anti-IL-13 antibody is an antibody fragment, e.g., a Fv, Fab, Fab', scFv, diabody, or F(ab')2 fragment. In another embodiment, the antibody is a full length antibody, e.g., an intact IgG1 or IgG4 antibody or other antibody class or isotype as defined herein. According to another embodiment, the antibody is a bispecific antibody. In one embodiment, the bispecific antibody comprises the HVRs or comprises the VH and VL regions described above.

In a further aspect, an anti-IL-13 antibody according to any of the above embodiments may incorporate any of the features, singly or in combination, as described in Sections 1-7 below:

1. Antibody Affinity

In certain embodiments, an antibody provided herein has a dissociation constant (Kd) of ≤1 µM, ≤100 nM, ≤10 nM, ≤1 nM, ≤0.1 nM, ≤0.01 nM, or ≤0.001 nM (e.g. 10-8 M or less, e.g. from 10-8 M to 10-13 M, e.g., from 10-9 M to 10-13 M).

In one embodiment, Kd is measured by a radiolabeled antigen binding assay (MA) performed with the Fab version of an antibody of interest and its antigen as described by the following assay. Solution binding affinity of Fabs for antigen is measured by equilibrating Fab with a minimal concentration of (125I)-labeled antigen in the presence of a titration series of unlabeled antigen, then capturing bound antigen with an anti-Fab antibody-coated plate (see, e.g., Chen et al., J. Mol. Biol. 293:865-881(1999)). To establish conditions for the assay, MICROTITER® multi-well plates (Thermo Scientific) are coated overnight with 5 µg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 µM or 26 µM [125I]-antigen are mixed with serial dilutions of a Fab of interest (e.g., consistent with assessment of the anti-VEGF antibody, Fab-12, in Presta et al., Cancer Res. 57:4593-4599 (1997)). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20®) in PBS. When the plates have dried, 150 µl/well of scintillant (MICROSCINT-20™; Packard) is added, and the plates are counted on a TOP-COUNT™ gamma counter (Packard) for ten minutes. Concentrations of each Fab that give less than or equal to 20% of maximal binding are chosen for use in competitive binding assays.

According to another embodiment, Kd is measured using surface plasmon resonance assays using a BIACORE®-2000 or a BIACORE®-3000 (BlAcore, Inc., Piscataway, NJ) at 25° C. with immobilized antigen CMS chips at ~10 response units (RU). Briefly, carboxymethylated dextran biosensor chips (CMS, BIACORE, Inc.) are activated with N-ethyl-N'-(3-dimethylaminopropyl)-carbodiimide hydrochloride (EDC) and N-hydroxysuccinimide (NETS) according to the supplier's instructions. Antigen is diluted with 10 mM sodium acetate, pH 4.8, to 5 µg/ml (~0.2 µM) before injection at a flow rate of 5 µl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20™) surfactant (PBST) at 25° C. at a flow rate of approximately 25 µl/min. Association rates (kon) and dissociation rates (koff) are calculated using a simple one-to-one Langmuir binding model (BIACORE® Evaluation Software version 3.2) by simultaneously fitting the association and dissociation sensorgrams. The equilibrium dissociation constant (Kd) is calculated as the ratio koff/kon. See, e.g., Chen et al., J. Mol. Biol. 293:865-881 (1999). If the on-rate exceeds 106 M−1 s−1 by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-AMINCO™ spectrophotometer (ThermoSpectronic) with a stirred cuvette.

2. Antibody Fragments

In certain embodiments, an antibody provided herein is an antibody fragment. Antibody fragments include, but are not limited to, Fab, Fab', Fab'-SH, F(ab')2, Fv, and scFv fragments, and other fragments described below. For a review of certain antibody fragments, see Hudson et al. Nat. Med. 9:129-134 (2003). For a review of scFv fragments, see, e.g., Pluckthiin, in The Pharmacology of Monoclonal Antibodies, vol. 113, Rosenburg and Moore eds., (Springer-Verlag, New York), pp. 269-315 (1994); see also WO 93/16185; and U.S. Pat. Nos. 5,571,894 and 5,587,458. For discussion of Fab and F(ab')2 fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP 404,097; WO 1993/01161; Hudson et al., Nat. Med. 9:129-134 (2003); and Hollinger et al., Proc. Natl. Acad. Sci. USA 90: 6444-6448 (1993). Triabodies and tetrabodies are also described in Hudson et al., Nat. Med. 9:129-134 (2003).

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, MA; see, e.g., U.S. Pat. No. 6,248,516 B1).

Antibody fragments can be made by various techniques, including but not limited to proteolytic digestion of an intact antibody as well as production by recombinant host cells (e.g. E. coli or phage), as described herein.

3. Chimeric and Humanized Antibodies

In certain embodiments, an antibody provided herein is a chimeric antibody. Certain chimeric antibodies are described, e.g., in U.S. Pat. No. 4,816,567; and Morrison et al., Proc. Natl. Acad. Sci. USA, 81:6851-6855 (1984)). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro and Fransson, Front. Biosci. 13:1619-1633 (2008), and are further described, e.g., in Riechmann et al., Nature 332:323-329 (1988); Queen et al., Proc. Nat'l Acad. Sci. USA 86:10029-10033 (1989); U.S. Pat. Nos. 5,821,337, 7,527,791, 6,982,321, and 7,087,409; Kashmiri et al., Methods 36:25-34 (2005) (describing SDR (a-CDR) grafting); Padlan, Mol. Immunol. 28:489-498 (1991) (describing "resurfacing"); Dall'Acqua et al., Methods 36:43-60 (2005) (describing "FR shuffling"); and Osbourn et al., Methods 36:61-68 (2005) and Klimka et al., Br. J. Cancer, 83:252-260 (2000) (describing the "guided selection" approach to FR shuffling).

Human framework regions that may be used for humanization include but are not limited to: framework regions selected using the "best-fit" method (see, e.g., Sims et al. J. Immunol. 151:2296 (1993)); framework regions derived from the consensus sequence of human antibodies of a particular subgroup of light or heavy chain variable regions (see, e.g., Carter et al. Proc. Natl. Acad. Sci. USA, 89:4285 (1992); and Presta et al. J. Immunol., 151:2623 (1993)); human mature (somatically mutated) framework regions or human germline framework regions (see, e.g., Almagro and Fransson, Front. Biosci. 13:1619-1633 (2008)); and framework regions derived from screening FR libraries (see, e.g., Baca et al., J. Biol. Chem. 272:10678-10684 (1997) and Rosok et al., J. Biol. Chem. 271:22611-22618 (1996)).

4. Human Antibodies

In certain embodiments, an antibody provided herein is a human antibody. Human antibodies can be produced using various techniques known in the art. Human antibodies are described generally in van Dijk and van de Winkel, Curr. Opin. Pharmacol. 5: 368-74 (2001) and Lonberg, Curr. Opin. Immunol. 20:450-459 (2008).

Human antibodies may be prepared by administering an immunogen to a transgenic animal that has been modified to produce intact human antibodies or intact human antibodies with

US 12,692,302 B2

35 human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, Nat. Biotech. 23:1117-1125 (2005). See also, e.g., U.S. Pat. Nos. 6,075,181 and 6,150,584 describing XENO-MOUSE™ technology; U.S. Pat. No. 5,770,429 describing HUMAB® technology; U.S. Pat. No. 7,041,870 describing K-M MOUSE® technology, and U.S. Patent Application Publication No. US 2007/0061900, describing VELOCI-MOUSE® technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor J. Immunol., 133: 3001 (1984); Brodeur et al., Monoclonal Antibody Production Techniques and Applications, pp. 51-63 (Marcel Dekker, Inc., New York, 1987); and Boerner et al., J. Immunol., 147: 86 (1991).) Human antibodies generated via human B-cell hybridoma technology are also described in Li et al., Proc. Natl. Acad. Sci. USA, 103:3557-3562 (2006). Additional methods include those described, for example, in U.S. Pat. No. 7,189,826 (describing production of monoclonal human IgM antibodies from hybridoma cell lines) and Ni, Xiandai Mianyixue, 26(4):265-268 (2006) (describing human-human hybridomas). Human hybridoma technology (Trioma technology) is also described in Vollmers and Brandlein, Histology and Histopathology, 20(3):927-937 (2005) and Vollmers and Brandlein, Methods and Findings in Experimental and Clinical Pharmacology, 27(3):185-91 (2005).

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

5. Library-Derived Antibodies

Antibodies of the invention may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom et al. in Methods in Molecular Biology 178: 1-37 (O'Brien et al., ed., Human Press, Totowa, NJ, 2001) and further described, e.g., in the McCafferty et al., Nature 348:552-554; Clackson et al., Nature 352: 624-628 (1991); Marks et al., J. Mol. Biol. 222: 581-597 (1992); Marks and Bradbury, in Methods in Molecular Biology 248:161-175 (Lo, ed., Human Press, Totowa, NJ, 2003); Sidhu et al., J. Mol. Biol. 338(2): 299-310 (2004); Lee et al., J. Mol. Biol. 340(5): 1073-1093 (2004); Fellouse, Proc. Natl. Acad. Sci. USA 101(34): 12467-12472 (2004); and Lee et al., J. Immunol. Methods 284(1-2): 119-132(2004).

In certain phage display methods, repertoires of VH and VL genes are separately cloned by polymerase chain reaction (PCR) and recombined randomly in phage libraries which can then be screened for antigen-binding phage as described in Winter et al., Ann. Rev. Immunol., 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self antigens without any immunization as described by Griffiths et al., EMBO J, 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, J. Mol. Biol., 227: 381-388 (1992). Patent publications describing human antibody phage libraries include, for example: U.S. Pat. No. 5,750,373, and U.S. Patent Publication Nos. 2005/0079574, 2005/0119455, 2005/0266000, 2007/0117126, 2007/0160598, 2007/0237764, 2007/0292936, and 2009/0002360.

Antibodies or antibody fragments isolated from human antibody libraries are considered human antibodies or human antibody fragments herein.

6. Multispecific Antibodies

In certain embodiments, an antibody provided herein is a multispecific antibody, e.g. a bispecific antibody. Multispecific antibodies are monoclonal antibodies that have binding specificities for at least two different sites. In certain embodiments, one of the binding specificities is for IL-13 and the other is for any other antigen. In certain embodiments, bispecific antibodies may bind to two different epitopes of IL-13. Bispecific antibodies may also be used to localize cytotoxic agents to cells. Bispecific antibodies can be prepared as full length antibodies or antibody fragments.

Techniques for making multispecific antibodies include, but are not limited to, recombinant co-expression of two immunoglobulin heavy chain-light chain pairs having different specificities (see Milstein and Cuello, Nature 305: 537 (1983)), WO 93/08829, and Traunecker et al., EMBO J. 10: 3655 (1991)), and "knob-in-hole" engineering (see, e.g., U.S. Pat. No. 5,731,168). Multi-specific antibodies may also be made by engineering electrostatic steering effects for making antibody Fc-heterodimeric molecules (WO 2009/089004A1); cross-linking two or more antibodies or fragments (see, e.g., U.S. Pat. No. 4,676,980, and Brennan et al., Science, 229: 81 (1985)); using leucine zippers to produce bispecific antibodies (see, e.g., Kostelny et al., J. Immunol., 148(5):1547-1553 (1992)); using "diabody" technology for making bispecific antibody fragments (see, e.g., Hollinger et al., Proc. Natl. Acad. Sci. USA, 90:6444-6448 (1993)); and using single-chain Fv (sFv) dimers (see, e.g. Gruber et al., J. Immunol., 152:5368 (1994)); and preparing trispecific antibodies as described, e.g., in Tutt et al. J. Immunol. 147: 60 (1991).

Engineered antibodies with three or more functional antigen binding sites, including "Octopus antibodies," are also included herein (see, e.g. US 2006/0025576A1).

The antibody or fragment herein also includes a "Dual Acting FAb" or "DAF" comprising an antigen binding site that binds to IL-13 as well as another, different antigen (see, US 2008/0069820, for example).

7. Antibody Variants

In certain embodiments, amino acid sequence variants of the antibodies provided herein are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

Substitution, Insertion, and Deletion Variants

In certain embodiments, antibody variants having one or more amino acid substitutions are provided. Sites of interest for substitutional mutagenesis include the HVRs and FRs. Conservative substitutions are shown in Table 1 under the heading of "conservative substitutions." More substantial changes are provided in Table 1 under the heading of "exemplary substitutions," and as further described below in reference to amino acid side chain classes. Amino acid substitutions may be introduced into an antibody of interest and the products screened for a desired activity, e.g., retained/improved antigen binding, decreased immunogenicity, or improved ADCC or CDC.

TABLE 1

| Original Residue | Exemplary Substitutions | Conservative Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:

(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

One type of substitutional variant involves substituting one or more hypervariable region residues of a parent antibody (e.g. a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, Methods Mol. Biol. 207:179-196 (2008)), and/or SDRs (a-CDRs), with the resulting variant VH or VL being tested for binding affinity. Affinity maturation by constructing and reselecting from secondary libraries has been described, e.g., in Hoogenboom et al. in Methods in Molecular Biology 178:1-37 (O'Brien et al., ed., Human Press, Totowa, NJ, (2001).) In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may be outside of HVR "hotspots" or SDRs. In certain embodiments of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham and Wells (1989) Science, 244:1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

Glycosylation Variants

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. TIBTECH 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

In one embodiment, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e. g. complex, hybrid and high mannose structures) as measured by MALDI-TOF mass spectrometry, as described in WO 2008/077546, for example. Asn297 refers to the asparagine residue located at about position 297 in the Fc region (Eu numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. J. Mol. Biol. 336:1239-1249 (2004); Yamane-Ohnuki et al. Biotech. Bioeng. 87: 614 (2004). Examples of cell lines capable of producing defucosylated antibodies include Lec13 CHO cells deficient in protein fucosylation (Ripka et al. Arch. Biochem. Biophys. 249: 533-545 (1986); U.S. Pat Appl No 2003/0157108 A1, Presta, L; and WO 2004/056312 A1, Adams et al., especially at Example 11), and knockout cell lines, such as alpha-1,6-fucosyltransferase gene, FUT8, knockout CHO cells (see, e.g., Yamane-Ohnuki et al. Biotech. Bioeng. 87: 614 (2004); Kanda, Y. et al., Biotechnol. Bioeng., 94(4):680-688 (2006); and WO2003/085107).

Antibodies variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878 (Jean-Mairet et al.); U.S. Pat. No. 6,602,684 (Umana et al.); and US 2005/0123546 (Umana et al.). Antibody variants with at least one galactose residue in the oligosaccharide attached to the Fc region are also provided. Such antibody variants may have improved CDC function. Such antibody variants are described, e.g., in WO 1997/30087 (Patel et al.); WO 1998/58964 (Raju, S.); and WO 1999/22764 (Raju, S.)

Fc Region Variants

In certain embodiments, one or more amino acid modifications may be introduced into the Fc region of an antibody provided herein, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

In certain embodiments, the invention contemplates an antibody variant that possesses some but not all effector functions, which make it a desirable candidate for applications in which the half-life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII FcR expression on hematopoietic cells is summarized in Table 3 on page 464 of Ravetch and Kinet, Annu. Rev. Immunol. 9:457-492 (1991). Non-limiting examples of in vitro assays to assess ADCC activity of a molecule of interest is described in U.S. Pat. No. 5,500,362 (see, e.g. Hellstrom, I. et al. Proc. Nat'l Acad. Sci. USA 83:7059-7063 (1986)) and Hellstrom, I et al., Proc. Nat'l Acad. Sci. USA 82:1499-1502 (1985); 5,821,337 (see Bruggemann, M. et al., J. Exp. Med. 166:1351-1361 (1987)). Alternatively, non-radioactive assays methods may be employed (see, for example, ACTI™ non-radioactive cytotoxicity assay for flow cytometry (CellTechnology, Inc. Mountain View, CA; and CytoTox 96® non-radioactive cytotoxicity assay (Promega, Madison, WI). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. Proc. Nat'l Acad. Sci. USA 95:652-656 (1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., J. Immunol. Methods 202:163 (1996); Cragg, M. S. et al., Blood 101:1045-1052 (2003); and Cragg, M. S. and M. J. Glennie, Blood 103: 2738-2743 (2004)). FcRn binding and in vivo clearance/half-life determinations can also be performed using methods known in the art (see, e.g., Petkova, S. B. et al., Int'l. Immunol. 18(12):1759-1769 (2006)).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No. 6,737,056; WO 2004/056312, and Shields et al., J. Biol. Chem. 9(2): 6591-6604 (2001).)

In certain embodiments, an antibody variant comprises an Fc region with one or more amino acid substitutions which improve ADCC, e.g., substitutions at positions 298, 333, and/or 334 of the Fc region (EU numbering of residues).

In some embodiments, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al. J. Immunol. 164: 4178-4184 (2000).

Antibodies with increased half-lives and improved binding to the neonatal Fc receptor (FcRn), which is responsible for the transfer of maternal IgGs to the fetus (Guyer et al., J. Immunol. 117:587 (1976) and Kim et al., J. Immunol. 24:249 (1994)), are described in US2005/0014934A1 (Hinton et al.) Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826).

See also Duncan & Winter, Nature 322:738-40 (1988); U.S. Pat. Nos. 5,648,260; 5,624,821; and WO 94/29351 concerning other examples of Fc region variants.

Cysteine Engineered Antibody Variants

In certain embodiments, it may be desirable to create cysteine engineered antibodies, e.g., "THIOMABS," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: V205 (Kabat numbering) of the light chain; A118 (EU numbering) of the heavy chain; and S400 (EU numbering) of the heavy chain Fc region. Cysteine engineered antibodies may be generated as described, e.g., in U.S. Pat. No. 7,521,541.

Antibody Derivatives

In certain embodiments, an antibody provided herein may be further modified to contain additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1, 3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, polypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer is attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and nonproteinaceous moiety that may be selectively heated by exposure to radiation are provided. In one embodiment, the nonproteinaceous moiety is a carbon nanotube (Kam et al., Proc. Natl. Acad. Sci. USA 102: 11600-11605 (2005)). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

Recombinant Methods and Compositions

Antibodies may be produced using recombinant methods and compositions, e.g., as described in U.S. Pat. No. 4,816,567. In one embodiment, isolated nucleic acid encoding an antibody described herein is provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, e.g. a Chinese Hamster Ovary (CHO) cell or lymphoid cell (e.g., YO, NSO, Sp20 cell). In one embodiment, a method of making an antibody is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an antibody, nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, Methods in Molecular Biology, Vol. 248 (B. K. C. Lo, ed., Humana Press, Totowa, NJ, 2003), pp. 245-254, describing expression of antibody fragments in E. coli.) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, Nat. Biotech. 22:1409-1414 (2004), and Li et al., Nat. Biotech. 24:210-215 (2006).

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of Spodoptera frugiperda cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., J. Gen Virol. 36:59 (1977)); baby hamster kidney cells (BHK); mouse sertoli cells (TM4 cells as described, e.g., in Mather, Biol. Reprod. 23:243-251 (1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., Annals N.Y. Acad. Sci. 383:44-68 (1982); MRC 5 cells; and FS4 cells. Other useful mammalian host cell lines include Chinese hamster ovary (CHO) cells, including DHFR-CHO cells (Urlaub et al., Proc. Natl. Acad. Sci. USA 77:4216 (1980)); and myeloma cell lines such as YO, NSO and Sp2/0. For a review of certain mammalian host cell lines suitable for antibody production, see, e.g., Yazaki and Wu, Methods in Molecular Biology, Vol. 248 (B. K. C. Lo, ed., Humana Press, Totowa, NJ), pp. 255-268 (2003).

Pharmaceutical Formulations

Pharmaceutical formulations, also referred to herein as pharmaceutical compositions, of an anti-IL-13 antibody as described herein are prepared by mixing such antibody or molecule having the desired degree of purity with one or more optional pharmaceutically acceptable carriers (Remington's Pharmaceutical Sciences 16th edition, Osol, A. Ed. (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/ or non-ionic surfactants such as polyethylene glycol (PEG). Exemplary pharmaceutically acceptable carriers herein further include insterstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

Exemplary lyophilized antibody formulations are described in U.S. Pat. No. 6,267,958. Aqueous antibody formulations include those described in U.S. Pat. No. 6,171, 586 and WO2006/044908, the latter formulations including a histidine-acetate buffer.

The formulation herein may also contain more than one active ingredients as necessary for the particular indication being treated, preferably those with complementary activities that do not adversely affect each other. For example, it may be desirable to further provide a controller with the Th2 pathway inhibitor. Such active ingredients are suitably present in combination in amounts that are effective for the purpose intended.

Active ingredients may be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Sustained-release preparations may be prepared. Suitable examples of sustained-release preparations include semipermeable matrices of solid hydrophobic polymers containing the antibody, which matrices are in the form of shaped articles, e.g. films, or microcapsules.

The formulations to be used for in vivo administration are generally sterile. Sterility may be readily accomplished, e.g., by filtration through sterile filtration membranes.

Therapeutic Methods and Compositions

In certain embodiments, methods of treating atopic dermatitis comprising administering a therapeutically effective amount of lebrikizumab to the atopic dermatitis patient, wherein the treatment results in a reduction in disease severity as measured or assessed by an Atopic Dermatitis Disease Severity Outcome Measure (ADDSOM) are provided. In some embodiments, the atopic dermatitis is moderate to severe as determined by Rajka/Langeland criteria score. A Rajka/Langeland criteria score between 4.5 and 9 is typically considered moderate to severe atopic dermatitis. In some embodiments, the methods further comprise administration of one or more topical corticosteroids. Topical corticosteroids may be administered before (i.e., prior to) administration of the IL-13 antagonist, at the same time as administration of the IL-13 antagonist, or after administration of the IL-13 antagonist. Exemplary topical corticosteroids include, but are not limited to, triamcinolone acetonide, hydrocortisone, and a combination of triamcinolone acetonide and hydrocortisone. Triamcinolone acetonide is typically formulated at a concentration of 0.1% in a cream, and hydrocortisone is typically formulated at a concentration of 1% or 2.5% in a cream. Certain topical corticosteroids are considered very high potency such as, for example, betamethasone dipropionate, clobetasol propionate, diflorasone diacetate, fluocinonide, and halobetasol propionate. Certain topical corticosteroids are considered high potency such as, for example, amcinonide, desoximetasone, halcinonide, and triamcinolone acetonide. Certain topical corticosteroids are considered medium potency, such as, for example, betamethasone valerate, clocortolone pivalate, fluocinolone acetonide, flurandrenolide, fluocinonide, fluticasone propionate, hydrocortisone butyrate, hydrocortisone valerate, mometasone furoate, and prednicarbate. Certain topical corticosteroids are considered low potency, such as, for example, alclometasone dipropionate, desonide, and hydrocortisone. TCS may be applied to affected areas once daily, twice daily, three times per day, or as needed. In some embodiments, the patient is inadequately controlled on topical corticosteroids.

Various ADDSOMs are known in the art and are described herein in addition to a novel Atopic Dermatitis Impact Questionnaire (ADIQ). Exemplary ADDSOMs include, but are not limited to, "Eczema Area and Severity Index" (EAST), "Severity Scoring of Atopic Dermatitis" (SCORAD), "Investigator Global Assessment" (IGA), "Investigator Global Assessment of Signs" (IGSA), Rajka/Langeland Atopic Dermatitis Severity Score, and Patient-Reported Outcomes including, but not limited to, Pruritus Visual Analog Scale (an aspect of disease severity assessed as part of SCORAD), Sleep Loss Visual Analog Scale (an aspect of disease severity assessed as part of SCORAD), Atopic Dermatitis Symptom Diary (ADSD), Atopic Dermatitis Impact Questionnaire (ADIQ), Dermatology Life Quality Index (DLQI) (Finlay and Khan, Clin Exper Dermatol 1994; 19:210), and 5-D Itch Scale (Elman et al., Br J Dermatol 2010; 162(3):587-593).

A therapeutic agent as provided herein can be administered by any suitable means, including parenteral, subcutaneous, intraperitoneal, intrapulmonary, and intranasal. Parenteral infusions include intramuscular, intravenous, intraarterial, intraperitoneal, or subcutaneous administration. In certain embodiments, the dosing is given by injections, e.g., intravenous or subcutaneous injections. In yet another embodiment, the therapeutic agent is administered using a syringe (e.g., prefilled or not) or an autoinjector. In certain embodiments, the therapeutic agent is applied topically.

In certain embodiments, an anti-IL13 antibody of the invention is administered using, for example, a self-inject device, autoinjector device, or other device designed for self-administration. In certain embodiments, an anti-IL13 antibody of the invention is administered using a subcutaneous administration device. Various self-inject devices and subcutaneous administration devices, including autoinjector devices, are known in the art and are commercially available. Exemplary devices include, but are not limited to, prefilled syringes (such as BD HYPAK SCF®, READY-FILL™, and STERIFILL SCF™ from Becton Dickinson; CLEARSHOT™ copolymer prefilled syringes from Baxter; and Daikyo Seiko CRYSTAL ZENITH® prefilled syringes available from West Pharmaceutical Services); disposable pen injection devices such as BD Pen from Becton Dickinson; ultra-sharp and microneedle devices (such as INJECT-EASE™ and microinfuser devices from Becton Dickinson; and H-PATCH™ available from Valeritas) as well as needle-free injection devices (such as BIOJECTOR® and IJECT® available from Bioject; and SOF-SERTER® and patch devices available from Medtronic). In certain embodiments, an anti-IL-13 antibody of the invention is administered using an autoinjector device comprised of various components, for example, as described in US Patent Publication Nos. 2014/0114247, 2014/0148763, and 2013/0131590; U.S. Pat. Nos. 7,597,685, 7,896,850, and 8,617,109, all of which are incorporated by reference. Co-formulations or co-administrations with such self-inject devices or subcutaneous administration devices of an anti-IL13 antibody with at least a second therapeutic compound are envisioned.

For the prevention or treatment of disease, the appropriate dosage of an antibody of the invention (when used alone or in combination with one or more other additional therapeutic agents) will depend on the type of disease to be treated, the type of antibody, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments. In certain embodiments, the antibody of the invention is administered as a flat dose (not a weight-based dose) of 125 mg or 250 mg or about 125 mg or about 250 mg or a flat dose between 110 mg to 140 mg or a flat dose between 120 mg to 130 mg or a flat dose between 225 mg to 275 mg or a flat dose between 240 mg to 260 mg. In certain embodiments, the dose is administered by subcutaneous injection once every four weeks or once every eight weeks for a period of time. In certain embodiments, the period of time is 12 weeks, or 20 weeks, or 24 weeks, or 9 months, or one year, two years, five years, ten years, 15 years, 20 years, or the lifetime of the patient. The progress of this therapy is easily monitored by conventional techniques and assays. In certain embodiments, the patient has moderate to severe atopic dermatitis and the patient administers TCS as needed while being treated with the antibody of the invention. In certain embodiments, the TCS is administered once a day, or twice a day, or three times a day or more. In certain embodiments, the patient is able to decrease usage of TCS over time while the antibody of the invention is being administered. Such decreased usage of TCS is referred to as "tapering" or "TCS-sparing." The time period over which decreased usage may occur is one, two, three, or four weeks, or two, three, four, five, or six months.

IL-13 antagonists of the invention, according to certain embodiments, comprise administration in combination with one or more additional therapeutic agents. The term "in combination with" means that the additional therapeutic agent(s) are administered before, after, or concurrent with the pharmaceutical composition comprising the IL-13 antagonist. The term "in combination with" also includes sequential or concomitant administration of IL-13 antagonist and a second therapeutic agent.

For example, when administered "before" the pharmaceutical composition comprising the IL-13 antagonist, the additional therapeutic agent may be administered about 72 hours, about 60 hours, about 48 hours, about 36 hours, about 24 hours, about 12 hours, about 10 hours, about 8 hours, about 6 hours, about 4 hours, about 2 hours, about 1 hour, about 30 minutes, about 15 minutes or about 10 minutes prior to the administration of the pharmaceutical composition comprising the IL-13 antagonist. When administered "after" the pharmaceutical composition comprising the IL-13 antagonist, the additional therapeutic agent may be administered about 10 minutes, about 15 minutes, about 30 minutes, about 1 hour, about 2 hours, about 4 hours, about 6 hours, about 8 hours, about 10 hours, about 12 hours, about 24 hours, about 36 hours, about 48 hours, about 60 hours or about 72 hours after the administration of the pharmaceutical composition comprising the IL-13 antagonist. Administration "concurrent" or with the pharmaceutical composition comprising the IL-13 antagonist means that the additional therapeutic agent is administered to the subject in a separate dosage form within less than 5 minutes (before, after, or at the same time) of administration of the pharmaceutical composition comprising the IL-13 antagonist, or administered to the subject as a single combined dosage formulation comprising both the additional therapeutic agent and the IL-13 antagonist.

The additional therapeutic agent may be, e.g., another IL-13 antagonist, an IL-4R antagonist, an IL-1 antagonist, an IL-6 antagonist, an IL-6R antagonist, a TNF antagonist, an IL-8 antagonist, an IL-9 antagonist, an IL-17 antagonist, an IL-5 antagonist, an IgE antagonist, a CD48 antagonist, an IL-31 antagonist, a thymic stromal lymphopoietin (TSLP) antagonist, interferon-gamma (IFN.gamma.) antibiotics, topical corticosteroids, tacrolimus, pimecrolimus, mycophenolate, cyclosporine, azathioprine, methotrexate, cromolyn sodium, proteinase inhibitors, or combinations thereof. In certain embodiments, the pharmaceutical composition comprising an anti-IL13 antagonist is administered to a subject in conjunction with an oral immunosuppressant, a topical calcineurin inhibitor, such as for example, pimecrolimus or tacrolimus, or an oral corticosteroid, such as, for example, prednisolone. In certain embodiments, the pharmaceutical composition comprising an anti-IL13 antagonist is administered to a subject in conjunction with a non-pharmaceutical therapy such as ultraviolet (UV) light therapy.

In certain embodiments, an antibody of the invention is administered one or more times as a flat (i.e., not weight dependent) loading dose followed by administration one or more times as a flat maintenance dose. In certain embodiments, the loading dose is 250 mg or 500 mg and the maintenance dose 125 mg. In certain embodiments, two loading doses of 250 mg are administered 15 days apart or 29 days apart. In certain embodiments, the maintenance dose is administered two weeks after the last loading dose or four weeks after the last loading dose and then every four weeks thereafter. In certain embodiments, the loading dose is 500 mg and the maintenance dose is 250 mg. In certain embodiments, the maintenance dose of 250 mg is administered four weeks after the loading dose and then every four weeks or every eight weeks thereafter.

Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, autoinjectors etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is an antibody of the invention. The label or package insert indicates that the composition is used for treating the condition of choice. Moreover, the article of manufacture may comprise (a) a first container with a composition contained therein, wherein the composition comprises an antibody of the invention; and (b) a second container with a composition contained therein, wherein the composition comprises a further therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, syringes, and autoinjectors.

EXAMPLES

Example 1

Anti-IL-13 Antibodies

Anti-IL-13 antibodies, including monoclonal humanized anti-IL-13 antibodies, have been described previously (see, e.g., WO2005062967). One monoclonal humanized anti-IL-13 antibody described therein is lebrikizumab, an IgG4 antibody, see also Sequence Listing Table. Lebrikizumab was used in the studies described below, formulated at 125 mg/mL in a pharmaceutically acceptable composition and supplied in a prefilled syringe.

Example 2

Clinical Study I

Clinical Study I was a phase II, randomized, double-blind, placebo-controlled study to evaluate the safety and efficacy of lebrikizumab in patients (age 18-75) with persistent moderate to severe atopic dermatitis that is inadequately controlled by topical corticosteroids (TCS). In this Study, lebrikizumab was tested in combination with TCS. The Study Schema is provided in FIG. 1.

Screening. Patients eligible to enroll in the Study had to have moderate to severe AD present for at least 1 year and had to meet all eligibility criteria. Patients were evaluated at screening to assess eligibility for entry into the run-in period and again at the end of the run-in period, to assess eligibility for entry into the treatment period and randomization to study drug.

The inclusion criteria included the following: age 18 to 75 years; AD diagnosed by the Hanifin/Rajka criteria and that had been present for at least 1 year at screening; moderate to severe AD as graded by the Rajka/Langeland criteria at screening; history of inadequate response to a 1 month (within the 3 months prior to the screening visit) treatment regimen of at least daily TCS and regular emollient for treatment of AD; EASI score 14 at screening and end of the run-in period (Visit 3), IGA score 3 (5-point scale) at screening and end of the run-in period (Visit 3); AD involvement of 10% body surface area (BSA) at screening; and Pruritus VAS score (measured as part of the SCORAD) of 3 at screening.

Exclusion criteria included the following: past and/or current use of any anti-IL-13 or anti-IL-4/IL-13 therapy, including lebrikizumab; use of an investigational agent within 4 weeks prior to screening or within 5 half-lives of the investigational agent, whichever is longer; history of a severe allergic reaction or anaphylactic reaction to a biologic agent or known hypersensitivity to any component of the lebrikizumab injection; hypersensitivity to TCS or to any other ingredients contained by the TCS product used in the study; use of any complementary, alternative, or homeopathic medicines including, but not limited to, phytotherapies, traditional or non-traditional herbal medications, essential fatty acids, or acupuncture within 7 days prior to the run-in period or need for such medications during the study; body weight <40 kg or body mass index >38 kg/m$^2$;

evidence of other skin conditions; including, but not limited to, T-cell lymphoma or allergic contact dermatitis; evidence of, or ongoing treatment (including topical antibiotics) for active skin infection at screening (Day −15); certain infections; history of recent (<1 year) parasitic infections, especially nematodes (e.g., Ascaris, Ancylostoma), Platyhelminthes (e.g., Schistosoma), or history of Listeria infections; active tuberculosis requiring treatment within the 12 months prior to Visit 1; evidence of acute or chronic hepatitis or known liver cirrhosis; known immunodeficiency, including HIV infection; use of TCI (topical calcineurin inhibitor) at the time of screening; use of a tanning booth/parlor within 4 weeks before the screening visit; allergen immunotherapy within 3 months of screening; receipt of a live attenuated vaccine within 4 weeks prior to baseline visit (Day 1); planned surgery during the study; clinically significant abnormality on screening ECG or laboratory tests (hematology, serum chemistry, and urinalysis); AST, ALT, or total bilirubin elevation ≥2.0×the upper limit of normal (ULN) during screening; known current malignancy or current evaluation for a potential malignancy, including basal or squamous cell carcinoma of the skin or carcinoma in situ; history of malignancy within 5 years prior to screening, except for appropriately treated carcinoma in situ of the cervix, non-melanoma skin carcinoma; stage I uterine cancer; and other clinically significant medical disease that is uncontrolled despite treatment.

Run-in Period. Following the screening visit, eligible patients entered a 2-week run-in period (Days −14 to −1) during which a protocol-specified topical therapy regimen was initiated. On the first day of the run-in period (Day −14) patients received TCS for use throughout the run-in period. Patients were required to apply the following topical therapy regimen daily: emollient to all xerotic skin surfaces, at least once daily; TCS cream consisting of medium potency TCS (triamcinolone acetonide 0.1%), two times per day, only to all active skin lesions. For lesions affecting the face or intertriginous areas, low potency TCS (hydrocortisone 2.5% cream) could be used instead of triamcinolone acetonide 0.1%, at the discretion of the investigator.

At the end of the run-in period, a second assessment of eligibility for randomization to study drug (lebrikizumab or placebo) was performed and patients must have continued to demonstrate moderate to severe AD as assessed by EASI score ≥14 and IGA score ≥3.

Treatment Period. At the end of the run-in period, patients who had: 1) demonstrated compliance with the protocol-specified TCS regimen, and 2) who continued to fulfill the eligibility criteria as described above were randomized. The plan was to randomize approximately 200 patients (1:1:1:1) to one of the following four treatment groups (see FIG. 1): (1) Group 1: lebrikizumab 250 mg administered subcutaneously (SC) single dose (Day 1) followed by 2 placebo doses (at Week 4 and at Week 8) for a total of 3 doses+TCS cream; (2) Group 2: lebrikizumab 125 mg SC single dose (Day 1) followed by 2 placebo doses (Week 4 and Week 8) for a total of 3 doses+TCS cream; (3) Group 3: lebrikizumab 125 mg SC every 4 weeks (Q4W) for a total of 3 doses+TCS cream; and (4) Group 4: placebo SC Q4W for a total of 3 doses+ TCS cream. Three active doses were included to characterize both exposure-response relationships and dosing frequency requirements.

Patients randomized to these four study treatment groups received study drug (lebrikizumab or placebo SC) in combination with TCS. Throughout the 12-week treatment period these patients continued to apply emollient at least once daily and triamcinolone acetonide 0.1% cream as described in the run-in period (two times per day to all active skin lesions on the body). For lesions affecting the face or intertriginous areas, low potency TCS (hydrocortisone 2.5% cream) could have been used instead of triamcinolone acetonide 0.1%, at the discretion of the investigator. Patients recorded their use of topical creams and responded to PRO-related questions using a hand held eDiary throughout the treatment period. At each study visit the patient was required to bring their TCS containers to the study site to be weighed.

Safety Follow-Up Period. All patients who completed study treatment during the placebo-controlled treatment period (Weeks 1-12) were followed for safety for an additional 8 weeks (Weeks 13-20). During this safety follow-up period, patients were no longer required to apply the topical treatment regimen as specified during the run-in and treatment periods. Instead, triamcinolone acetonide 0.1% cream and/or hydrocortisone 2.5% cream could be applied as determined by the patient and the study investigator. At each study visit the patient was required to bring their TCS containers to the study site to be weighed. Patients were encouraged to continue applying emollients at least once daily to xerotic skin. An escalation in therapy for AD was allowed at any during the study, if, in the opinion of the investigator, it was clinically indicated.

Topical calcineruin inhibitors (TCIs) were not allowed at any time during this study. Patients who had been using TCIs at the time of screening were allowed to participate in the study if they agreed to stop using TCIs during the study and if, in the opinion of the investigator, it was safe to stop the use of TCI and use the protocol specified TCS cream instead.

Rationale for Lebrikizumab Dose and Schedule. The dose of lebrikizumab for AD was based on the clinical experience with the asthma program and the similarities in IL-13 biology and the expected PK characteristics of lebrikizumab in the two patient populations. Both AD and asthma patients have elevated levels of biomarkers associated with IL-13 biology and Th-2 mediated hypersensitivity. In particular, IL-13 is elevated in the lungs of asthma patients and has a pathogenic role in asthma, while increased expression of IL-13 has consistently been reported in AD skin.

Additionally, given that the primary clearance mechanism of lebrikizumab is through nonspecific endocytosis and catabolism, with minimal contribution of target-mediated clearance, the PK characteristics of lebrikizumab are expected to be similar between asthma and AD patients. Although limited information exists in the literature regarding the partitioning of monoclonal antibodies to various tissues, available data in animal models suggest similar plasma-to-tissue partitioning coefficients for monoclonal antibodies in the lung and skin tissue (Shah D K et al., mAbs 2013; 5(2):297-305). Therefore, the dose levels of lebrikizumab producing clinical benefit in asthma may also produce biological activity in AD patients.

As described above, three different dose regimens were tested in this Phase II study: (1) the 125 mg Q4W dose (Group 3) was included as a potentially effective dose. 125-mg Q4W was the highest dose regimen (i.e. highest total exposure) being studied in the pivotal Phase III adult studies of lebrikizumab in asthma (LAVOLTA I and II) that were ongoing at the time of study initiation. Given the expected similarity in the role of IL-13 and the pharmacokinetics between asthma and AD, it was hypothesized that this dose could be effective in patients with AD; (2) a single 250 mg dose (Group 1) was proposed as an alternative potentially effective dose. This dose was expected to produce a lower overall exposure than 125 mg Q4W over the first 12 weeks. With the primary endpoint at Week 12, a single 250 mg dose was tested to explore the potential for quarterly dosing; and (3) a single 125 mg dose (Group 2) was proposed as a potentially partially effective dose. Given that the overall exposure at this dose was expected to be 2-3-fold lower than that of the 125 mg Q4W and 250 mg single dose regimens, data from all three dose arms can be used to characterize the exposure-response relationships of lebrikizumab in AD patients.

As described above, however, the results of the LAVOLTA I and II studies were inconsistent. Hanania et al., Lancet Respir Med 2016, available at dx(dot)doi(dot)org (slash)52213-2600(16)30265-X, published online Sep. 5, 2016. Both studies failed to show a clear dose-response although pharmacokinetic and pharmacodynamics results were consistent with those from the phase II studies described previously, indicating that drug exposures were similar and that the IL-13 pathway was inhibited. Hanania et al., 2016, supra. Accordingly, it was uncertain whether lebrikizumab would provide clinically meaningful benefit to atopic dermatitis patients at the dosing regimens described herein.

The primary endpoint for the Phase II study was measured at Week 12. The mean serum lebrikizumab trough concentration at Week 12 was expected to be over 90% of the steady state value for patients receiving 125 mg Q4W. In addition, for the 125 mg Q4W dose, the predicted trough concentrations at Week 12 would be well within the range where lebrikizumab demonstrated biological activity in the Phase II asthma clinical trials. For the 250 mg single dose, the predicted average exposure over 12 weeks is above that of a 37.5 mg Q4W regimen, which also demonstrated biological activity in Phase II asthma trials; Hanania et al., Thorax 2015; 70:748-756.

Rationale for Control Group. Patients in treatment Group 4 received placebo SC+TCS cream and therefore served as an active comparator. This treatment group was used as a control for lebrikizumab SC to adequately assess the efficacy and safety effect of lebrikizumab as adjunctive therapy with TCS.

The active TCS comparator group was included since TCS use is the standard of care in clinical practice and is continued while step-up therapies (e.g., systemic agents) are initiated (European Academy of Dermatology and Venereology [EADV] 2009 guidelines; Darsow et al., J Eur Acad Dermatol Venereol 2010; 24:317-28). In addition, stopping TCS in patients with persistent moderate to severe disease may result in significant worsening of AD symptoms and disease burden.

Efficacy Outcome Measures. The primary efficacy outcome measure was the percentage of patients achieving EASI-50 (a 50% reduction in EASI score from baseline) at Week 12. The secondary efficacy outcome measures for this study were as follows: (i) percent and absolute change from baseline in EASI score at Week 12; (ii) percent of patients achieving a 75% reduction from baseline in EASI score (EASI-75) at Week 12; (iii) percent of patients achieving an IGA score of 0 or 1 at Week 12; (iv) percent of patients with a 2 point reduction from baseline in IGA at Week 12; (v) absolute change from baseline in IGA at Week 12; (vi) percent of patients achieving an IGSA score of 0 or 1 at Week 12; (vii) percent of patients with a 2 point reduction from baseline in IGSA at Week 12; (viii) absolute change from baseline in IGSA at Week 12; (ix) percent and absolute change from baseline in SCORAD at Week 12; (x) percent of patients with a 50% or 75% reduction from baseline in SCORAD-50/75 at Week 12; (xi) percent of patients achieving EASI-50 at Week 12 and maintaining EASI-50 at Weeks 16 and 20; (xii) percent of patients achieving IGA score of 0 or 1 at Week 12 and maintaining IGA score of 0 or 1 at Weeks 16 and 20; (xiii) percent of patients achieving IGSA score of 0 or 1 at Week 12 and maintaining IGSA score of 0 or 1 at Weeks 16 and 20; (xiv) percent of patients achieving SCORAD-50 at Week 12 and maintaining SCORAD-50 at Weeks 16 and 20; (xv) percent change from baseline in total % body surface area (BSA) affected at Week 12; (xvi) absolute- and percent-change from baseline in pruritus as measured by the Pruritus VAS (assessed as part of the SCORAD) at Week 12; (xvii) absolute- and percent-change from baseline in pruritus as measured by the 5-D Itch Scale at Week 12; (xviii) total use (grams) of TCS from baseline to Week 12; (xvix) total use (grams) of TCS from Week 12 to end of study or early termination; (xx) number of disease flares from baseline to Week 12; (xxi) change in AD symptoms from baseline to Week 12, as assessed by the ADSD; (xxii) change in AD-specific health-related QoL from baseline to Week 12, as assessed by the ADIQ; and (xxiii) change in health-related QoL from baseline to Week 12, as measured by the DLQI.

Safety Outcome Measures. The safety outcome measures for this study were as follows: (i) frequency and severity of treatment-emergent adverse events; (ii) incidence of human anti-therapeutic antibodies (ATA) at baseline and during the study; (iii) frequency and severity of skin and other organ system infections throughout the study; the clinical definition of skin infection was as follows: the diagnosis of infection was based on the Investigator's clinical assessment including but not limited to the presence of honey-colored crusting, serous discharge, pustules, or pain at the site of rash and that may be associated with systemic features, including fever or a flare in AD disease (defined above); and (iv) incidence of disease rebound following discontinuation of study drug as assessed by the investigator; the clinical definition of disease rebound was: a significant worsening of disease severity after cessation of therapy to a severity level that is greater than prior to commencing therapy (Hijnen et al., J Eur Acad Dermatol Venereol 2007; 21(1) 85-9).

Atopic Dermatitis Impact Questionnaire (ADIQ). We developed an AD-specific health-related quality of life tool for use in patients aged 12 years and older following U.S. Food and Drug Administration patient-reported outcome (PRO) guidance (available online at www(dot)fda(dot)gov (slash)downloads(slash)Drugs(slash)Guidances(slash) UCM193282(dot) pdf. Specifically, a literature review was conducted to assess the AD PRO landscape. Concept elicitation (CE) interviews with adults ages 18-75 (n=15) and adolescents 12-17 (n=15) with moderate or severe AD were conducted to elicit signs and symptoms of AD that are important to patients. A grounded theory approach was used to qualitatively analyze interview transcripts. An item generation meeting (IGM) was held to review the data and develop the preliminary ADIQ based on patient feedback from the CE interviews.

The draft ADIQ was tested in cognitive interviews with 34 adult and adolescent patients who confirmed clarity and relevance of the concepts included in the ADIQ, shown in Table 2 below. The psychometric validation is not included.

TABLE 2

Atopic Dermatitis Impact Questionnaire (ADIQ).
Please select the response that best describes how you have been
during the past 7 days with regards to your atopic dermatitis.

| Question | Response Choices |
| --- | --- |
| 1. Over the last 7 days, how depressed were you because of your atopic dermatitis? | 0 = Not at all depressed<br>1 = A little depressed<br>2 = Somewhat depressed<br>3 = Quite a bit depressed<br>4 = Extremely depressed |
| 2. Over the last 7 days, how anxious were you because of your atopic dermatitis? | 0 = Not at all anxious<br>1 = A little anxious<br>2 = Somewhat anxious<br>3 = Quite a bit anxious<br>4 = Extremely anxious |
| 3. Over the last 7 days, how angry were you because of your atopic dermatitis? | 0 = Not at all angry<br>1 = A little angry<br>2 = Somewhat angry<br>3 = Quite a bit angry<br>4 = Extremely angry |
| 4. Over the last 7 days, how frustrated were you because of your atopic dermatitis | 0 = Not at all frustrated<br>1 = A little frustrated<br>2 = Somewhat frustrated<br>3 = Quite a bit frustrated<br>4 = Extremely frustrated |
| 5. Over the last 7 days, how embarrassed were you when you were around other people because of your atopic dermatitis? | 0 = Not at all embarrassed<br>1 = A little embarrassed<br>2 = Somewhat embarrassed<br>3 = Quite a bit embarrassed<br>4 = Extremely embarrassed |
| 6. Over the last 7 days, how self-conscious were you because of your atopic dermatitis? | 0 = Not at all self-conscious<br>1 = A little self-conscious<br>2 = Somewhat self-conscious<br>3 = Quite a bit self-conscious<br>4 = Extremely self-conscious |
| 7. Over the last 7 days, how much has your atopic dermatitis affected your self-esteem? | 0 = Not at all<br>1 = A little<br>2 = Somewhat<br>3 = Quite a bit<br>4 = A lot |
| 8. Over the last 7 days, how much has your atopic dermatitis interfered with your sex life? | 0 = Not at all<br>1 = A little<br>2 = Somewhat<br>3 = Quite a bit<br>4 = A lot |
| 9. Over the last 7 days, how tired did you feel because of your atopic dermatitis? | 0 = Not at all tired<br>1 = A little tired<br>2 = Somewhat tired<br>3 = Quite a bit tired<br>4 = Extremely tired |
| 10. Over the last 7 days, how much difficulty did you have falling asleep because of your atopic dermatitis? | 0 = None<br>1 = A little<br>2 = Some<br>3 = Quite a bit<br>4 = A lot |
| 11. Over the last 7 days, how much did your atopic dermatitis interfere with your ability to work at your job or at school? | 0 = None<br>1 = A little<br>2 = Some<br>3 = Quite a bit<br>4 = A lot |
| 12. Over the last 7 days, how often did you miss work or school because of your atopic dermatitis? | 0 = None of the time<br>1 = A little of the time<br>2 = Some of the time<br>3 = Most of the time<br>4 = All of the time |
| 13. Over the last 7 days, how often did you stay at home because of your atopic dermatitis? | 0 = None of the time<br>1 = A little of the time<br>2 = Some of the time<br>3 = Most of the time<br>4 = All of the time |
| 14. Over the last 7 days, how often did you avoid crowded placed because of your atopic dermatitis? | 0 = None of the time<br>1 = A little of the time<br>2 = Some of the time<br>3 = Most of the time<br>4 = All of the time |

TABLE 2-continued

Atopic Dermatitis Impact Questionnaire (ADIQ).
Please select the response that best describes how you have been
during the past 7 days with regards to your atopic dermatitis.

| Question | Response Choices |
|---|---|
| 15. Over the last 7 days, how much did your atopic dermatitis interfere with your relationships with friends? | 0 = Not at all<br>1 = A little<br>2 = Somewhat<br>3 = Quite a bit<br>4 = A lot |
| 16. Over the last 7 days, how much did your atopic dermatitis interfere with your social activities? | 0 = Not at all<br>1 = A little<br>2 = Somewhat<br>3 = Quite a bit<br>4 = A lot |
| 17. Over the last 7 days, how often were you unable to wear the clothes you wanted to wear because of your atopic dermatitis? | 0 = None of the time<br>1 = A little of the time<br>2 = Some of the time<br>3 = Most of the time<br>4 = All of the time |

Results

Figure 11A:
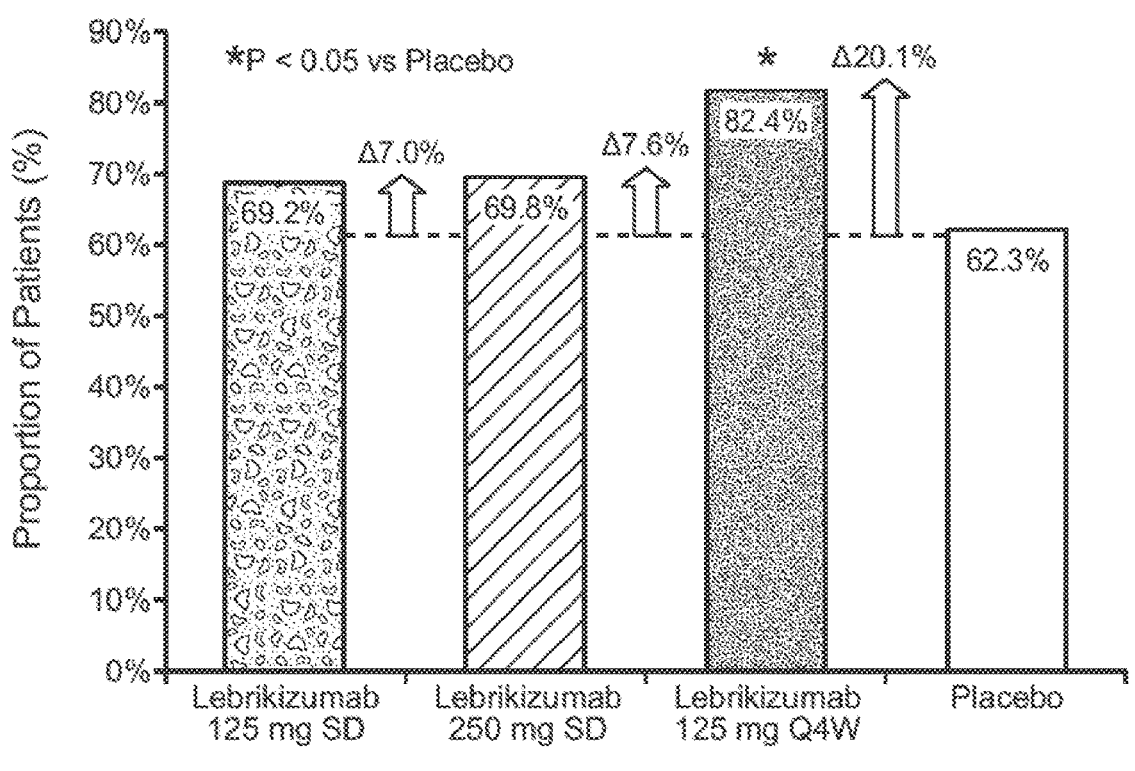
FIGS. 11A-11D show the proportion of patients achieving EASI-50 (FIG. 11A), EASI-75 (FIG. 11B), IGA 0/1 (FIG. 11C), and SCORAD-50 (FIG. 11D) at Week 12 as described in Example 2 and the change in the proportion of patients achieving EASI-50, EASI-75, IGA 0/1, and SCORAD-50, respectively, in each arm of the study compared to placebo is indicated by the dotted line and arrows adjacent to each bar in each of FIGS. 11A-11D. Abbreviations are as follows: EASI=Eczema Area Severity Index; IGA=Investigator Global Assessment; Q4W=every 4 weeks; SCORAD=SCORing Atopic Dermatitis; SD=single dose. Spotted bar=lebrikizumab 125 mg single dose plus topical corticosteroids (TCS) twice per day (BID); hatched bar=lebrikizumab 250 mg single dose plus TCS twice per day; stippled bar=lebrikizumab 125 mg once every 4 weeks (Q4W) plus TCS twice per day; open bar=placebo plus TCS twice per day.
Figure 11B:
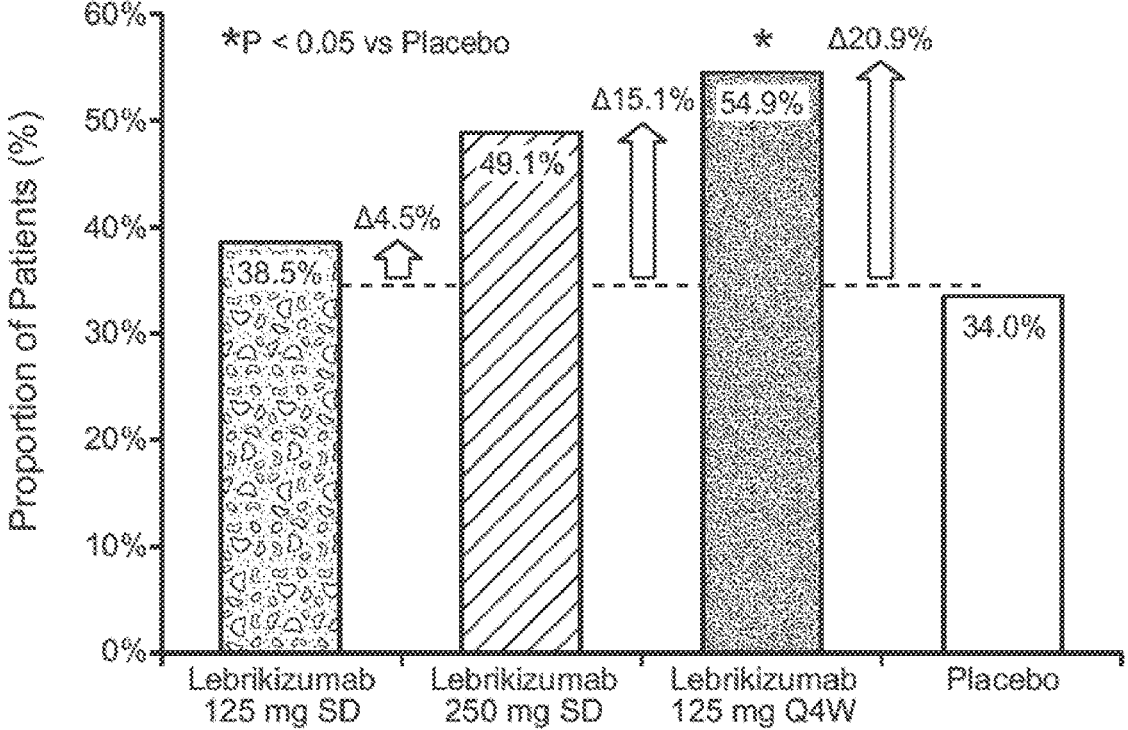
Figure 11C:
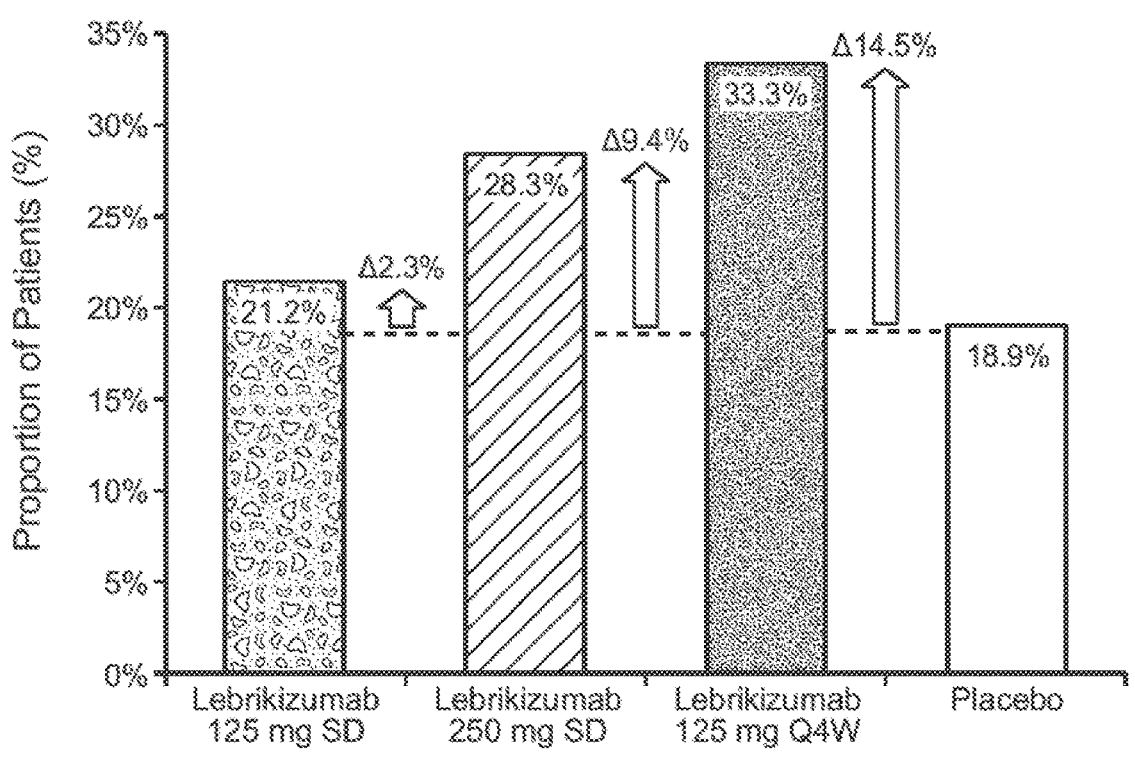
Figure 11D:
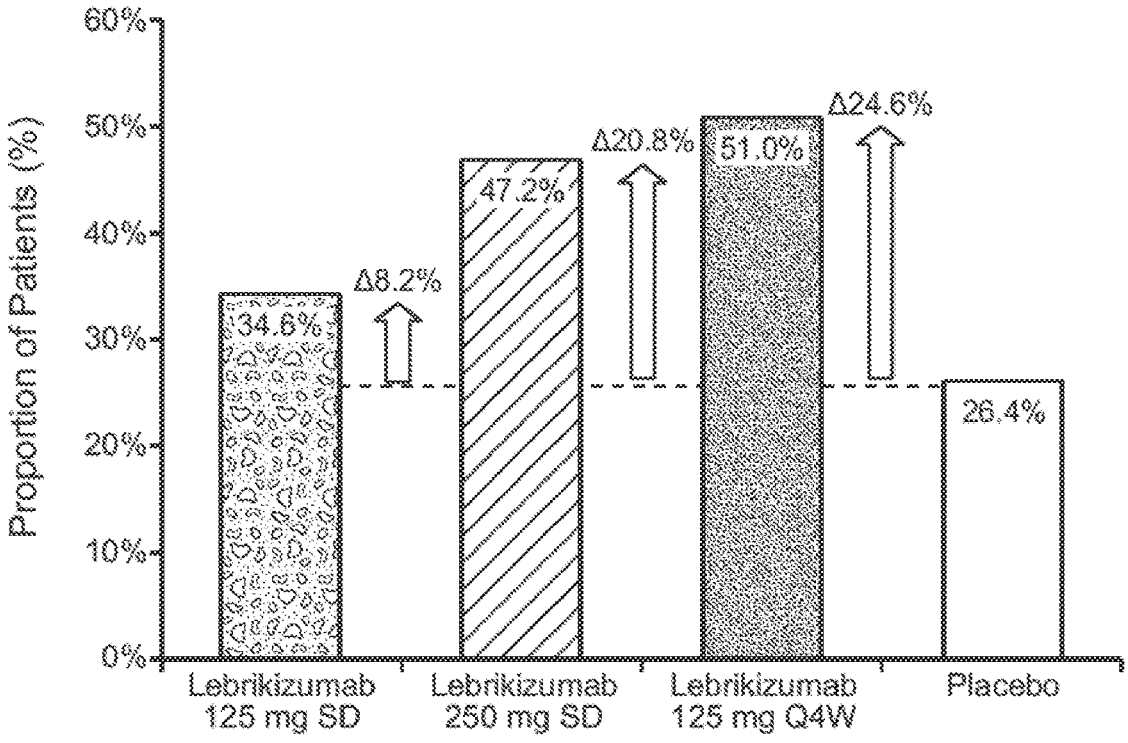

In this study, 209 patients were treated. At Week 12, a greater proportion of patients treated with lebrikizumab (125 mg every four weeks) plus TCS achieved EASI-50 (FIG. 2A and FIG. 3A), EASI-75 (FIG. 3B), EASI-90 (FIG. 3C) and SCORAD-50 (FIG. 2B) compared with placebo. In addition, At Week 12, the percentage of patients who achieved EASI-50, the primary efficacy outcome, was greater for all lebrikizumab groups compared with placebo (62.3%), but only achieved statistical significance in the multiple-dose arm (82.4% [p=0.026] for the 125 mg Q4W arm) as shown in FIG. 11A. Overall, the proportion of patients achieving an EASI-75 response, a secondary efficacy outcome, was greater in all lebrikizumab dose groups, but was significantly greater only in the 125 mg Q4W group (54.9% [p=0.036]) compared with placebo (34.0%) at Week 12 as shown in FIG. 11B. The percentage of patients who achieved IGA 0/1 at Week 12 was higher in all lebrikizumab groups compared with placebo, but did not reach statistical significance. However, as with the other outcomes, the data suggest a dose—response relationship for IGA (FIG. 11C), and the 125 mg Q4W group showed continued improvements in the final weeks of the treatment period (FIG. 2C). With regards to SCORAD-50, more patients in the lebrikizumab 125 mg Q4W group (51.0% [p=0.018]) and 250 mg SD groups (47.2% [p=0.030]) achieved this endpoint at Week 12 compared with placebo (26.4%; FIG. 11D). All lebrikizumab groups showed improvements in BSA affected (Table 3). The greatest reduction in BSA affected at Week 12 was observed in the lebrikizumab 125 mg Q4W group (57.7% reduction), although there were also substantive improvements in the placebo group (47.4%). Placebo-corrected efficacy for BSA was not statistically significant (p=0.38).

Lebrikizumab treatment led to improvements in Pruritus VAS (Table 3 and Table 7). Improvements in Pruritus VAS during the 2-week TCS run-in period were quantitatively larger than improvements in severity measure outcomes. There was a high compliance rate of TCS use amongst all treatment groups with TCS used 86.8% (125 mg SD), 86.7% (250 mg SD), 91.9% (125 mg Q4W) and 88.2% (placebo) of days on average from baseline to Week 12.

Figure 12A:
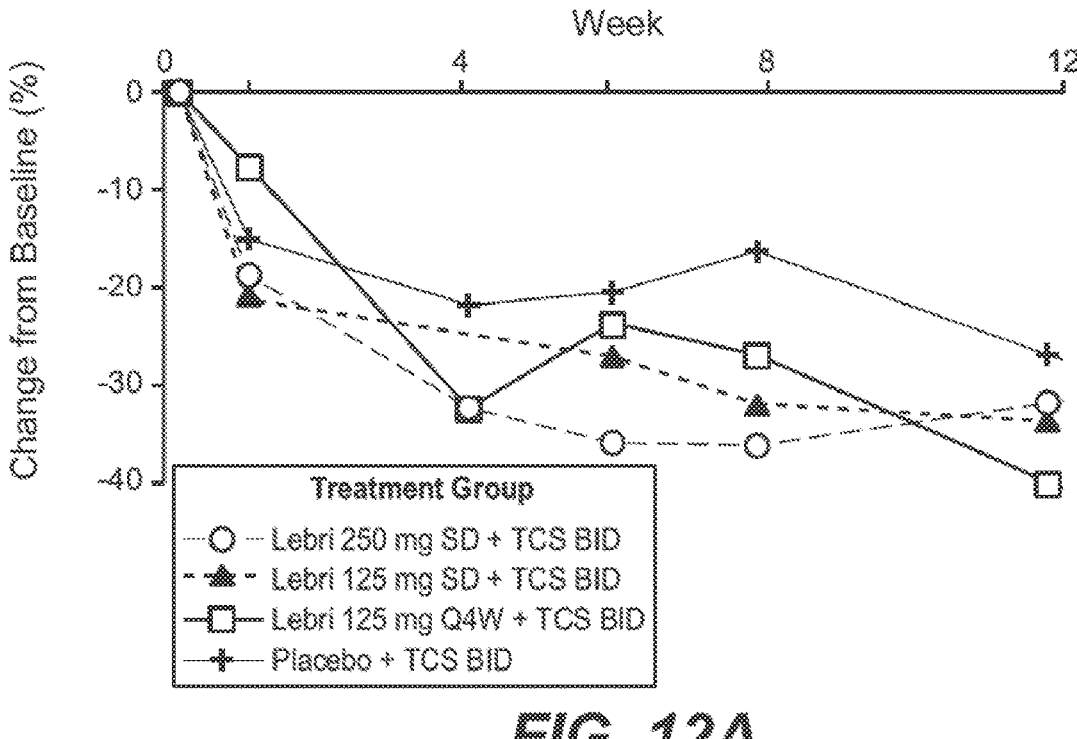
FIGS. 12A-12D show the change from baseline in pruritus VAS (FIG. 12A), ADIQ (FIG. 12B), sleep loss VAS (FIG. 12C), and DLQI (FIG. 12D) over time as described in Example 2. Dashed line with open circles, lebrikizumab 250 mg single dose plus topical corticosteroids (TCS) twice per day (BID); dotted line with closed triangles, lebrikizumab 125 mg single dose plus TCS twice per day; solid line with open squares, lebrikizumab 125 mg once every 4 weeks (Q4W) plus TCS twice per day; solid line with plus signs, placebo plus TCS twice per day. Abbreviations are as follows: VAS=Visual Analog Score; ADIQ=Atopic Dermatitis Impact Questionnaire; DLQI=Dermatology Life Quality Index.
Figure 12B:
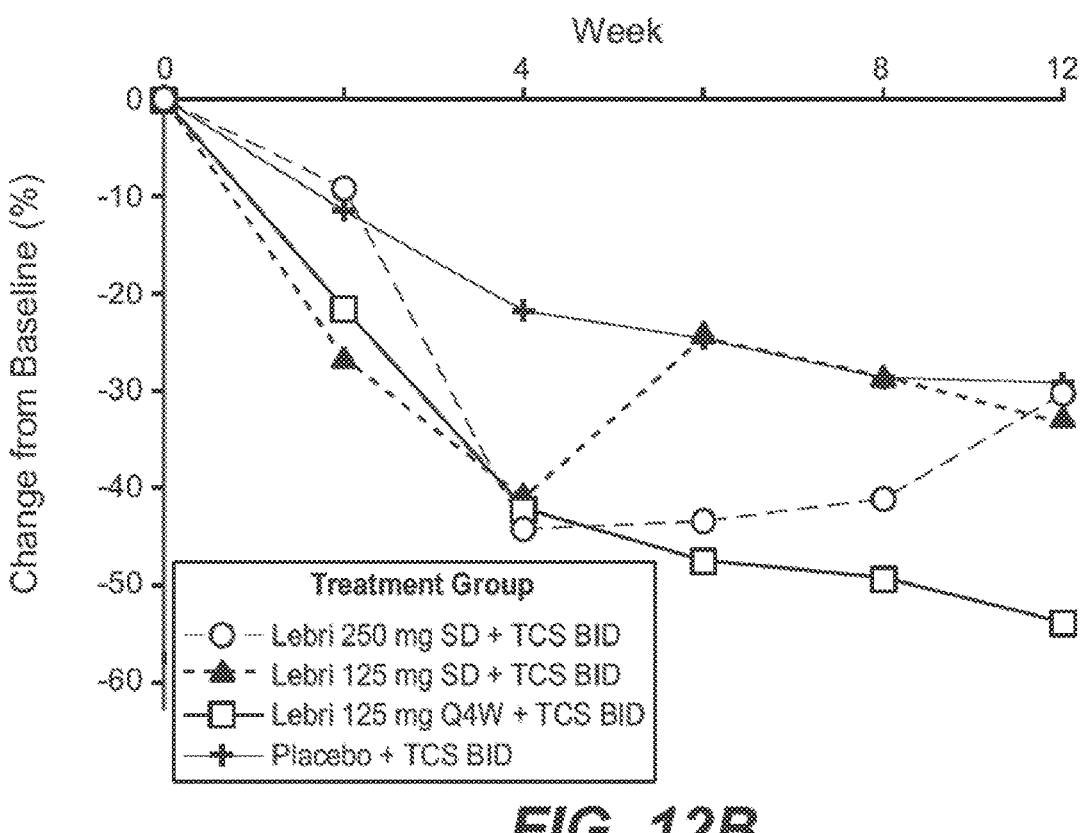
Figures 12C, 12D:
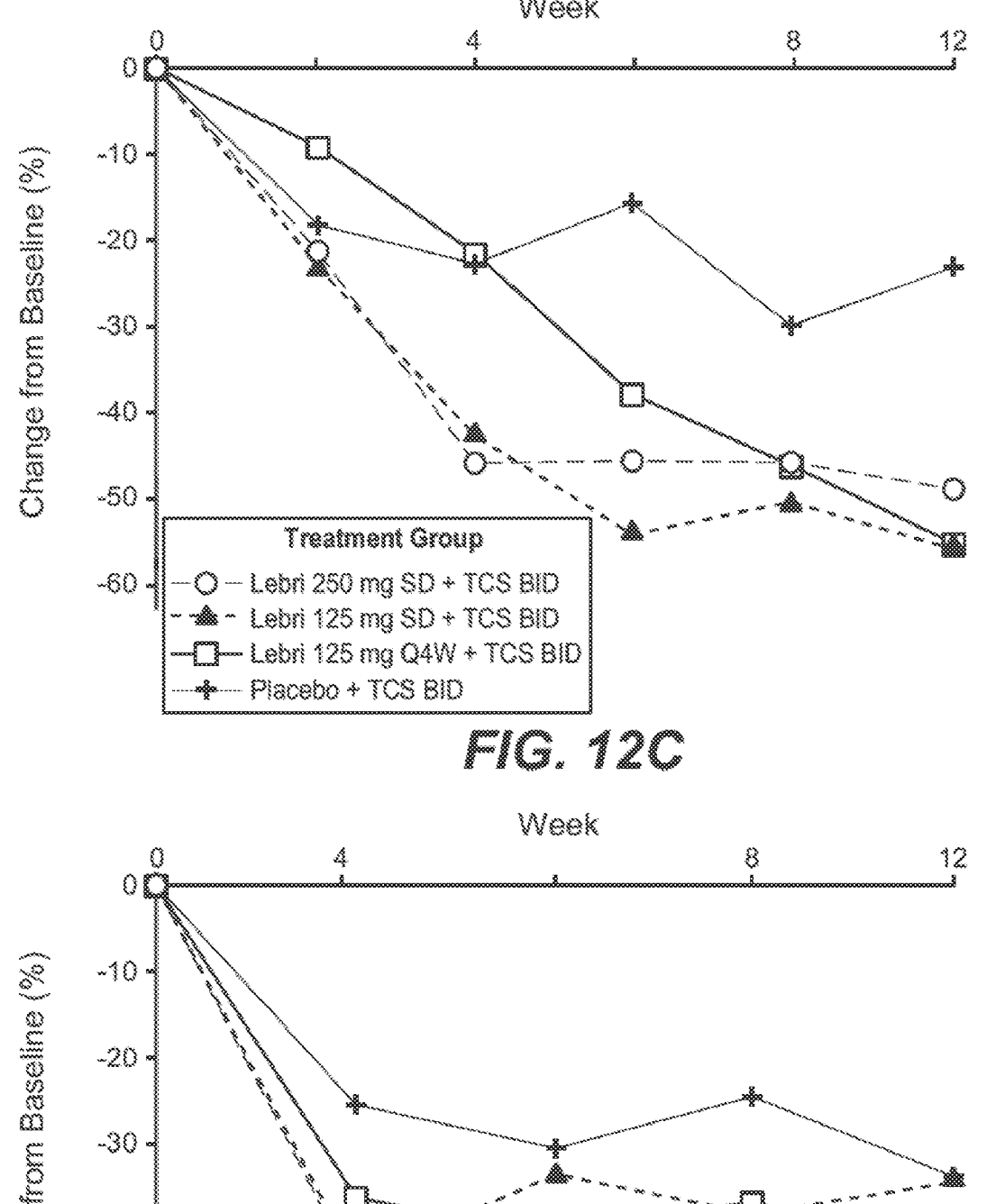

There were also greater improvements in sleep loss VAS, as well as trending improvement in IGA 0/1, pruritus VAS and AD specific health-related quality of life (QoL) measurement, specifically the Atopic Dermatitis Impact Questionnaire (ADIQ), in patients treated with 125 mg lebrikizumab every 4 weeks plus TCS compared with placebo at Week 12 (Table 3, Table 7, FIG. 12A, FIG. 12B, and FIG. 12C). There were also dose-dependent improvements in DLQI scores, with numerically greater reductions from baseline with all lebrikizumab groups compared with placebo (Table 3, Table 7, and FIG. 12D).

Pharmacokinetic parameters were also assessed as follows. Serum samples for analysis of lebrikizumab pharmacokinetics were obtained at Day 1 (pre-dose) and at Weeks 1, 4 (pre-dose), 6, 8 (pre-dose), 12, 16, and 20 for all dosing regimens. Serum lebrikizumab concentrations were summarized by treatment and visit using descriptive statistics for the patients that received one of the lebrikizumab treatment regimens. The reported PK parameters include the Week 1 $C_{max}$, $C_{min}$ at Weeks 4, 8, and 12, and the elimination half-life. The mean PK parameters and respective standard deviations for each of the lebrikizumab dosing regimens are shown in Table 8. The results show that the pharmacokinetics of lebrikizumab in AD patients were consistent with the pharmacokinetics for lebrikizumab reported in the published literature previously for adult asthma (see, e.g., Hanania et al., Thorax 70(8): 748-756 (2015)), showing linear and dose-proportional characteristics with a half-life of 19-22 days.

Adverse event rates were generally similar between treatment groups (66.7% all lebrikizumab groups vs. 66.0% placebo) and most were mild or moderate in severity (Table 9). Specifically, three (2%) patients in the lebrikizumab group (all doses combined) and one (2%) patient in the placebo group experienced an AE (skin infection in the 125 mg SD group, anxiety and myopathy in 125 mg Q4W group and atopic dermatitis in the placebo group) that led to withdrawal from the study. One (1%) patient in the lebrikizumab group experienced an AE (gastrointestinal viral infection) that led to dose interruption. There were no deaths, events of anaphylaxis, malignancy, or protocol-defined parasitic, or targeted intracellular infections of interest. Injection-site reactions occurred infrequently (1.3% all lebrikizumab groups and 1.9% placebo); all events were non-serious, lasted a median of 1-3 days, and did not lead to treatment discontinuation.

Herpes infections occurred infrequently and only among lebrikizumab-treated patients (n=6 [3.8%]; herpes simplex in n=4 [2.6%] and herpes zoster in n=2 [1.3%]); all events were non-serious, and none lead to treatment discontinuation. In addition, there were no events of eczema herpeticum. There were 14 (9%) patients with skin infections among the lebrikizumab-treated groups (all doses combined) and nine (17%) patients in the placebo group. Eosinophil-associated AEs were also reported infrequently and only occurred among five lebrikizumab-treated patients (3.2%; 3 events of "eosinophilia" and 2 events of "eosinophil count increased"); all events were non-serious, mild to moderate in intensity, and did not result in interruption of treatment. The maximum eosinophil count in these five patients ranged from 0.91 to $3.2 \times 10^9/L$ and of these, three were Grade 2 eosinophilia (1501-5000 cell/mm$^3$). Of these five patients, there were no associated clinical symptoms noted with the reported events. Furthermore, the increases observed were in line with what has been seen in previous lebrikizumab studies (Hanania et al., Thorax 2015:70(8): 748-756; Hanania et al., Lancet Respir Med 2016; 4(10): 781-796). We evaluated conjunctivitis given previous imbalances reported in biologic trials in this disease area (Thaci et al., Lancet 2016: 387 (10013): 40-52). A total of 15 (9.6%) patients in the pooled lebrikizumab group and four patients (7.5%) in the placebo group had a conjunctivitis AE; all events were non-serious and none led to treatment discontinuation.

TABLE 3

| Endpoint | Lebri 250 mg Single Dose + TCS BID (n = 53) | Lebri 125 mg Single Dose + TCS BID (n = 52) | Lebri 125 mg Q4W + TCS BID (n = 51) | Placebo + TCS BID (n = 53) |
|---|---|---|---|---|
| | Key efficacy results at Week 12. | | | |
| | % Patients achieving EASI-50 | | | |
| N (%) | 37 (69.8) | 36 (69.2) | 42 (82.4) | 33 (62.3) |
| Placebo-corrected changes | 7.6 | 7.0 | 20.1 | |
| p-value | 0.44 | 0.48 | 0.026 | |
| | % Patients achieving EASI-75 | | | |
| N (%) | 26 (49.1) | 20 (38.5) | 28 (54.9) | 18 (34.0) |
| Placebo-corrected changes | 15.1 | 4.5 | 20.9 | |
| p-value | 0.12 | 0.66 | 0.036 | |
| | % Patients achieving SCORAD-50 | | | |
| N (%) | 25 (47.2) | 18 (34.6) | 26 (51.0) | 14 (26.4) |
| Placebo-corrected change | 20.8 | 8.2 | 24.6 | |
| p-value | 0.030 | 0.38 | 0.012 | |
| | SCORAD score % change from baseline | | | |
| N | 53 | 52 | 51 | 53 |
| Adjusted mean (SE) | −42.6 (4.07) | −38.7 (4.14) | −53.5 (4.22) | −35.4 (4.16) |
| Δ (95% CI) | −7.2 (−18.7, 4.3) | −3.3 (−14.9, 8.3) | −18.0 (−29.7, −6.4) | |
| p-value | 0.22 | 0.57 | 0.0026 | |
| | % Patients achieving SCORAD-75 | | | |
| N (%) | 6 (11.3) | 7 (13.5) | 11 (21.6) | 7 (13.2) |
| | % Patients achieving IGA 0/1 | | | |
| N (%) | 15 (28.3) | 11 (21.2) | 17 (33.3) | 10 (18.9) |
| Placebo-corrected change | 9.4 | 2.3 | 14.5 | |
| p-value | 0.26 | 0.77 | 0.098 | |
| | Total % BSA affected, % change from baseline | | | |
| N | 53 | 52 | 51 | 53 |
| Adjusted mean (SE) | −38.6 (8.07) | −45.2 (8.21) | −57.7 (8.35) | −47.4 (8.24) |
| Δ (95% CI) | 8.8 (−13.9, 31.6) | 2.2 (−20.7, 25.1) | −10.3 (−33.4, 12.9) | |
| p-value | 0.45 | 0.85 | 0.38 | |
| | % change from baseline in Prurit us VAS (from SCORAD) | | | |
| Mean | −32.82 | −34.92 | −40.71 | −27.54 |
| Placebo-corrected change | −5.28 | −7.38 | −13.7 | |
| p-value | 0.54 | 0.40 | 0.13 | |

TABLE 3-continued

| | Key efficacy results at Week 12. | | | |
| --- | --- | --- | --- | --- |
| Endpoint | Lebri 250 mg Single Dose + TCS BID (n = 53) | Lebri 125 mg Single Dose + TCS BID (n = 52) | Lebri 125 mg Q4W + TCS BID (n = 51) | Placebo + TCS BID (n = 53) |
| | % change from baseline in Sleep Loss VAS (from SCORAD) | | | |
| Mean (SD) | −47.2 | −53.1 | −53.6 | −22.6 |
| Placebo-corrected change | −24.6 | −30.6 | −31.0 | |
| p-value | 0.08 | 0.03 | 0.02 | |
| | % change from baseline in AD Specific health-related QoL - ADIQ | | | |
| Mean | −30.8 | −33.9 | −54.3 | −29.0 |
| Placebo-corrected change | −1.8 | −4.9 | −25.3 | |
| p-value | 0.89 | 0.71 | 0.052 | |
| | DLQI, % change from baseline | | | |
| N | 53 | 52 | 51 | 53 |
| Adjusted mean (SE) | −40.67 (6.69) | −34.33 (6.93) | −43.12 (7.02) | −33.57 (6.93) |
| Δ (95% CI) | −7.09 (−26.04, 11.85) | −0.76 (−20.04, 18.52) | −9.55 (−28.91, 9.82) | |
| p-value | 0.46 | 0.94 | 0.33 | |

ADIQ = Atopic Dermatitis Impact Questionnaire; BSA = body surface area; CI = confidence interval; DLQI = Dermatology Life Quality Index; EASI = Eczema Area Severity Index; IGA = Investigator Global Assessment; SCORAD = SCORing Atopic Dermatitis; SE = standard error; VAS = Visual Analog Scale.

TABLE 7

| | Percent change in EASI, SCORAD, IGA, Pruritus VAS, and percent BSA affected from screening to baseline (run-in). | | | | |
| --- | --- | --- | --- | --- | --- |
| | Lebrikizumab 125 mg SD (n = 52) | Lebrikizumab 250 mg SD (n = 53) | Lebrikizumab 125 mg Q4W (n = 51) | Placebo (n = 53) | All patients (n = 209) |
| Mean % Change in EASI (SD) | −14.3 (27.6) | −10.2 (29.2) | −9.1 (22.7) | −6.4 (32.2) | −10.0 (28.1) |
| Mean Absolute Change in IGA (SD) | −0.21 (0.50) | −0.17 (0.51) | −0.14 (0.40) | −0.09 (0.45) | −0.15 (0.47) |
| Mean % Change in SCORAD (SD) | −12.2 (20.0) | −9.9 (14.7) | −7.7 (15.0) | −5.0 (20.3) | −8.7 (17.8) |
| Mean % Change in % BSA Affected (SD) | −17.1 (26.7) | −4.3 (26.9) | −9.3 (27.0) | −6.2 (23.2) | −9.2 (26.3) |
| Mean % Change in Pruritus VAS (SD) | −23.8 (29.6) | −15.5 (28.6) | −15.2 (39.4) | −12.8 (29.8) | −16.8 (32.1) |
| Mean % Change in Sleep VAS (SD) | −29.0 (43.6) | −8.1 (81.8) | −12.9 (40.1) | −5.4 (57.2) | −13.9 (58.2) |

BSA = body surface area; EASI = Eczema Area Severity Index; IGA = Investigator Global Assessment; Q4W = every 4 weeks; SD = single dose SCORAD = SCORing Atopic Dermatitis; SD = single dose; SE = standard error; VAS = Visual Analog Scale.

TABLE 8

| | Mean Lebrikizumab Pharmacokinetic Parameters Following Single or Multiple Dose Subcutaneous Administration. | | |
| --- | --- | --- | --- |
| | Lebrikizumab 125 mg SD | Lebrikizumab 250 mg SD | Lebrikizumab 125 mg Q4W |
| Mean $C_{max, wk1}$ µg/mL (SD) | 17.0 (5.22) | 35.6 (10.8) | 16.1 (5.19) |
| Mean $C_{min, wk4}$ µg/mL (SD) | 10.2 (3.00) | 21.4 (6.87) | 9.15 (2.99) |
| Mean $C_{min, wk8}$ µg/mL (SD) | 4.59 (2.12) | 9.53 (3.53) | 13.6 (5.34) |

TABLE 8-continued

| | Mean Lebrikizumab Pharmacokinetic Parameters Following Single or Multiple Dose Subcutaneous Administration. | | |
| --- | --- | --- | --- |
| | Lebrikizumab 125 mg SD | Lebrikizumab 250 mg SD | Lebrikizumab 125 mg Q4W |
| Mean $C_{min, wk12}$ µg/mL (SD) | 2.28 (1.72) | 3.77 (2.01) | 14.4 (5.69) |
| t½, day | 18.5 (5.06) | 22.2 (6.18) | 20.9 (4.17) |

$C_{max, wk1}$ = maximum lebrikizumab concentration at Week 1, $C_{min, wk4}$ = observed minimum concentration at Week 4, $C_{min, wk8}$ = observed minimum concentration at Week 8, $C_{min, wk12}$ = observed minimum concentration at Week 12, t½ = elimination half-life

TABLE 9

| | Lebrikizumab 125 mg SD (n = 54) | Lebrikizumab 250 mg SD (n = 52) | Lebrikizumab 125 mg Q4W (n = 50) | All lebrikizumab (n = 156) | Placebo (n = 53) |
|---|---|---|---|---|---|
| Overview of key safety information, Weeks 0 to 20. | | | | | |
| Patients with at least one AE, n (%) | 38 (70) | 39 (75) | 27 (54) | 104 (67) | 35 (66) |
| AE leading to withdrawal from study drug | 1 (2) | 0 | 2 (4) | 3 (2) | 1 (2) |
| AE leading to dose modification/interruption | 0 | 1 (2) | 0 | 1 (1) | 0 |
| Patients with at least one serious AE, n (%) | 3 (6) | 0 | 2 (4) | 5 (3) | 2 (4) |
| SAE leading to withdrawal from study drug Myopathy | 0 | 0 | 1 (2) | 1 (1) | 0 |
| Adverse events of interest, n (%) | | | | | |
| Adjudicated anaphylaxis per Sampson's criteria* | 0 | 0 | 0 | 0 | 0 |
| Infections | 24 (44) | 20 (39) | 12 (24) | 56 (36) | 24 (45) |
| Patients with skin infection | 6 (11) | 5 (10) | 3 (6) | 14 (9) | 9 (17) |
| Injection site reactions | 0 | 0 | 2 (4) | 2 (1) | 1 (2) |
| Malignancies | 0 | 0 | 0 | 0 | 0 |
| Herpes infections, n (%) | | | | | |
| Total number of patients with at least one infection | 2 (3.9) | 3 (5.7) | 2 (3.9) | 6 (3.8) | 0 |
| Total number of infections related to study drug† | 0 | 0 | 0 | 0 | 0 |
| Herpes Simplex | 1 (2.0) | 2 (3.8) | 1 (2.0) | 4 (2.6) | 0 |
| Herpes Zoster | 1 (2.0) | 1 (1.9) | 1 (2.0) | 2 (1.3) | 0 |
| Conjunctival infections, irritations and inflammations, n (%) | | | | | |
| Total number of patients with at least one AE | 4 (7.4) | 3 (5.8) | 2 (4.0) | 9 (5.8) | 0 |
| Total number of events | 4 (7.4) | 3 | 3 | 10 | 0 |
| Conjunctivitis allergic | 4 (7.4) | (3.8) | 2 (4.0) | 8 (5.1) | 0 |
| Conjunctival hyperaemia | 0 | 1 (1.9) | 0 | 1 (0.6) | 0 |

AE = adverse event; Q4W = every 4 weeks; SAE = serious adverse event; SD = single dose.
*Blinded data was reviewed to adjudicate cases as anaphylaxis per Sampson's criteria.
†Infections related to study drug were investigator-assessed.

Figure 2B:
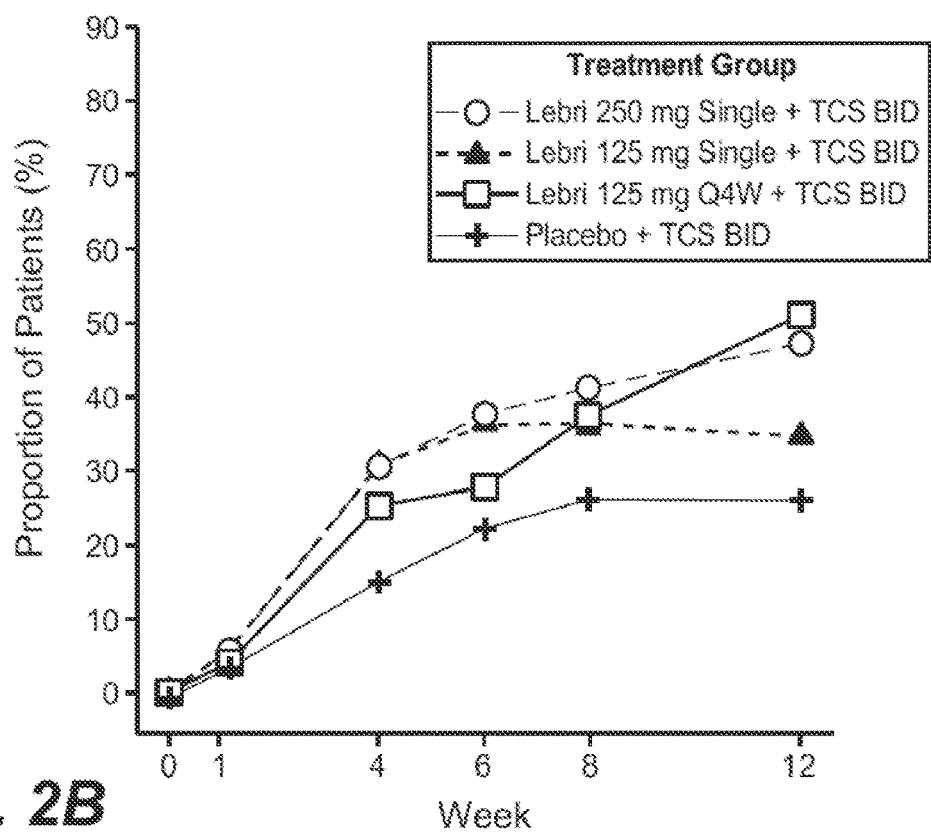
FIG. 2B shows the proportion of patients achieving SCO-RAD-50 over 12 weeks as described in Example 2. Dashed line with open circles, lebrikizumab 250 mg single dose plus topical corticosteroids (TCS) twice per day (BID); dotted line with closed triangles, lebrikizumab 125 mg single dose plus TCS twice per day; solid line with open squares, lebrikizumab 125 mg once every 4 weeks (Q4W) plus TCS twice per day; solid line with plus signs, placebo plus TCS twice per day.
Figure 2C:
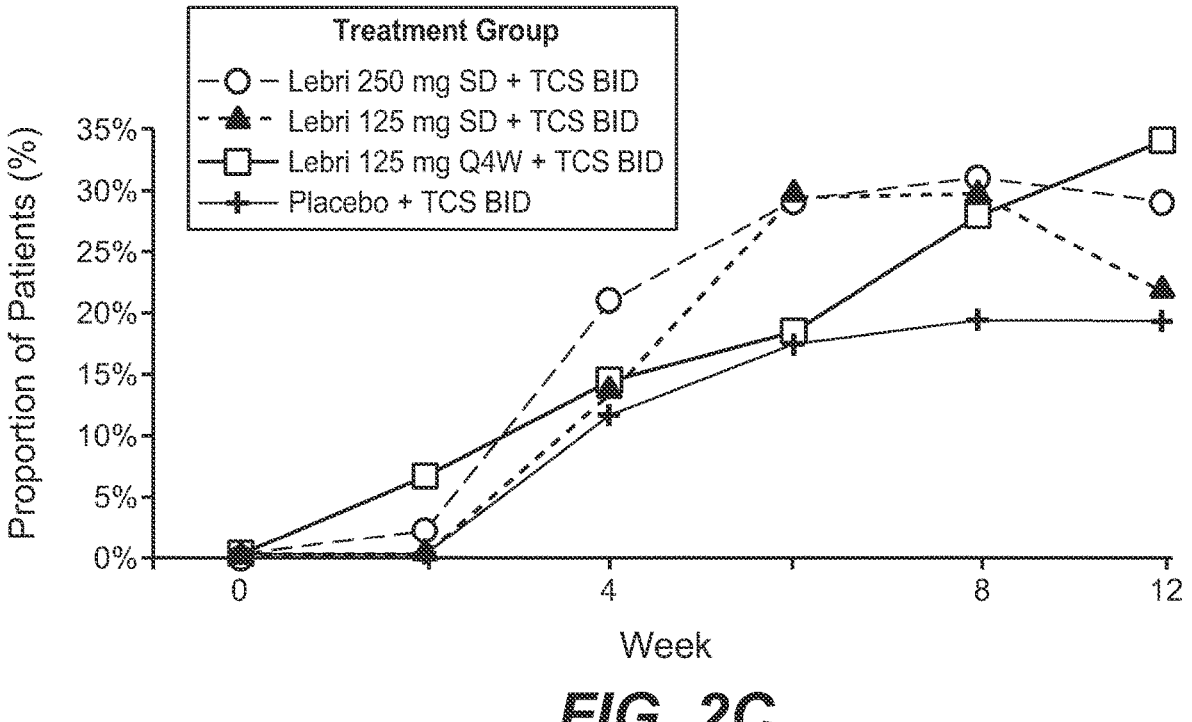
FIG. 2C shows the proportion of patients achieving IGA 0/1 over 12 weeks as described in Example 2. Dashed line with open circles, lebrikizumab 250 mg single dose plus topical corticosteroids (TCS) twice per day (BID); dotted line with closed triangles, lebrikizumab 125 mg single dose plus TCS twice per day; solid line with open squares, lebrikizumab 125 mg once every 4 weeks (Q4W) plus TCS twice per day; solid line with plus signs, placebo plus TCS twice per day.
Figure 3A:
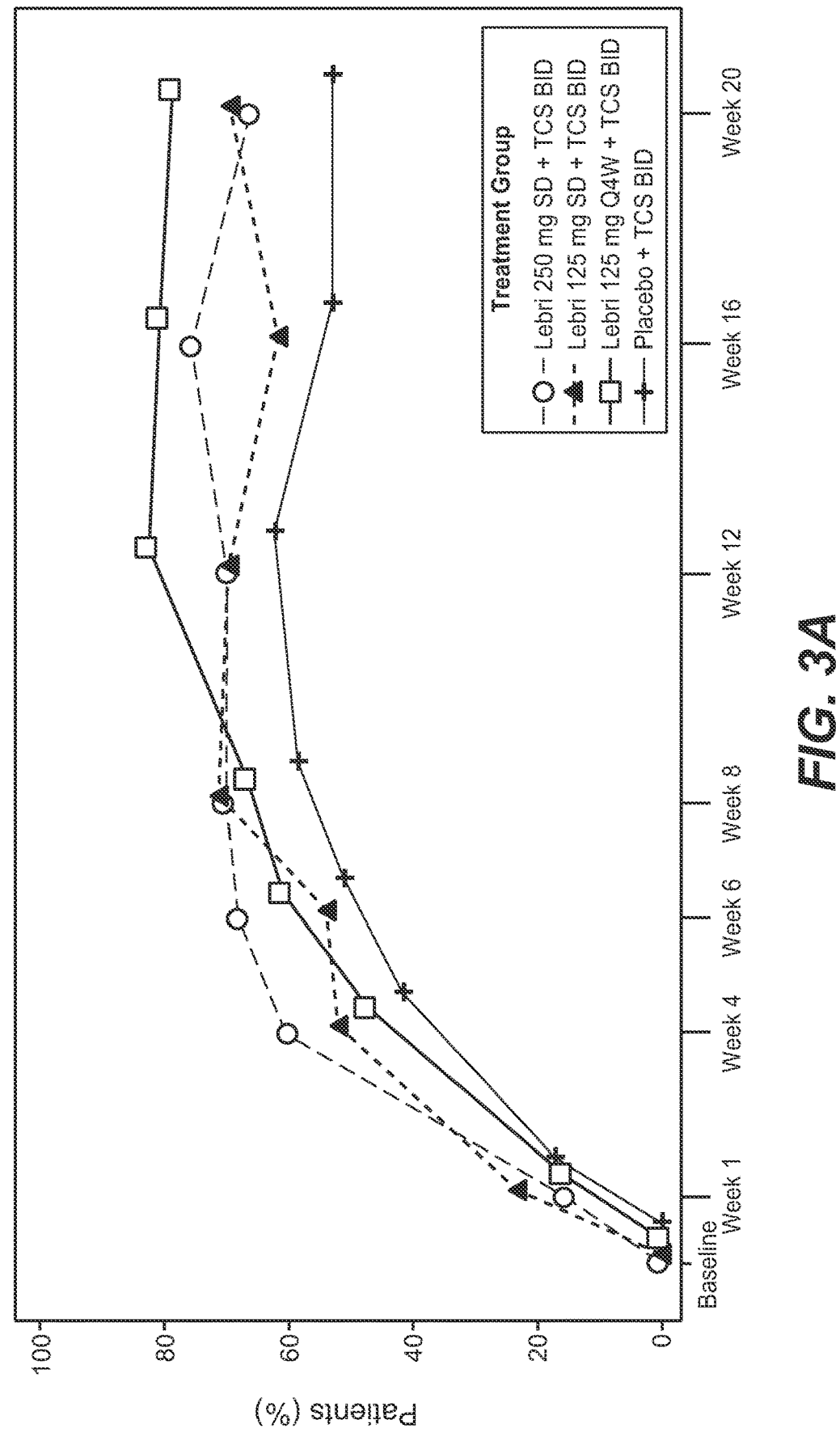
FIGS. 3A-3C show the proportion of patients achieving EASI-50 (FIG. 3A), EASI-75 (FIG. 3B) and EASI-90 (FIG. 3C) over 20 weeks in the modified intention-to-treat population as described in Example 2. Dashed line with open circles, lebrikizumab 250 mg single dose plus topical corticosteroids (TCS) twice per day (BID); dotted line with closed triangles, lebrikizumab 125 mg single dose plus TCS twice per day; solid line with open squares, lebrikizumab 125 mg once every 4 weeks (Q4W) plus TCS twice per day; solid line with plus signs, placebo plus TCS twice per day.
Figure 3B:
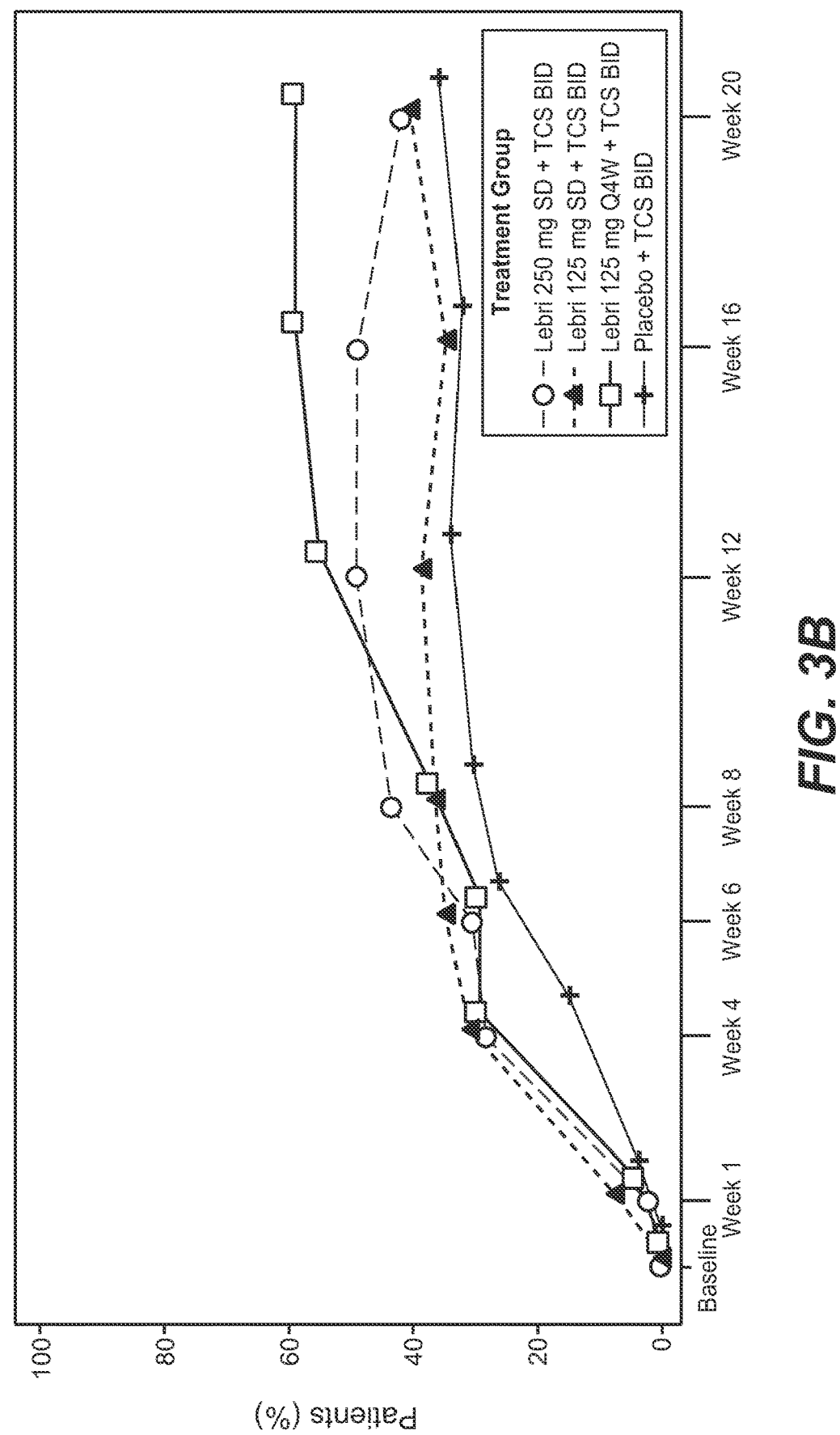
Figure 3C:
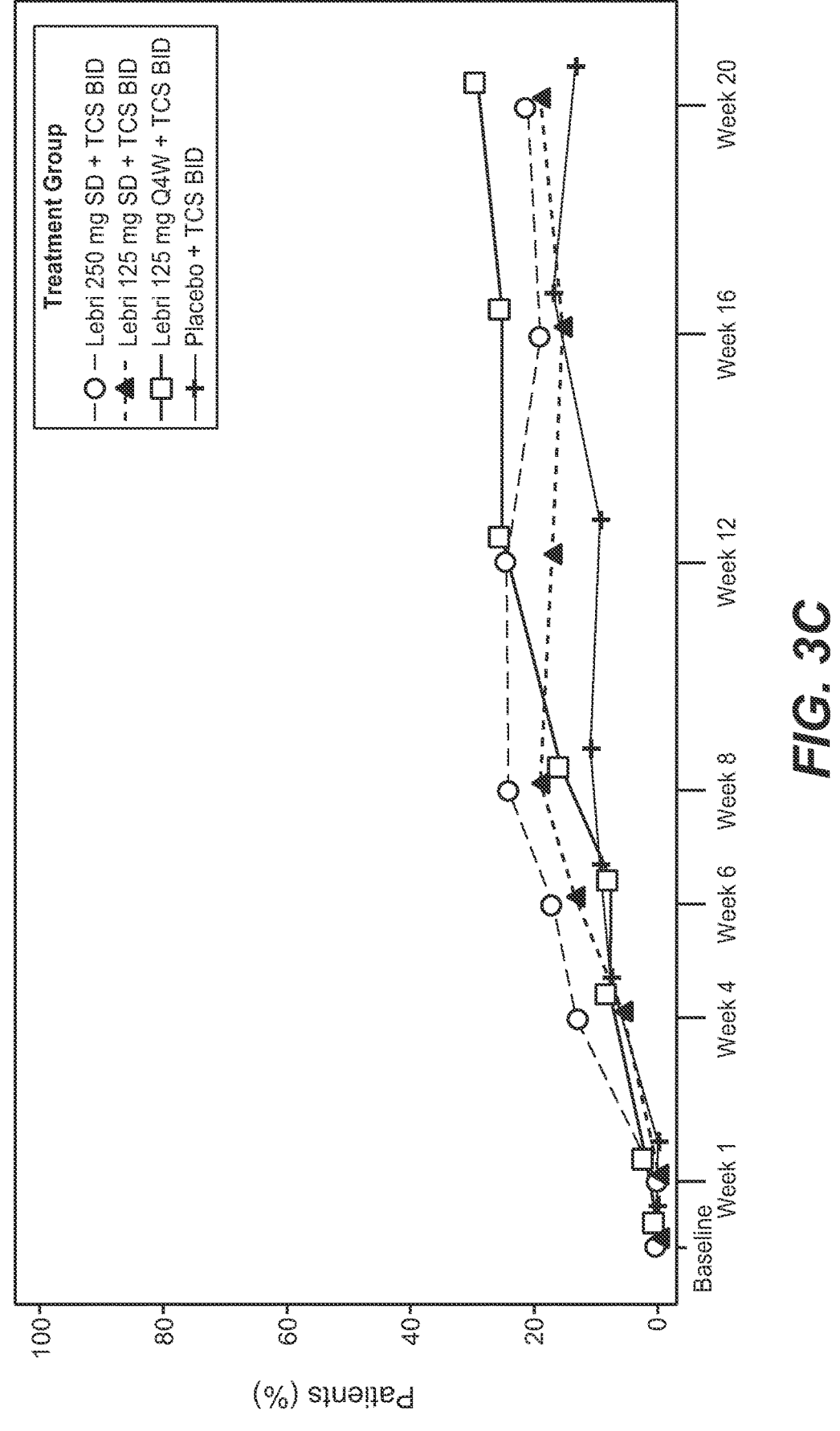

We also observed an apparent dose-response relationship for the data shown in FIG. 2A. The 250 mg single dose was numerically better at early time points compared to the 125 mg single dose. Furthermore, the data shown in FIG. 2A suggests that the 125 mg dose once every four weeks did not appear to have reached an efficacy plateau at Week 12. These data suggest the potential benefit of either higher dosing (e.g., 250 mg Q4W) or a loading dose.

Figure 4:
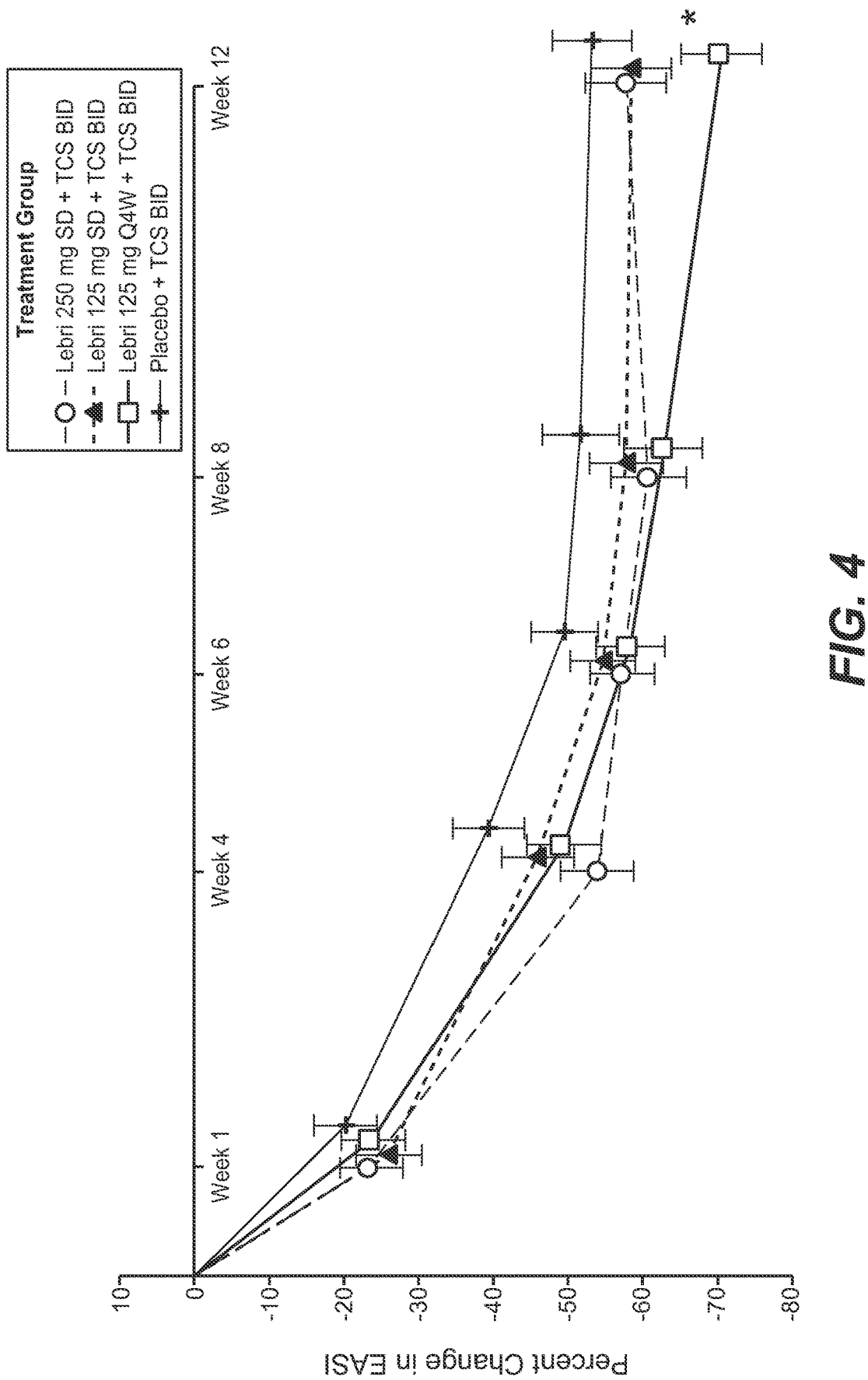
FIG. 4 shows the percent change from baseline in EASI over 12 weeks in the modified intention-to-treat population as described in Example 2. Dashed line with open circles, lebrikizumab 250 mg single dose plus topical corticosteroids (TCS) twice per day (BID); dotted line with closed triangles, lebrikizumab 125 mg single dose plus TCS twice per day; solid line with open squares, lebrikizumab 125 mg once every 4 weeks (Q4W) plus TCS twice per day; solid line with plus signs, placebo plus TCS twice per day. Data points shown are adjusted mean with standard error bars. The asterisk (*) indicates that the placebo corrected change is 17.4%, P=0.025.

In addition, at Week 20, in the modified intention-to-treat population, a greater proportion of patients treated with 125 mg lebrikizumab every 4 weeks plus TCS achieved EASI-50 (FIG. 3A), EASI-75 (FIG. 3B), and EASI-90 (FIG. 3C) compared with placebo. See also Table 9. A greater percent decrease from baseline in EASI over 12 weeks in the lebrikizumab-treated patients compared with placebo was also observed (FIG. 4). Notably, the patients who received 125 mg lebrikizumab once every four weeks for 12 weeks showed a 70.5% change (decrease) in EASI compared to a 53.1% change (decrease) in the placebo arm. That 17.4% difference between lebrikizumab treatment and placebo was statistically significant, P=0.025.

TABLE 9

| | Lebrikizumab 125 mg SD | Lebrikizumab 250 mg SD | Lebrikizumab 125 mg Q4W | Placebo |
|---|---|---|---|---|
| Summary of key efficacy outcomes at Week 20. | | | | |
| Patients maintaining EASI-50 response at Weeks 12 and 20 | | | | |
| N (%) | 29 (80.6) | 29 (78.4) | 38 (90.5) | 24 (72.7) |
| Placebo-corrected differences (SE) | 7.83 | 5.65 | 17.75 | |
| p-value | 0.39 | 0.58 | 0.047 | |
| Patients maintaining EASI-75 response at Weeks 12 and 20 | | | | |
| N (%) | 9 (45.0) | 16 (61.5) | 21 (75.0) | 12 (66.7) |
| Placebo-corrected differences (SE) | −21.70 | −5.13 | 8.33 | |
| p-value | 0.202 | 0.81 | 0.54 | |

TABLE 9-continued

Summary of key efficacy outcomes at Week 20.

| | Lebrikizumab 125 mg SD | Lebrikizumab 250 mg SD | Lebrikizumab 125 mg Q4W | Placebo |
|---|---|---|---|---|
| Patients maintaining IGA 0/1 response at Weeks 12 and 20 | | | | |
| N (%) | 6 (54.5) | 9 (60.0) | 12 (70.6) | 1.6 (60) |
| Placebo-corrected differences (SE) | −5.45 | 0 | 10.59 | |
| p-value | 0.97 | 0.94 | 0.58 | |
| Patients maintaining SCORAD-50 response at Weeks 12 and 20 | | | | |
| N (%) | 11 (61.1) | 16 (64.0) | 13 (50.0) | 11 (78.6) |
| Placebo-corrected differences (SE) | −17.50 | −14.60 | −28.60 | |
| p-value | 0.34 | 0.49 | 0.13 | |
| Change from baseline in EASI | | | | |
| Mean % change (SE) | −62.1 (5.4) | −55.9 (5.3) | −71.1 (5.5) | −54.1 (5.5) |
| Placebo-corrected differences (SE) | −8.08 (7.72) | −1.88 (7.62) | −17.08 (7.78) | |
| p-value | 0.30 | 0.81 | 0.030 | |
| Change from baseline in the % BSA affected | | | | |
| Mean % change (SE) | 53.7 (6.1) | −46.4 (6.0) | 63.8 (6.2) | 52 (6.2) |
| Placebo-corrected differences (SE) | | 5.56 (8.6) | | |
| p-value | 0.85 | 6.52 | 0.18 | |
| Change from baseline Pruritus VAS | | | | |
| Mean % change (SE) | −27.59 | −30.25 | −35.23 | −21.46 |
| Placebo-corrected differences (SE) | −6.13 | −8.79 | −13.76 | |
| p-value | 0.57 | 0.41 | 0.21 | |

BSA = body surface area; EASI = Eczema Area Severity Index; IGA = Investigator Global Assessment; SCORAD = SCORing Atopic Dermatitis; SD = single dose; SE = standard error; VAS = Visual Analog Scale.

We also measured patients' symptoms and health-related quality of life by SCORAD Pruritus Visual Analog Scale (VAS), Sleep Loss VAS and the ADIQ. Improvements from Baseline were demonstrated in the Pruritus VAS, Sleep Loss VAS, and ADIQ (shown in Table 3). Post hoc analysis also examined change from screening. Patients treated with 125 mg lebrikizumab administered once every four weeks showed a Pruritus VAS 55.2% (p=0.03 vs placebo) reduction from screening at Week 12 while placebo resulted in reductions of 39.3% from screening. There were also improvements in Sleep Loss VAS from screening to Week 12, with a 61.5% (p=0.04 vs placebo) reduction with lebrikizumab treatment and placebo reduction 39.3%. There was a 64.7% (p=0.02 vs placebo) reduction in ADIQ from screening with lebrikizumab treatment and placebo reduction of 41.8%. Differences in these endpoints, relative to placebo, for groups in which lebrikizumab was only given as a single dose (125 mg and 250 mg) were in most cases not statistically significant.

In summary, these results demonstrate that targeting IL-13 in moderate-to-severe AD provides clinically meaningful placebo-corrected improvements in a number of severity outcomes, generally in a dose-dependent manner. Monthly dosing significantly improved the proportion of patients achieving EASI-50, EASI-75, and SCORAD-50 with trends for improvement in patients achieving IGA 0/1 and improvements in pruritus VAS. These improvements were seen on top of intensive TCS application associated with substantial responses in the placebo group. Adverse event rates were generally similar between treatment groups and most were mild or moderate in severity.

In addition, the results show that lebrikizumab provides treatment benefit on top of rigorous application of TCS in patients with moderate-to-severe AD who had an inadequate response to standard-of-care TCS treatment and baseline characteristics indicating a patient population towards the more severe end of the spectrum. The study met its primary endpoint—the percentage of patients with EASI-50 at Week 12—with a statistically significant number of patients in the lebrikizumab 125 mg Q4W group achieving this level of reduction in the baseline EASI score. Moreover, the upward sloping response curves over the final weeks of the treatment period suggest that the response plateau might not have been reached by Week 12 for the lebrikizumab 125 mg Q4W group and longer treatment duration may lead to improved efficacy. There also appeared to be a dose—response relationship, with the lebrikizumab 125 mg Q4W dose showing numerically highest response rates across most endpoints, in particular EASI, with lebrikizumab 125 mg SD showing the least benefit at Week 12.

Notably, the lebrikizumab 250 mg SD group showed numerically higher responses at earlier time points for several outcomes, suggesting the potential benefit of either higher dosing or a loading dose. In all main efficacy endpoints, there was a continuous improvement observed over the course of the 12-week treatment period. Differences in many of the secondary efficacy endpoints at Week 12 were statistically significant at the unadjusted 5% significance level for patients in the lebrikizumab 125 mg Q4W group compared with patients in the placebo group. These included the percentage of patients with EASI-75, percentage of patients with SCORAD-50, percent change from baseline in EASI score, and percent change from baseline in SCORAD. Improvements in IGA and Pruritus VAS were numerically higher than placebo. Pruritus is considered a key contributor to the reduced QoL of patients with moderate-to-severe AD, and there were numerically greater improvements in QoL (as measured by DLQI and ADIQ) and sleep with the lebrikizumab 125 mg Q4W dosing, likely due to improvements in pruritus. In general, the effects of lebrikizumab were also maintained during the 8-week follow-up period in several outcomes, including EASI, IGA (0/1) and SCORAD responses maintained until Week 20.

Given the dose-response relationships observed across multiple endpoints, and the trends towards improved efficacy with increasing dose and duration, it is reasonable to hypothesize that further increases in the dose (either in the form of a loading dose or a higher dose such as 250 mg Q4W) and/or treatment duration may lead to improved efficacy. Furthermore, the observed differences in the lebrikizumab dose-response relationship between $FEV_1$ in asthma patients (Hanania et al., Thorax 2015; 70(8):748-756) and EASI/IGA endpoints in AD patients suggest that AD may in fact require higher doses of lebrikizumab to achieve a response plateau. This would be consistent with a higher IL-13 burden among atopic dermatitis patients relative to asthma patients.

The protocol for this study required patient compliance with twice-daily TCS during the 2-week run-in period to be eligible for randomization. Moreover, patients were only eligible for randomization if they manifested sufficient AD severity after this run-in period. Although the patients included in this study were being inadequately controlled by TCS, inclusion of this TCS run-in period led to substantial improvement of the disease. This improvement was demonstrated by the suppressed baseline AD severity scores, especially itch measures, likely causing demonstration of additional improvement beyond baseline to be more difficult.

During the treatment period, the protocol mandated continued application of twice-daily TCS and patients were provided daily reminders by electronic diaries; patients in this study applied TCS with a high compliance rate of 88% in all treatment groups. While daily TCS use is typically recommended for acute lesions rather than continuously and indefinitely, this proof-of-concept Phase 2 study sought to understand the potential efficacy of lebrikizumab in addition to intensely rigorous TCS application (Eichenfield et al., J Am Acad Dermatol. 2014; 71(1):116-132) and not to assess TCS sparing. Consideration was given to less frequent application of TCS because this TCS regimen may not be reflective of long-term treatment or of clinical practice. However, this regimen is consistent with TCS labeling, and there were regulatory concerns about off-label usage at a lower frequency than mandated by product labeling. At the same time, there were concerns that an alternate design that did not allow for background TCS, such as lebrikizumab monotherapy, would lead to substantial patient dropout and/or imputed patient failure within the control arm. Indeed, studies of biologic therapies in a monotherapy setting have led to drop-out/imputed patient failure rates on the order of approximately 50% within the control arm (Simpson et al., N Engl J Med. 2016; 375(24):2335-2348) in contrast to the dropout rate of 13% for the placebo arm in this study. The rigorous TCS application during the 12-week treatment period likely explains the substantial response observed in the placebo arm. Prolonged and frequent TCS use has been shown to result in progressive improvements in AD, but most guidelines suggest limiting daily use to avoid AEs. See, e.g., Brunner et al., J Allergy Clin Immunol. 2016; 138(1):169-178; Schneider et al., J Allergy Clin Immunol. 2013; 131(2):295-9. e1-27; and Hanifin et al., J Am Acad Dermatol. 2004; 50(3):391-404. Furthermore, this substantial response in the placebo arm could be why a larger treatment difference between the placebo and the lebrikizumab treatment arms was not observed. Despite the relatively high efficacy of prolonged and frequent TCS use, there were still significant improvements, particularly in AD signs (EAST) and global scores (SCORAD), with adding lebrikizumab treatment.

Dupilumab, an anti-IL-4Rα monoclonal antibody, demonstrated efficacy in patients with moderate-to-severe AD and has been recently approved in AD. IL-4Rα is thought to be an important receptor subunit for both IL-4 and IL-13 signaling. Studies of dupilumab in AD patients provide insight into the potential of IL-13 blockade to treat AD, with the caveat that the relative importance of IL-4 compared with IL-13 in AD has not been established. Both IL-13 and IL-4 share overlapping biology and effector functions; for example, both play a role in T-helper 2-cell development, IgE production, eosinophil recruitment, epithelial barrier integrity disruption via down-regulation of antimicrobial peptides, fibrosis, and decreased filaggrin expression. See, e.g., Paternoster et al., Nat Genet. 2011; 44(2):187-192; Kagami et al., Clin Exp Immunol. 2005; 141(3):459-466. Because of such high overlap in biology, blockade of IL-13 alone could potentially provide comparable improvements in AD to blockade of IL-13 and IL-4 in combination, with a more specific targeted action. In addition, targeting a soluble cytokine, such as IL-13 may offer the advantage of alinear PK profile with resulting improvements in dosing frequency. This in part explains the ability to dose lebrikizumab Q4W and may allow for less frequent dosing during maintenance. In contract, receptor targeting is associated with target-mediated drug clearance that may lead to rapid declines in concentration after drug discontinuation or interruption, as is the case with dupilumab, which is dosed Q2W (Kovalenko et al., CPT Pharmacometrics Syst Pharmacol. (2016) November; 5(11):617-624).

The results of this study suggest that IL-13-mediated signaling pathways play an important role in the pathogenesis of AD, and the blockade of this cytokine could lead to significant clinical benefit. Patients with moderate-to-severe AD showed improvements with lebrikizumab treatment, even with single doses and intensive TCS use. Future studies of longer duration, with more frequent or higher dosing and in a larger population, on different background regimens (or absence of) will help clarify the role of targeting IL-13 alone in AD.

Example 3

Alternative Dosing Regimens

To evaluate whether alternative lebrikizumab dosing regimens could be developed and could be predicted to demonstrate efficacy, we developed a novel, mechanism-based, longitudinal PK-PD model as described below. The model was used to simulate the predicted efficacy, e.g., EASI-75 score, of various alternative dosing regimens, for example, including but not limited to, various loading doses followed subsequently by various maintenance doses, e.g., flat doses of lebrikizumab administered at regular time intervals, or various lower flat doses or higher flat doses, or increased treatment intervals with lebrikizumab.

The model development began with raw pharmacokinetic and efficacy data that had been collected during the conduct of the Phase II Clinical Study I described above. The lebrikizumab pharmacokinetic data in atopic dermatitis patients was consistent with predictions made from the lebrikizumab population PK model, which had been developed on the basis of drug concentrations obtained from asthma patients and healthy volunteers (data not shown). This allowed for the use of the lebrikizumab population PK model to facilitate the development of the atopic dermatitis PK-PD model as described below.

Figure 5:
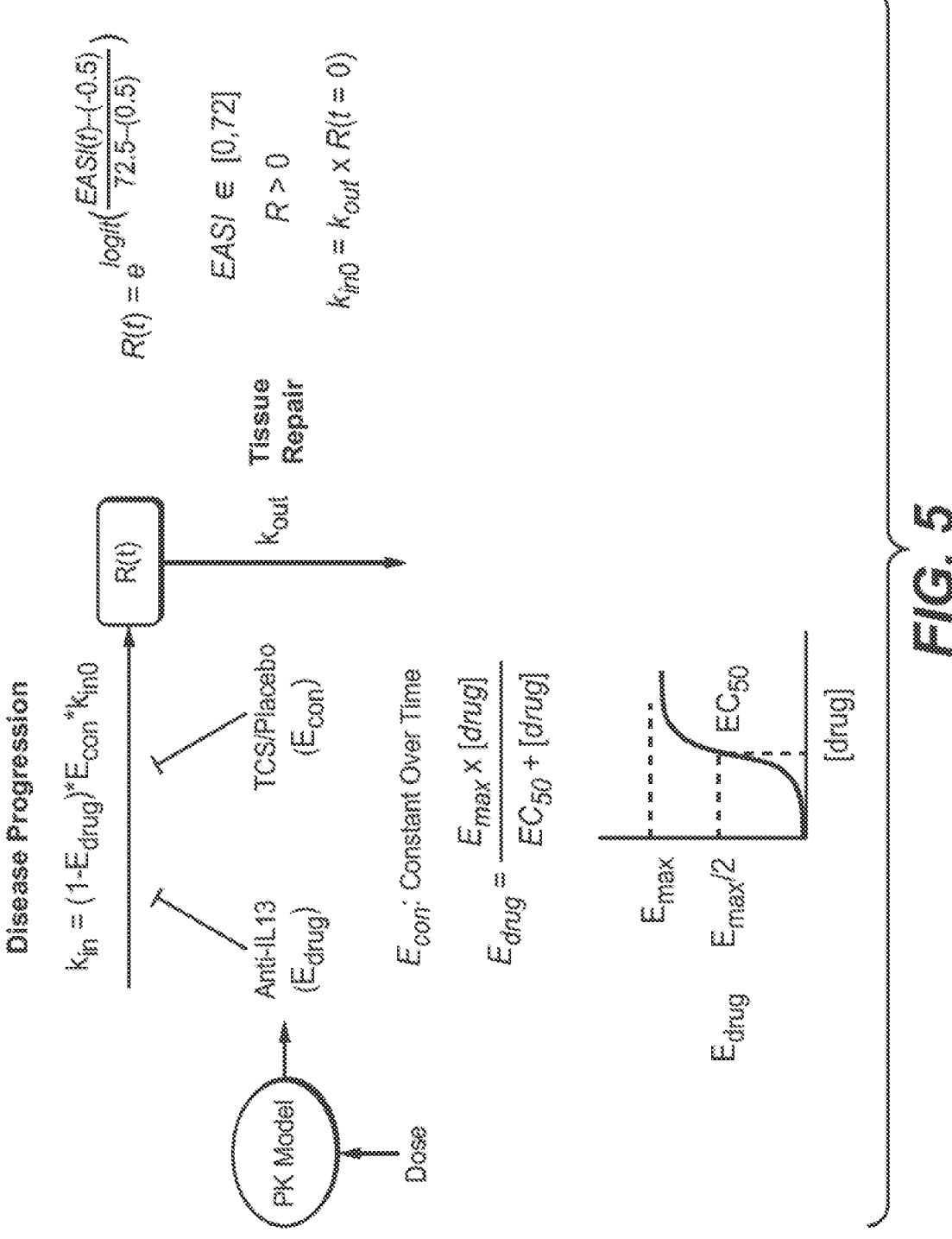
FIG. 5 shows the atopic dermatitis longitudinal PK-PD model of lebrikizumab as described in Example 3.

The atopic dermatitis PK-PD model of lebrikizumab was developed based on EASI scores up to 12 weeks from Clinical Study I and the previously established lebrikizumab population PK model. The PD response effect was the reduction in EASI score. The effects of placebo and/or TCS administration were also incorporated into the model. Covariate analysis suggested that baseline EASI score was a significant covariate on both $K_{out}$, which is the tissue repair rate constant, and $E_{con}$, which is the placebo/TCS effect. The final model is shown in FIG. 5 and the model parameters are provided in Table 4.

TABLE 4

Lebrikizumab Atopic Dermatitis Model Parameters.

| parameter | estimate | 95% CI |
|---|---|---|
| $k_{out}$ (day$^{-1}$) | 0.0540 | (0.0379, 0.0819) |
| $E_{con}$ | 0.268 | (0.200, 0.361) |
| $E_{max}$ | 0.729 | (0.363, 1.00) |
| $EC_{50}$ (µg/mL) | 8.08 | (0.612, 44.1) |
| baseline effect on $k_{out}$ | −0.280 | (−0.821, 1.42) |
| baseline effect on $E_{con}$ | −0.639 | (−1.93, 0.235) |
| $\omega_{k_{out}}$ | 0.468 | (0.171, 0.836) |
| $\omega_{E_{con}}$ | 1.05 | (0.817, 1.16) |
| $\rho_{k_{out}} \times E_{con}$ | −0.443 | (−1.00, 0.204) |
| $\sigma$ | 0.469 | (0.427, 0.501) |

The confidence intervals are the 2.5$^{th}$ and 97.5$^{th}$ percentiles of the parameters estimated for 1000 bootstrap samples; see FIG. 5 drawing description for explanation of symbols.

The model includes certain assumptions, such as the assumption that the exposure-response relationship is similar across all drug concentrations, however, we found that it adequately described the change in raw EASI score observed in Study 1. Additionally, the model was able to predict EASI-50, EASI-75, and EASI-90 responses through Week 12 from Study 1 very well despite not being designed for this purpose. This result provided additional validation for the model and increased our confidence in its accuracy and robustness.

We used the final model to simulate a number of dosing regimens and then we predicted EASI scores at various times during treatment. The dosing regimens simulated are provided in Table 5 below. All simulations were conducted over a 24-week time period. A dosing regimen of 125 mg administered once every four weeks was used as a reference point to compare all of the simulated results. As shown in Table 5, the simulated dosing regimens were broadly categorized into four groups: Group 1 regimens were loading dose and maintenance dose permutations, Group 2 regimens were 250 mg administered once every four weeks-based permutations, Group 3 regimens were 250 mg administered once every eight weeks-based permutations, and Group 4 regimens were lower dosing permutations based on 37.5 mg administered once every four weeks.

TABLE 5

Dosing Regimens Simulated with the Lebrikizumab AD Model.

| Loading Dose | Maintenance Dose | Duration | Group |
|---|---|---|---|
| 250 mg at Day 1 | 125 mg every four weeks starting at Week 4 | 24 weeks | 1 |
| 250 mg at Day 1, 250 mg at Day 15 | 125 mg every four weeks starting at Week 4 | 24 weeks | 1 |
| 250 mg at Day 1 and Day 29 | 125 mg every four weeks starting at Week 8 | 24 weeks | 1 |
| 500 mg at Day 1 | 125 mg every four weeks starting at Week 4 | 24 weeks | 1 |

TABLE 5-continued

Dosing Regimens Simulated with the Lebrikizumab AD Model.

| Loading Dose | Maintenance Dose | Duration | Group |
|---|---|---|---|
| None | 250 mg every four weeks starting at Day 1 | 24 weeks | 2 |
| 500 mg at Day 1 | 250 mg every four weeks starting at Week 4 | 24 weeks | 2 |
| None | 250 mg every eight weeks starting at Day 1 | 24 weeks | 3 |
| 500 mg at Day 1 | 250 mg every eight weeks starting at Week 4 | 24 weeks | 3 |
| None | 37.5 mg every four weeks | 24 weeks | 4 |
| 125 mg at Day 1 | 37.5 mg every four weeks | 24 weeks | 4 |

Figure 6:
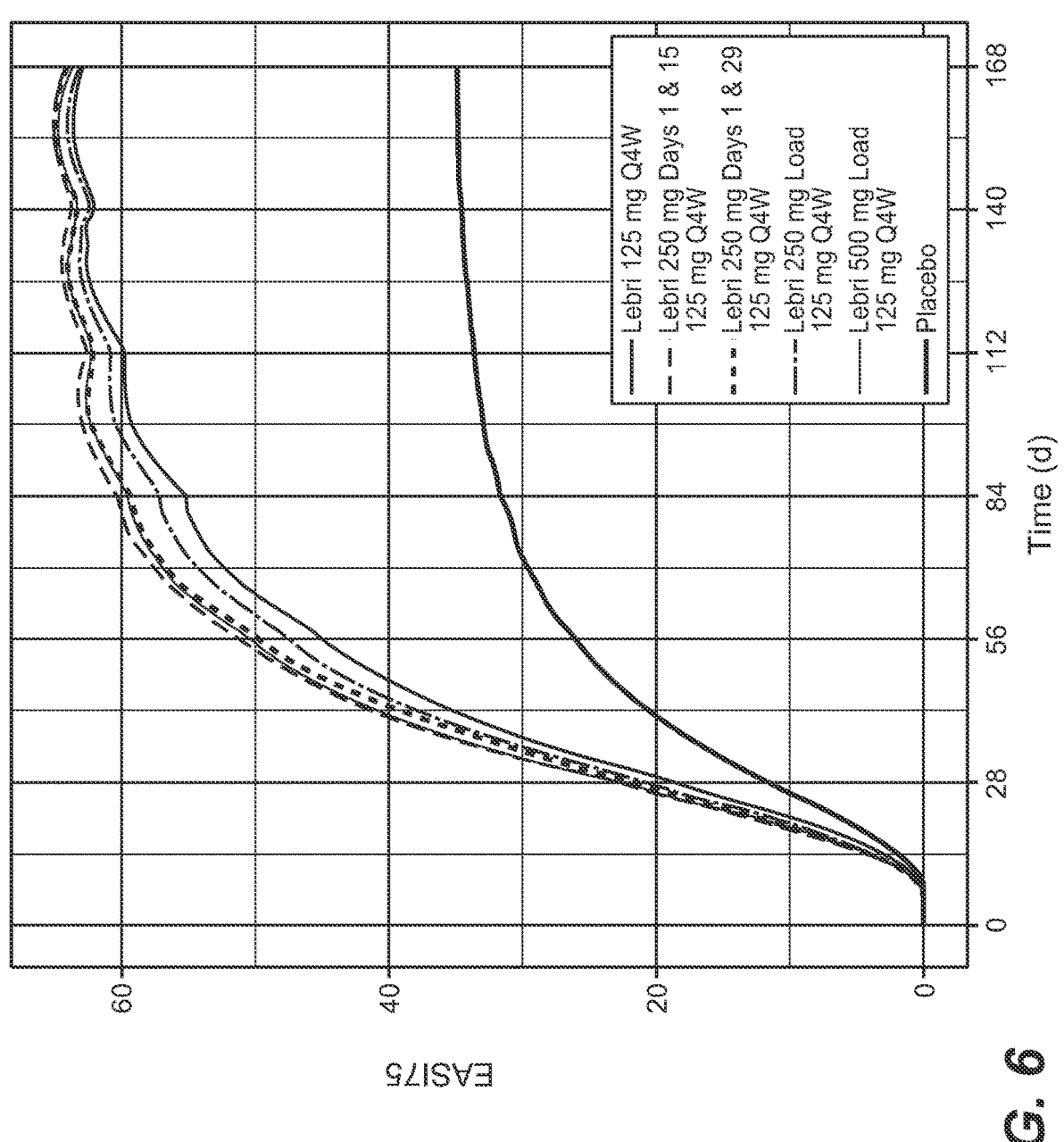
FIG. 6 shows the model-predicted median EASI-75 responses over time for Group 1 (see Table 5) lebrikizumab dosing regimens as described in Example 3. The heavy solid line is the median simulated response for placebo treatment (the improvement in EASI-75 in placebo treatment represents the likely contribution of topical corticosteroids to the overall efficacy). The medium solid line is the median simulated response for the 125 mg lebrikizumab administered once every four weeks (Lebri 125 mg Q4W) dosing regimen. The dot-dash line is the median simulated response for a 250 mg loading dose given on Day 1 followed by a 125 mg maintenance dose of lebrikizumab administered once every four weeks (Lebri 250 mg load, 125 mg Q4W) beginning at Week 4. The light solid line is the median simulated response for a 500 mg loading dose given at Day 1 followed by a 125 mg maintenance dose of lebrikizumab administered once every four weeks (Lebri 500 mg load, 125 mg Q4W) beginning at Week 4. The heavy dashed line is the median simulated response for a 250 mg dose of lebrikizumab administered on Days 1 and 29 followed by a 125 mg maintenance dose of lebrikizumab administered once every four weeks (Lebri 250 mg days 1 & 29, 125 mg Q4W) starting at Week 8. The light dashed line is the median simulated response for a 250 mg dose of lebrikizumab administered on Days 1 and 15 followed by a 125 mg maintenance dose of lebrikizumab administered once every four weeks (Lebri 250 mg days 1 & 15, 125 mg Q4W) beginning at Week 4 (Day 29). Confidence intervals were removed from the plots for clarity.

Simulations of patients achieving EASI-75 over time with each of the Group 1 lebrikizumab dosing regimens are shown in FIG. 6. The PK-PD model predicted that all loading dose permutations resulted in small improvements in EASI-75 response over the 125 mg once every four weeks regimen alone. This improvement was most evident in the middle portion of the curve (e.g. Day 56-84) and was mostly diluted out by later time points (Day 140-168).

Figure 7:
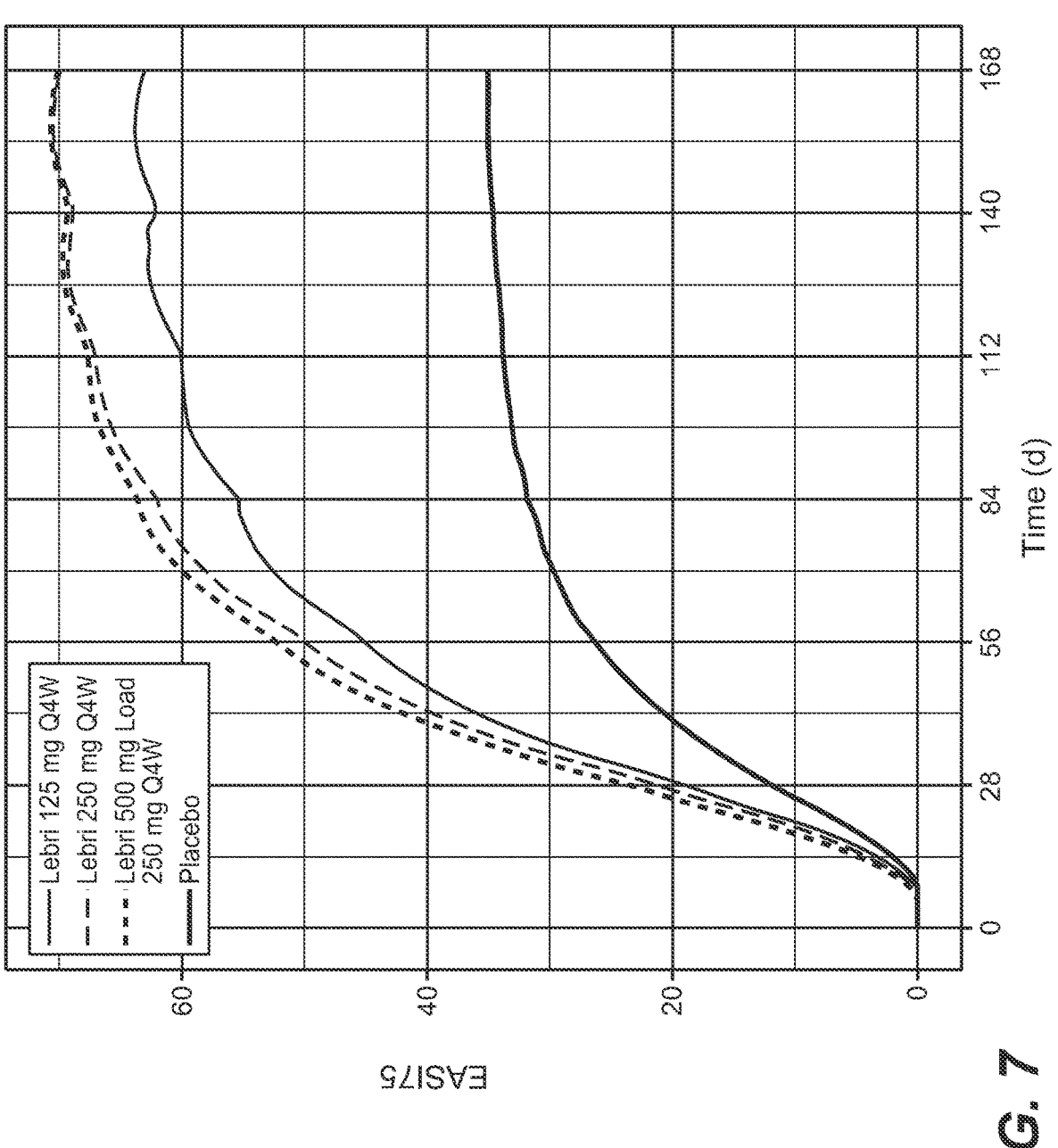
FIG. 7 shows the model-predicted median EASI-75 responses over time for Group 2 (see Table 5) lebrikizumab dosing regimens as described in Example 3. The heavy solid line is the median simulated response for placebo treatment (the improvement in EASI-75 in placebo treatment represents the likely contribution of topical corticosteroids to the overall efficacy). The medium solid line is the median simulated response for the 125 mg lebrikizumab administered once every four weeks (Lebri 125 mg Q4W) dosing regimen. The light dashed line is the median simulated response for the 250 mg lebrikizumab administered once every four weeks (Lebri 250 mg Q4W) dosing regimen. The heavy dashed line is a 500 mg loading dose administered at Day 1 followed by a 250 mg maintenance dose of lebrikizumab administered once every four weeks beginning at week 4 (Lebri 500 mg load, 250 mg Q4W). Confidence intervals were removed from the plots for clarity.

Simulations of patients achieving EASI-75 over time with each of the Group 2 lebrikizumab dosing regimens are shown in FIG. 7. The PK-PD model predicted that the 250 mg once every four weeks-based regimens began to show separation (i.e., an improvement in EASI-75) from the 125 mg once every four weeks-regimen during the middle portion of the curve, and that separation was maintained at later time points.

Figure 8:
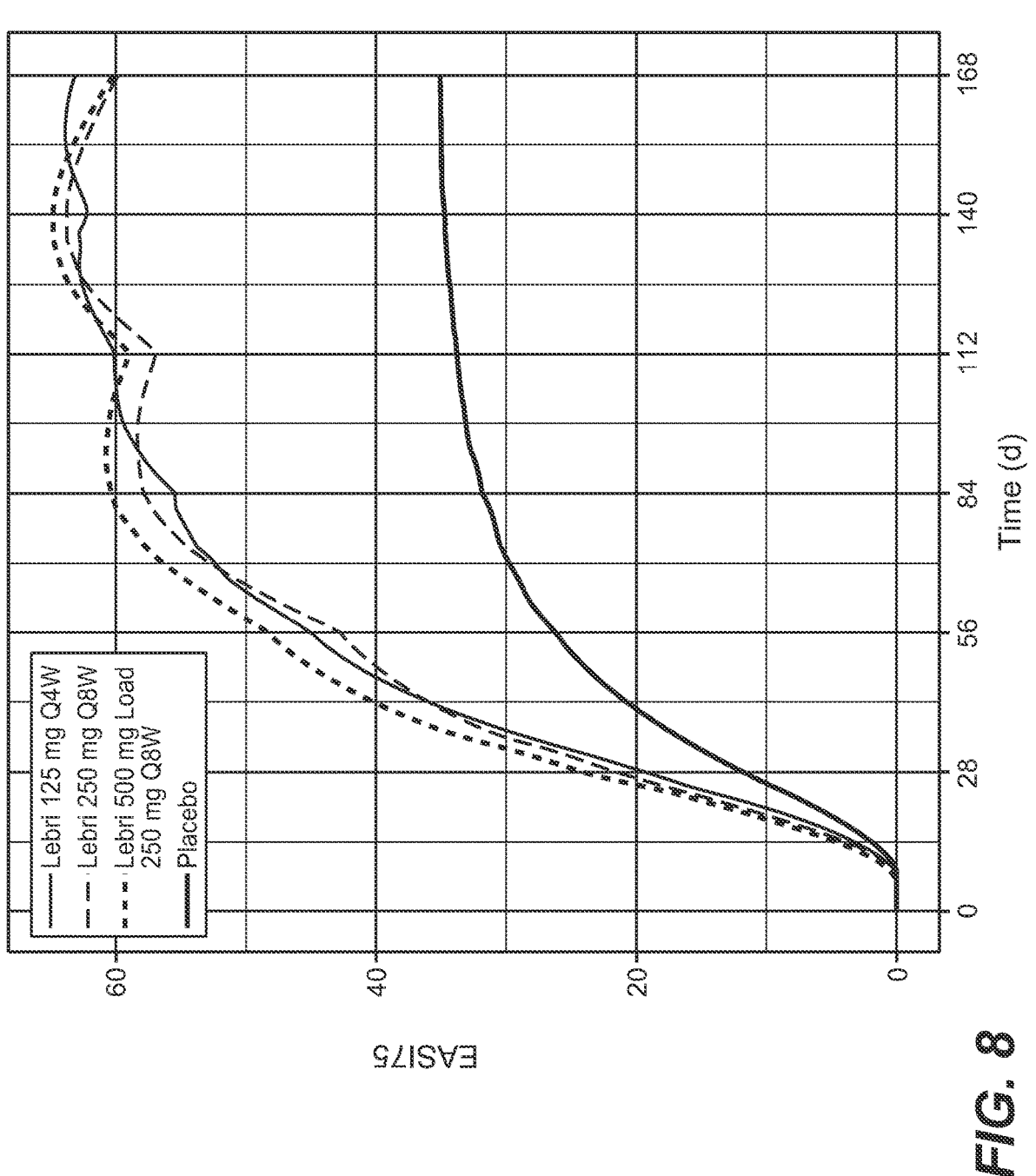
FIG. 8 shows the model-predicted median EASI-75 responses over time for Group 3 (see Table 5) dosing regimens as described in Example 3. The heavy solid line is the median simulated response for placebo treatment (the improvement in EASI-75 in placebo treatment represents the likely contribution of topical corticosteroids to the overall efficacy). The medium solid line is the median simulated response for the 125 mg lebrikizumab administered once every four weeks (Lebri 125 mg Q4W) dosing regimen. The light dashed line is the median simulated response for 250 mg lebrikizumab administered once every eight weeks (Lebri 250 Q8W). The heavy dashed line is the median simulated response for a 500 mg loading dose followed by a maintenance dose of 250 mg lebrikizumab administered once every eight weeks beginning on week 4 (Lebri 500 mg load, 250 mg Q8W). Confidence intervals were removed from the plots for clarity.

Simulations of patients achieving EASI-75 over time with each of the Group 3 lebrikizumab dosing regimens are shown in FIG. 8. The PK-PD model predicted that the 250 mg administered once every eight weeks regimens had comparable efficacy to the 125 mg administered once every four weeks regimen, with a slight improvement in off weeks (e.g., at Week 12 and Week 20), and a slightly worse result during a Week before the next dose was given (e.g., at Week 8 and Week 16).

Figure 9:
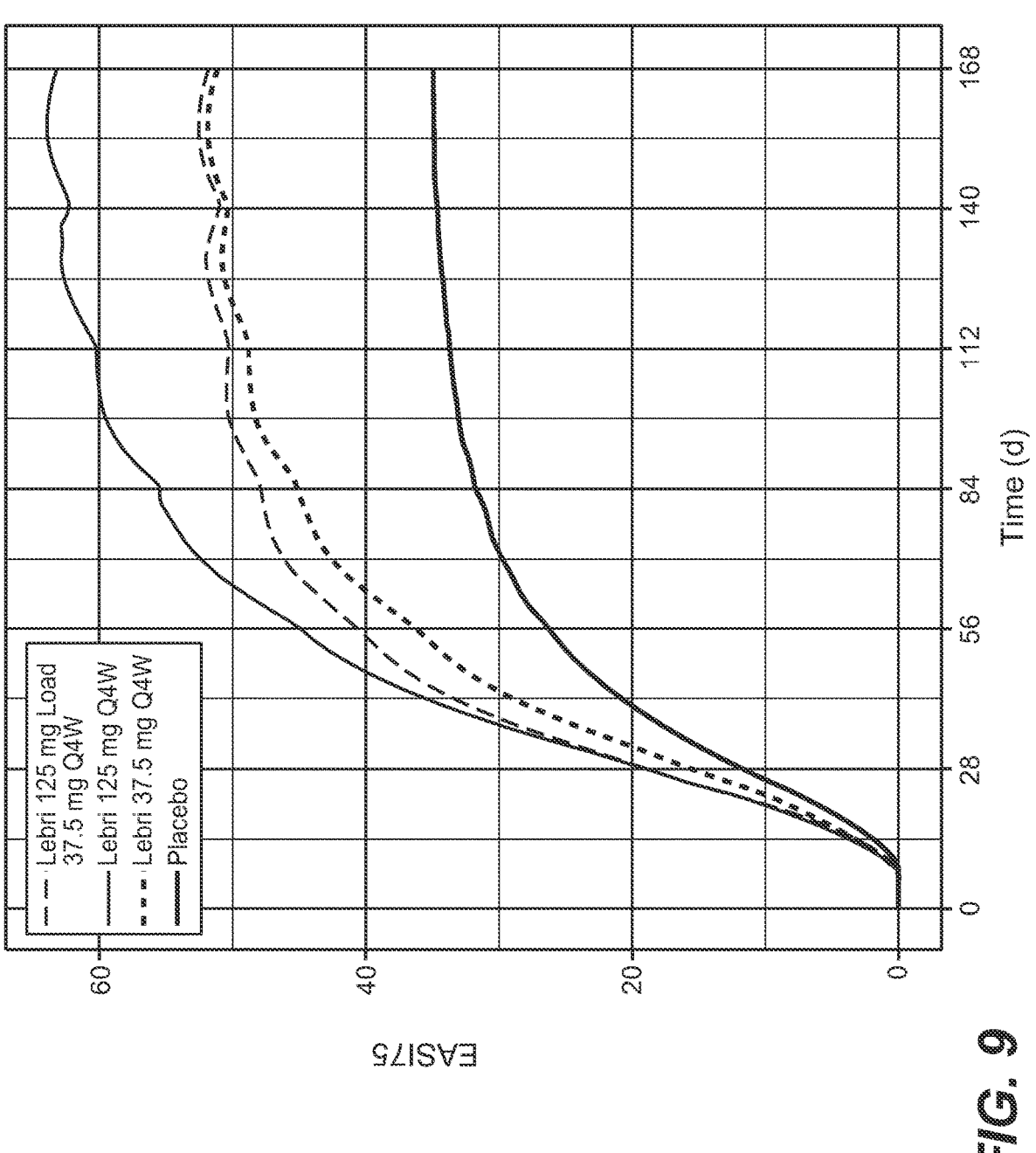
FIG. 9 shows the model-predicted median EASI-75 responses over time for Group 4 (see Table 5) lebrikizumab dosing regimens as described in Example 3. The heavy solid line is the median simulated response for placebo treatment (the improvement in EASI-75 in placebo treatment represents the likely contribution of topical corticosteroids to the overall efficacy). The medium solid line is the median simulated response for the 125 mg lebrikizumab administered once every four weeks (Lebri 125 mg Q4W) dosing regimen. The heavy dashed line is the median simulated response for 37.5 mg lebrikizumab administered once every four weeks dosing regimen (Lebri 37.5 mg Q4W). The light dashed line is the median simulated response for a 125 mg loading dose followed by a maintenance dose of 37.5 mg lebrikizumab administered once every four weeks beginning on week 4 (Lebri 125 mg load, 37.5 mg Q4W). Confidence intervals were removed from the plots for clarity.

Simulations of patients achieving EASI-75 over time with each of the Group 4 lebrikizumab dosing regimens are shown in FIG. 9. The PK-PD model predicted that the 37.5 mg administered once every four weeks regimens were less efficacious than the 125 mg administered once every four weeks dosing regimen.

In summary, the lebrikizumab atopic dermatitis PK-PD model predicted that all "once every four weeks" lebrikizumab dosing regimens provided equivalent or better EASI-75 scores compared to EASI-75 scores achieved with 125 mg administered once every four weeks (the dose clinically tested in the Phase II Clinical Study I described above) with the exception of dosing regimens that included a dose of 37.5 mg lebrikizumab administered once every four weeks. These simulations showed that 37.5 mg lebrikizumab administered once every four weeks was predicted to be less efficacious, as assessed by EASI-75 scores, than any of the other simulated dosing regimens.

The lebrikizumab atopic dermatitis PK-PD model also predicted that the best EASI-75 result was obtained with 250 mg lebrikizumab administered once every four weeks (with or without a loading dose) for a treatment duration of 16-24 weeks. The model also predicted that the inclusion of a loading dose improved the EASI-75 result at earlier time points (e.g., at 8 or 12 weeks), but that the impact of this improvement compared to dosing regimens lacking a loading dose diminished over time (e.g., at 20 or 24 weeks). Thus, inclusion of a loading dose may provide improved treatment benefit to patients early in the course of treatment. Finally, the model predicted that administration of 250 mg of lebrikizumab once every eight weeks resulted in EASI-75 improvements similar to the EASI-75 results predicted with administration of 125 mg of lebrikizumab once every four weeks. The overall improvement in EASI-75 for the "250 mg q8w regimen" was predicted to be somewhat higher during weeks when the 250 mg dose was not administered (e.g., at week 4) and slightly lower than the "125 mg q4w regimen" immediately prior to a 250 mg dose administration (e.g., at week 8). Thus, the modeling results described here demonstrate that a number of lebrikizumab dosing regimens are predicted to provide therapeutic benefit to atopic dermatitis patients.

Example 4

Clinical Study II

Figure 10:
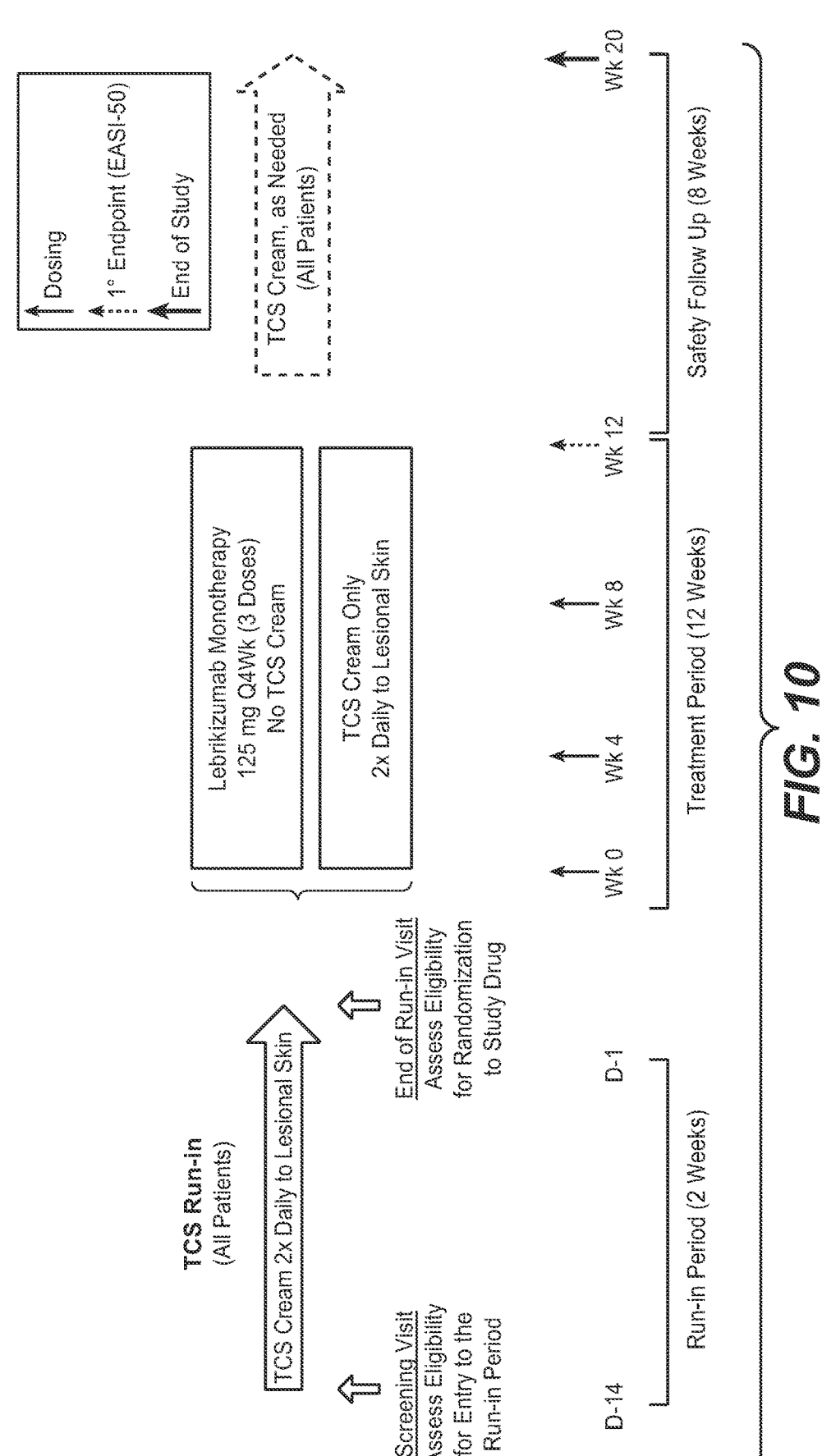
FIG. 10 shows the Study II Schema as described in Example 4. Abbreviations are as follows: D=day; EASI=Eczema Area and Severity Index; q4wk=every 4 weeks; TCS=topical corticosteroid; Wk=week.

Clinical Study II was a Phase II, randomized, open label study to evaluate the safety and efficacy of lebrikizumab monotherapy in adult patients (18-75 years of age) with persistent moderate to severe AD, who were inadequately controlled by TCS. The Study II Schema is provided in FIG. 10.

Screening. Patients eligible to enroll in the Study had to meet all eligibility criteria described below.

The inclusion criteria included the following: age 18 to 75 years; AD diagnosed by the Hanifin/Rajka criteria and that had been present for at least 1 year at screening; moderate to severe AD as graded by the Rajka/Langeland criteria at screening; history of inadequate response to a 1 month (within the 3 months prior to the screening visit) treatment regimen of at least daily TCS and regular emollient for treatment of AD; EASI score 14 at screening and end of the run-in period (Visit 3), IGA score 3 (5-point scale) at screening and end of the run-in period (Visit 3); AD involvement of 10% body surface area (BSA) at screening; and Pruritus VAS score (measured as part of the SCORAD) of 3 at screening; adherence to the protocol-specified 2-week run-in period TCS regimen (at least 10 out of 14 days) at the time of entry into the treatment period (Day 1).

Exclusion criteria included the following: past and/or current use of any anti-IL-13 or anti-IL-4/IL-13 therapy, including lebrikizumab; use of an investigational agent within 4 weeks prior to screening or within 5 half-lives of the investigational agent, whichever is longer; history of a severe allergic reaction or anaphylactic reaction to a biologic agent or known hypersensitivity to any component of the lebrikizumab injection; hypersensitivity to TCS or to any other ingredients contained by the TCS product used in the study; use of any complementary, alternative, or homeopathic medicines including, but not limited to, phytotherapies, traditional or non-traditional herbal medications, essential fatty acids, or acupuncture within 7 days prior to the run-in period or need for such medications during the study; body weight <40 kg or body mass index >38 kg/m$^2$; evidence of other skin conditions; including, but not limited to, T-cell lymphoma or allergic contact dermatitis; evidence of, or ongoing treatment (including topical antibiotics) for active skin infection at screening (Day −15); certain infections; history of recent or active (within 6 months) parasitic infections, especially nematodes (e.g., Ascaris, Ancylostoma), Platyhelminthes (e.g., Schistosoma), or history of Listeria infections; active tuberculosis requiring treatment within the 12 months prior to Visit 1; evidence of acute or chronic hepatitis or known liver cirrhosis; known immuno-deficiency, including HIV infection; use of TCI (topical calcineurin inhibitor) at the time of screening; use of a tanning booth/parlor within 4 weeks before the screening visit; allergen immunotherapy within 3 months of screening; receipt of a live attenuated vaccine within 4 weeks prior to baseline visit (Day 1); planned surgery during the study; clinically significant abnormality on screening ECG or laboratory tests (hematology, serum chemistry, and urinalysis); AST, ALT, or total bilirubin elevation ≥2.0× the upper limit of normal (ULN) during screening; known current malignancy or current evaluation for a potential malignancy, including basal or squamous cell carcinoma of the skin or carcinoma in situ; history of malignancy within 5 years prior to screening, except for appropriately treated carcinoma in situ of the cervix, non-melanoma skin carcinoma; stage I uterine cancer; and other clinically significant medical disease that is uncontrolled despite treatment.

Run-in Period. Following screening, eligible patients entered a 2-week run-in period (Days −14 to −1). After the run-in period, patients stopped use of their pre-study TCS (and other AD medications) and began a protocol-specified topical therapy regimen as outlined below. On the first day of the run-in period (Day −14) patients received TCS for use throughout the run-in period. Specifically, patients received triamcinolone acetonide 0.1% cream for use on the body and hydrocortisone 2.5% cream for use on the face and intertriginous areas. Patients were instructed to apply emollient to all xerotic skin surfaces at least once daily and to apply cream to active skin lesions twice per day and not to apply cream to unaffected areas.

At the end of the run-in period, an assessment of disease severity was performed and patients who continued to demonstrate moderate to severe AD as assessed by EASI and IGA (see Inclusion Criteria above) were eligible for randomization to study drug (lebrikizumab) or TCS alone.

Treatment Period (Weeks 1-12). At the end of the run-in period, patients who had demonstrated adherence to the protocol-specified TCS regimen and continued to fulfill the eligibility criteria (see Inclusion Criteria above) were randomized. A total of approximately 50 patients were randomized (1:1) to one of the following two treatment groups (see FIG. 10): Group 1: 125 mg of lebrikizumab administered by subcutaneous (SC) injection every 4 weeks (Q4W) for a total of 3 doses; and Group 2: TCS cream alone. Patients randomized to Group 1 did not receive a protocol-specified TCS regimen and patients randomized to Group 2 continued to apply TCS using the same TCS regimen that was applied during the run-in period (two times daily to lesional skin only).

Safety Follow-up Period (Weeks 13-20). All patients who completed study treatment during the treatment period (Weeks 1-12) were followed for safety for an additional 8 weeks (Weeks 13-20). During this safety follow-up period, patients in Group 2 (TCS only) were no longer required to apply the protocol specified TCS regimen as specified during the run-in and treatment periods. Instead, triamcinolone acetonide 0.1% cream and/or hydrocortisone 2.5% cream could be applied to active skin lesions only, as determined by the patient and the study investigator. Likewise, patients in treatment Group 1 (lebrikizumab monotherapy) could use triamcinolone acetonide 0.1% cream and/or hydrocortisone 2.5% cream on active skin lesions only, as determined by the patient and the study investigator. All patients were encouraged to continue applying emollients at least once daily to xerotic skin.

Topical calcineruin inhibitors (TCIs) were not allowed at any time during this study. Patients who had been using TCIs at the time of screening were allowed to participate in the study if they agreed to stop using TCIs during the study and if, in the opinion of the investigator, it was safe to stop the use of TCI and use the protocol specified TCS cream instead.

Rationale for Lebrikizumab Dose and Schedule. The rationale for the lebrikizumab dose and schedule for Study II was similar to the rationale described above for Study I. One lebrikizumab dose regimen (125 mg Q4W [Group 1]) was tested in this Phase II study. The 125-mg Q4W dose regimen was included as a potentially effective dose and was the highest dose regimen being studied in the pivotal Phase III adult studies (LAVOLTA I and II) of lebrikizumab in asthma. Given the expected similarity in the role of IL-13 and the pharmacokinetics between asthma and AD, it was hypothesized that this dose could be effective in patients with AD.

As described above, however, the results of the LAVOLTA I and II studies were inconsistent. Hanania et al., Lancet Respir Med 2016, available at dx(dot)doi(dot)org (slash)52213-2600(16)30265-X, published online Sep. 5, 2016. Both studies failed to show a clear dose-response although pharmacokinetic and pharmacodynamics results were consistent with those from the phase II studies described previously, indicating that drug exposures were similar and that the IL-13 pathway was inhibited. Hanania et al., 2016, supra. Accordingly, it was uncertain whether lebrikizumab would provide clinically meaningful benefit to atopic dermatitis patients at the dosing regimens described herein.

The primary endpoint for the Phase II study was measured at Week 12. The mean serum lebrikizumab trough concentration at Week 12 was expected to be over 90% of the steady state value for patients receiving 125 mg Q4W. In addition, for the 125 mg Q4W dose, the predicted trough concentrations at Week 12 would be well within the range where lebrikizumab demonstrated biological activity in the Phase II asthma clinical trials.

Rationale for Control Group. Patients in treatment Group 2 received TCS cream alone and therefore served as an active comparator. This treatment group was used as a control for lebrikizumab SC to adequately assess the safety and efficacy of lebrikizumab as monotherapy compared with TCS.

The active TCS comparator group was included since TCS use is the standard of care in clinical practice (European Academy of Dermatology and Venereology [EADV] 2009 guidelines; Darsow et al., J Eur Acad Dermatol Venereol 2010; 24:317-28; American Academy of Dermatology 2014 guidelines; Eichenfield et al., J Am Acad Dermatol 2014: 71(1):116-32).

Efficacy Outcome Measures. The exploratory efficacy outcome measures of lebrikizumab monotherapy compared to TCS alone for this study were as follows, in order: (i) percent of patients with a 50% or 75% (EAST 50/75) reduction from baseline EASI at Week 12 (EASI-50 and EASI-75 were defined as a 50% and 75% reduction, respectively, in EASI score at Week 12 compared to baseline); (ii) percent and absolute change from baseline in EASI score at Week 12; (iii) percent of patients achieving an IGA score of 0 or 1 at Week 12; (iv) percent of patients with a ≥2 point reduction from baseline in IGA at Week 12; (v) absolute change from baseline in IGA at Week 12; (vi) percent of patients achieving an IGSA score of 0 or 1 at Week 12; (vii) percent of patients with a ≥2 point reduction from baseline in IGSA at Week 12; (viii) absolute change from baseline in IGSA at Week 12; (ix) percent and absolute change from baseline in SCORAD at Week 12; (x) percent of patients with a 50% or 75% reduction (SCORAD 50/75) from baseline in SCORAD score at Week 12; (xi) percent change from baseline in total percent body surface area (BSA)

affected at Week 12; (xii) absolute- and percent-change from baseline in pruritus as measured by the Pruritus VAS (assessed as part of the SCORAD) at Week 12; (xiii) number of disease flares from baseline to Week 12; and (xiv) percent of patients who receive non-protocol specified TCS before Week 12.

Safety Outcome Measures. The safety outcome measures for this study were as follows: (i) incidence of treatment-emergent adverse events at Week 12 with lebrikizumab used as monotherapy compared to TCS alone; (ii) incidence of human anti-therapeutic antibodies (ATA) at baseline and during the study; (iii) frequency and severity of skin and other organ system infections throughout the study; the clinical definition of skin infection was as follows: the diagnosis of infection was based on the Investigator's clinical assessment including but not limited to the presence of honey-colored crusting, serous discharge, pustules, or pain at the site of rash and that may be associated with systemic features, including fever or a flare in AD disease (defined above); (iv) incidence of disease rebound following discontinuation of study drug as assessed by the investigator; the clinical definition of disease rebound was: a significant worsening of disease severity after cessation of therapy to a severity level that is greater than prior to commencing therapy (Hijnen et al., J Eur Acad Dermatol Venereol 2007; 21(1) 85-9); (v) incidence of injection site reactions from baseline to Week 12; and (vi) frequency and severity of treatment-emergent adverse events, including adverse events of special interest from baseline to Week 12.

Results. The key efficacy results from Clinical Study II are summarized in Table 6 below. The data show that lebrikizumab monotherapy over the 12 week study period was effective. The EASI-75 and EASI-90 results were similar between the lebrikizumab and TCS treatment arms while the IGA, SCORAD, and pruritus results were somewhat lower in the lebrikizumab arm than in the TCS arm.

TABLE 6

| Key Efficacy Results at Week 12. | | | | |
|---|---|---|---|---|
| | Baseline to Week 12 | | Day −14 to Week 12 | |
| Endpoint | TCS (n = 27) | lebrikizumab (n = 28) | TCS (n = 27) | lebrikizumab (n = 28) |
| EASI-75 | 37.0% | 39.3% | 37.0% | 42.9% |
| EASI-90 | 7.4% | 14.3% | 22.2% | 14.3% |
| IGA 0/1 | 25.9% | 7.1% | 25.9% | 7.1% |
| % change in EASI | −57.7% | −44.0% | −64.0% | −53.8% |
| % change in SCORAD | −41.3% | −26.6% | −48.9% | −40.5% |
| % change in BSA | −43.2% | −43.2% | −47.5% | −52.2% |
| % change in pruritus VAS* | −34.9% | −14.5% | −53.2% | −39.6% |

*in patients with baseline pruritus VAS ≥3.

Anti-IL13 Antibody (Lebrikizumab) Amino Acid Sequences

The table below shows the amino acid sequences of the CDR-H1, CDR-H2, CDR-H3, CDR-L1, CDR-L2, and CDR-L3 regions of lebrikizumab, along with VH, VL, heavy chain sequences and light chain sequences. As indicated in the Table of Sequences below and as described above, VH and the heavy chain may include an N-terminal glutamine and the heavy chain may also include a C-terminal lysine. As is well known in the art, N-terminal glutamine residues can form pyroglutamate and C-terminal lysine residues can be clipped during manufacturing processes.

TABLE OF SEQUENCES

| SEQ ID NO: | Description | Sequence | | | |
|---|---|---|---|---|---|
| 1 | lebrikizumab heavy chain variable region | VTLRESGPAL | VKPTQTLTLT | CTVSGFSLSA | YSVNWIRQPP |
| | | GKALEWLAMI | WGDGKIVYNS | ALKSRLTISK | DTSKNQVVLT |
| | | MTNMDPVDTA | TYYCAGDGYY | PYAMDNWGQG | SLVTVSS |
| 2 | lebrikizumab light chain variable region | DIVMTQSPDS | LSVSLGERAT | INCRASKSVD | SYGNSFMHWY |
| | | QQKPGQPPKL | LIYLASNLES | GVPDRFSGSG | SGTDFTLTIS |
| | | SLQAEDVAVY | YCQQNNEDPR | TFGGGTKVEI | K |
| 3 | Alternate lebrikizumab VH | QVTLRESGPA | LVKPTQTLTL | TCTVSGFSLS | AYSVNWIRQP |
| | | PGKALEWLAM | IWGDGKIVYN | SALKSRLTIS | KDTSKNQVVL |
| | | TMTNMDPVDT | ATYYCAGDGY | YPYAMDNWGQ | GSLVTVSS |
| 4 | Alternate lebrikizumab VL | DIVMTQSPDS | LSVSLGERAT | INCRASKSVD | SYGNSFMHWY |
| | | QQKPGQPPKL | LIYLASNLES | GVPDRFSGSG | SGTDFTLTIS |
| | | SLQAEDVAVY | YCQQNNEDPR | TFGGGTKVEI | KR |
| 5 | lebrikizumab HVR-H1 | AYSVN | | | |
| 6 | lebrikizumab HVR-H2 | MIWGDGKIVYNSALKS | | | |
| 7 | lebrikizumab HVR-H3 | DGYYPYAMDN | | | |
| 8 | lebrikizumab HVR-L1 | RASKSVDSYGNSFMH | | | |
| 9 | lebrikizumab HVR-L2 | LASNLES | | | |
| 10 | lebrikizumab HVR-L3 | QQNNEDPRT | | | |
| 11 | lebrikizumab heavy chain | QVTLRESGPA | LVKPTQTLTL | TCTVSGFSLS | AYSVNWIRQP |
| | | PGKALEWLAM | IWGDGKIVYN | SALKSRLTIS | KDTSKNQVVL |
| | | TMTNMDPVDT | ATYYCAGDGY | YPYAMDNWGQ | GSLVTVSSAS |
| | | TKGPSVFPLA | PCSRSTSEST | AALGCLVKDY | FPEPVTVSWN |
| | | SGALTSGVHT | FPAVLQSSGL | YSLSSVVTVP | SSSLGTKTYT |
| | | CNVDHKPSNT | KVDKRVESKY | GPPCPPCPAP | EFLGGPSVFL |
| | | FPPKPKDTLM | ISRTPEVTCV | VVDVSQEDPE | VQFNWYVDGV |
| | | EVHNAKTKPR | EEQFNSTYRV | VSVLTVLHQD | WLNGKEYKCK |
| | | VSNKGLPSSI | EKTISKAKGQ | PREPQVYTLP | PSQEEMTKNQ |
| | | VSLTCLVKGF | YPSDIAVEWE | SNGQPENNYK | TTPPVLDSDG |
| | | SFFLYSRLTV | DKSRWQEGNV | FSCSVMHEAL | HNHYTQKSLS |
| | | LSLGK | | | |
| 12 | lebrikizumab light chain | DIVMTQSPDS | LSVSLGERAT | INCRASKSVD | SYGNSFMHWY |
| | | QQKPGQPPKL | LIYLASNLES | GVPDRFSGSG | SGTDFTLTIS |
| | | SLQAEDVAVY | YCQQNNEDPR | TFGGGTKVEI | KRTVAAPSVF |
| | | IFPPSDEQLK | SGTASVVCLL | NNFYPREAKV | QWKVDNALQS |
| | | GNSQESVTEQ | DSKDSTYSLS | STLTLSKADY | EKHKVYACEV |
| | | THQGLSSPVT | KSFNRGEC | | |

The invention claimed is:

1. A method of treating atopic dermatitis in a patient, the method comprising administering to the patient an IL-13 antibody, wherein administering comprises administering a loading dose of 250 mg or 500 mg of the anti-IL-13 antibody and administering a subsequent maintenance dose of 125 mg of the anti-IL-13 antibody, wherein the loading dose is administered once or twice, and the maintenance dose is administered for the remainder of treatment duration, wherein the anti-IL-13 antibody is an antibody comprising a heavy chain having the amino acid sequence of SEQ ID NO: 11 and a light chain having the amino acid sequence of SEQ ID NO: 12, wherein the administration of the anti-IL-13 antibody reduces disease severity in the patient, and wherein the disease severity is assessed by an Atopic Dermatitis Disease Severity Outcome Measure.

2. The method of claim 1, wherein the maintenance dose is administered four weeks after administration of the loading dose, and once every four weeks thereafter for the treatment duration.

3. The method of claim 1, wherein the treatment duration is 24 weeks or more.

4. The method of claim 3, wherein the treatment duration is 24 weeks.

5. The method of claim 1, wherein the Atopic Dermatitis Disease Severity Outcome Measure is Eczema Area and Severity Index (EASI).

6. The method of claim 1, wherein the Atopic Dermatitis Disease Severity Outcome Measure is Severity Scoring of Atopic Dermatitis (SCORAD).

7. The method of claim 1, wherein the Atopic Dermatitis Disease Severity Outcome Measure is Investigator Global Assessment (IGA).

8. The method of claim 1, wherein the Atopic Dermatitis Disease Severity Outcome Measure is a Patient Reported Outcome (PRO).

9. The method of claim 8, wherein the PRO is pruritus visual analogue scale (VAS), sleep loss VAS, or Atopic Dermatitis Impact Questionnaire (ADIQ) score.

10. The method of claim 1, wherein the atopic dermatitis is moderate to severe as determined by Rajka/Langeland criteria score and wherein the Rajka/Langeland criteria score is determined to be between 4.5 and 9.

11. The method of claim 1, wherein the IL-13 antibody is administered subcutaneously to the patient using a subcutaneous administration device.

12. The method of claim 11, wherein the subcutaneous administration device is selected from a prefilled syringe, disposable pen injection device, microneedle device, microinfuser device, needle-free injection device, and autoinjector device.

13. The method of claim 1, wherein the method further comprises administration of one or more topical corticosteroids.

14. The method of claim 13, wherein the one or more topical corticosteroids is or are administered before, concurrent with, or after administration of the IL-13 antibody.

15. The method of claim 14, wherein the one or more topical corticosteroids is or are selected from triamcinolone acetonide, hydrocortisone, and a combination of triamcinolone acetonide and hydrocortisone.

16. The method of claim 1, wherein the patient is 12 years of age or older.

17. The method of claim 1, wherein the patient's atopic dermatitis is inadequately controlled by topical corticosteroids.

* * * * *

SEQUENCE LISTING

Sequence total quantity: 12
SEQ ID NO: 1                moltype = AA   length = 117
FEATURE                     Location/Qualifiers
REGION                      1..117
                            note = source = /note="Description of Artificial Sequence:
                            Syntheticpolypeptide"
source                      1..117
                            mol_type = protein
                            organism = synthetic construct
SEQUENCE: 1
VTLRESGPAL VKPTQTLTLT CTVSGFSLSA YSVNWIRQPP GKALEWLAMI WGDGKIVYNS   60
ALKSRLTISK DTSKNQVVLT MTNMDPVDTA TYYCAGDGYY PYAMDNWGQG SLVTVSS      117

SEQ ID NO: 2                moltype = AA   length = 111
FEATURE                     Location/Qualifiers

```
REGION                    1..111
                          note = source = /note="Description of Artificial Sequence:
                           Syntheticpolypeptide"
source                    1..111
                          mol_type = protein
                          organism = synthetic construct
SEQUENCE: 2
DIVMTQSPDS LSVSLGERAT INCRASKSVD SYGNSFMHWY QQKPGQPPKL LIYLASNLES  60
GVPDRFSGSG SGTDFTLTIS SLQAEDVAVY YCQQNNEDPR TFGGGTKVEI K          111

SEQ ID NO: 3              moltype = AA  length = 118
FEATURE                   Location/Qualifiers
REGION                    1..118
                          note = source = /note="Description of Artificial Sequence:
                           Syntheticpolypeptide"
source                    1..118
                          mol_type = protein
                          organism = synthetic construct
SEQUENCE: 3
QVTLRESGPA LVKPTQTLTL TCTVSGFSLS AYSVNWIRQP PGKALEWLAM IWGDGKIVYN  60
SALKSRLTIS KDTSKNQVVL TMTNMDPVDT ATYYCAGDGY YPYAMDNWGQ GSLVTVSS   118

SEQ ID NO: 4              moltype = AA  length = 112
FEATURE                   Location/Qualifiers
REGION                    1..112
                          note = source = /note="Description of Artificial Sequence:
                           Syntheticpolypeptide"
source                    1..112
                          mol_type = protein
                          organism = synthetic construct
SEQUENCE: 4
DIVMTQSPDS LSVSLGERAT INCRASKSVD SYGNSFMHWY QQKPGQPPKL LIYLASNLES  60
GVPDRFSGSG SGTDFTLTIS SLQAEDVAVY YCQQNNEDPR TFGGGTKVEI KR         112

SEQ ID NO: 5              moltype = AA  length = 5
FEATURE                   Location/Qualifiers
REGION                    1..5
                          note = source = /note="Description of Artificial Sequence:
                           Syntheticpeptide"
source                    1..5
                          mol_type = protein
                          organism = synthetic construct
SEQUENCE: 5
AYSVN                                                               5

SEQ ID NO: 6              moltype = AA  length = 16
FEATURE                   Location/Qualifiers
REGION                    1..16
                          note = source = /note="Description of Artificial Sequence:
                           Syntheticpeptide"
source                    1..16
                          mol_type = protein
                          organism = synthetic construct
SEQUENCE: 6
MIWGDGKIVY NSALKS                                                  16

SEQ ID NO: 7              moltype = AA  length = 10
FEATURE                   Location/Qualifiers
REGION                    1..10
                          note = source = /note="Description of Artificial Sequence:
                           Syntheticpeptide"
source                    1..10
                          mol_type = protein
                          organism = synthetic construct
SEQUENCE: 7
DGYYPYAMDN                                                         10

SEQ ID NO: 8              moltype = AA  length = 15
FEATURE                   Location/Qualifiers
REGION                    1..15
                          note = source = /note="Description of Artificial Sequence:
                           Syntheticpeptide"
source                    1..15
                          mol_type = protein
                          organism = synthetic construct
SEQUENCE: 8
RASKSVDSYG NSFMH                                                   15

SEQ ID NO: 9              moltype = AA  length = 7
```

-continued

```
FEATURE              Location/Qualifiers
REGION               1..7
                     note = source = /note="Description of Artificial Sequence:
                     Syntheticpeptide"
source               1..7
                     mol_type = protein
                     organism = synthetic construct
SEQUENCE: 9
LASNLES                                                              7

SEQ ID NO: 10        moltype = AA  length = 9
FEATURE              Location/Qualifiers
REGION               1..9
                     note = source = /note="Description of Artificial Sequence:
                     Syntheticpeptide"
source               1..9
                     mol_type = protein
                     organism = synthetic construct
SEQUENCE: 10
QQNNEDPRT                                                            9

SEQ ID NO: 11        moltype = AA  length = 445
FEATURE              Location/Qualifiers
REGION               1..445
                     note = source = /note="Description of Artificial Sequence:
                     Syntheticpolypeptide"
source               1..445
                     mol_type = protein
                     organism = synthetic construct
SEQUENCE: 11
QVTLRESGPA LVKPTQTLTL TCTVSGFSLS AYSVNWIRQP PGKALEWLAM IWGDGKIVYN  60
SALKSRLTIS KDTSKNQVVL TMTNMDPVDT ATYYCAGDGY YPYAMDNWGQ GSLVTVSSAS  120
TKGPSVFPLA PCSRSTSEST AALGCLVKDY FPEPVTVSWN SGALTSGVHT FPAVLQSSGL  180
YSLSSVVTVP SSSLGTKTYT CNVDHKPSNT KVDKRVESKY GPPCPPCPAP EFLGGPSVFL  240
FPPKPKDTLM ISRTPEVTCV VVDVSQEDPE VQFNWYVDGV EVHNAKTKPR EEQFNSTYRV  300
VSVLTVLHQD WLNGKEYKCK VSNKGLPSSI EKTISKAKGQ PREPQVYTLP PSQEEMTKNQ  360
VSLTCLVKGF YPSDIAVEWE SNGQPENNYK TTPPVLDSDG SFFLYSRLTV DKSRWQEGNV  420
FSCSVMHEAL HNHYTQKSLS LSLGK                                         445

SEQ ID NO: 12        moltype = AA  length = 218
FEATURE              Location/Qualifiers
REGION               1..218
                     note = source = /note="Description of Artificial Sequence:
                     Syntheticpolypeptide"
source               1..218
                     mol_type = protein
                     organism = synthetic construct
SEQUENCE: 12
DIVMTQSPDS LSVSLGERAT INCRASKSVD SYGNSFMHWY QQKPGQPPKL LIYLASNLES  60
GVPDRFSGSG SGTDFTLTIS SLQAEDVAVY YCQQNNEDPR TFGGGTKVEI KRTVAAPSVF  120
IFPPSDEQLK SGTASVVCLL NNFYPREAKV QWKVDNALQS GNSQESVTEQ DSKDSTYSLS  180
STLTLSKADY EKHKVYACEV THQGLSSPVT KSFNRGEC                           218
```